United States Patent
Wilton et al.

(10) Patent No.: US 12,159,690 B2
(45) Date of Patent: *Dec. 3, 2024

(54) ANCESTRY COMPOSITION DETERMINATION

(71) Applicant: 23andMe, Inc., Sunnyvale, CA (US)

(72) Inventors: Peter Richard Wilton, Los Gatos, CA (US); Gabriel David Poznik, Menlo Park, CA (US); Kimberly Faith McManus, San Francisco, CA (US); Ethan Macneil Jewett, San Jose, CA (US); William Allen Freyman, Menlo Park, CA (US); Adam Auton, Menlo Park, CA (US)

(73) Assignee: 23andMe, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/377,219

(22) Filed: Oct. 5, 2023

(65) Prior Publication Data
US 2024/0062845 A1 Feb. 22, 2024

Related U.S. Application Data

(63) Continuation of application No. 17/444,989, filed on Aug. 12, 2021, now Pat. No. 11,817,176.
(Continued)

(51) Int. Cl.
*G06F 7/00* (2006.01)
*G06F 16/28* (2019.01)
(Continued)

(52) U.S. Cl.
CPC .......... *G16B 10/00* (2019.02); *G06F 16/285* (2019.01); *G06N 7/01* (2023.01); *G16B 5/20* (2019.02); *G16B 40/00* (2019.02)

(58) Field of Classification Search
CPC .......... G16B 10/00; G16B 40/00; G16B 5/20; G06F 16/285; G06N 7/01
(Continued)

(56) References Cited

U.S. PATENT DOCUMENTS 5,692,501 A 12/1997 Minturn
6,570,567 B1 5/2003 Eaton
(Continued)

FOREIGN PATENT DOCUMENTS

WO 2004097712 A2 11/2004
WO 2006089238 W 8/2006
(Continued)

OTHER PUBLICATIONS

Cavalli-Sforza et al., The History and Geography of Human Genes, 1994, pp. 77-81, 90-93, 169-171.
(Continued)

*Primary Examiner* — Isaac M Woo
(74) *Attorney, Agent, or Firm* — McDonnell Boehnen Hulbert & Berghoff LLP; David K. Buckingham

(57) ABSTRACT

Presenting ancestral origin information, comprising: receiving a request to display ancestry data of an individual; obtaining ancestry composition information of the individual, the ancestry composition information including information pertaining to a proportion of the individual's genotype data that is deemed to correspond to a specific ancestry; and presenting the ancestry composition information to be displayed.

20 Claims, 47 Drawing Sheets

Related U.S. Application Data

(60) Provisional application No. 63/093,039, filed on Oct. 16, 2020, provisional application No. 62/706,396, filed on Aug. 13, 2020.

(51) Int. Cl.
  *G06N 7/01* (2023.01)
  *G16B 5/20* (2019.01)
  *G16B 10/00* (2019.01)
  *G16B 40/00* (2019.01)

(58) Field of Classification Search
  USPC .................................................. 707/600–899
  See application file for complete search history.

(56) References Cited

U.S. PATENT DOCUMENTS

| | | |
|---|---|---|
| 6,703,228 B1 | 3/2004 | Landers |
| 7,142,205 B2 | 11/2006 | Chithambaram |
| 7,567,894 B2 | 7/2009 | Durand |
| 7,729,863 B2 | 6/2010 | Ostrander |
| 7,797,302 B2 | 9/2010 | Kenedy |
| 7,818,281 B2 | 10/2010 | Kennedy |
| 7,818,310 B2 | 10/2010 | Kenedy |
| 7,844,609 B2 | 11/2010 | Kenedy |
| 7,848,914 B2 | 12/2010 | Durand |
| 7,917,438 B2 | 3/2011 | Kenedy |
| 7,933,912 B2 | 4/2011 | Kenedy |
| 7,941,329 B2 | 5/2011 | Kenedy |
| 7,941,434 B2 | 5/2011 | Kenedy |
| 7,951,078 B2 | 5/2011 | Scheuner |
| 7,957,907 B2 | 6/2011 | Sorenson |
| 7,983,893 B2 | 7/2011 | Durand |
| 8,024,348 B2 | 9/2011 | Kenedy |
| 8,051,033 B2 | 11/2011 | Kenedy |
| 8,055,643 B2 | 11/2011 | Kenedy |
| 8,065,324 B2 | 11/2011 | Kenedy |
| 8,099,424 B2 | 1/2012 | Kenedy |
| 8,108,406 B2 | 1/2012 | Kenedy |
| 8,156,158 B2 | 4/2012 | Rolls |
| 8,185,461 B2 | 5/2012 | Kenedy |
| 8,187,811 B2 | 5/2012 | Eriksson |
| 8,195,446 B2 | 6/2012 | Durand |
| 8,200,509 B2 | 6/2012 | Kenedy |
| 8,207,316 B1 | 6/2012 | Bentwich |
| 8,209,319 B2 | 6/2012 | Kenedy |
| 8,214,192 B2 | 7/2012 | Durand |
| 8,214,195 B2 | 7/2012 | Durand |
| 8,224,835 B2 | 7/2012 | Kenedy |
| 8,255,403 B2 | 8/2012 | Kenedy |
| 8,285,486 B2 | 10/2012 | Martin |
| 8,326,648 B2 | 12/2012 | Kenedy |
| 8,386,519 B2 | 2/2013 | Kenedy |
| 8,428,886 B2 | 4/2013 | Wong |
| 8,443,339 B2 | 5/2013 | Letourneau |
| 8,452,619 B2 | 5/2013 | Kenedy |
| 8,458,097 B2 | 6/2013 | Kenedy |
| 8,458,121 B2 | 6/2013 | Kenedy |
| 8,463,554 B2 | 6/2013 | Hon |
| 8,467,976 B2 | 6/2013 | Lo |
| 8,473,273 B2 | 6/2013 | Durand |
| 8,510,057 B1 | 8/2013 | Avey |
| 8,543,339 B2 | 9/2013 | Wojcicki |
| 8,589,437 B1 | 11/2013 | Khomenko |
| 8,606,761 B2 | 12/2013 | Kenedy |
| 8,645,118 B2 | 2/2014 | Durand |
| 8,645,343 B2 | 2/2014 | Wong |
| 8,655,899 B2 | 2/2014 | Kenedy |
| 8,655,908 B2 | 2/2014 | Kenedy |
| 8,655,915 B2 | 2/2014 | Kenedy |
| 8,666,271 B2 | 3/2014 | Saiki |
| 8,666,721 B2 | 3/2014 | Durand |
| 8,685,737 B2 | 4/2014 | Serber |
| 8,719,045 B2 | 5/2014 | Yoon |
| 8,731,819 B2 | 5/2014 | Dzubay |
| 8,738,297 B2 | 5/2014 | Sorenson |
| 8,786,603 B2 | 7/2014 | Rasmussen |
| 8,788,283 B2 | 7/2014 | Kenedy |
| 8,788,286 B2 | 7/2014 | Kenedy |
| 8,798,915 B2 | 8/2014 | Dzubay |
| 8,855,935 B2 | 10/2014 | Myres |
| 8,990,198 B2 | 3/2015 | Rolls |
| 8,990,250 B1 | 3/2015 | Chowdry |
| 9,026,423 B2 | 5/2015 | Durand |
| 9,031,870 B2 | 5/2015 | Kenedy |
| 9,116,882 B1 | 8/2015 | Macpherson |
| 9,170,992 B2 | 10/2015 | Kenedy |
| 9,213,944 B1 | 12/2015 | Do |
| 9,213,947 B1 | 12/2015 | Do |
| 9,218,451 B2 | 12/2015 | Wong |
| 9,262,567 B2 | 2/2016 | Durand |
| 9,323,632 B2 | 4/2016 | Durand |
| 9,336,177 B2 | 5/2016 | Hawthorne |
| 9,367,663 B2 | 6/2016 | Deciu |
| 9,367,800 B1 | 6/2016 | Do |
| 9,390,225 B2 | 7/2016 | Barber |
| 9,405,818 B2 | 8/2016 | Chowdry |
| 9,582,647 B2 | 2/2017 | Kenedy |
| 9,836,576 B1 | 12/2017 | Do |
| 9,864,835 B2 | 1/2018 | Avey |
| 9,886,576 B2 | 2/2018 | Urakabe |
| 9,977,708 B1 | 5/2018 | Do |
| 10,025,877 B2 | 7/2018 | Macpherson |
| 10,127,346 B2 | 11/2018 | Dewey |
| 10,162,880 B1 | 12/2018 | Chowdry |
| 10,275,569 B2 | 4/2019 | Avey |
| 10,296,847 B1 | 5/2019 | Do |
| 10,379,812 B2 | 8/2019 | Kenedy |
| 10,432,640 B1 | 10/2019 | Hawthorne |
| 10,437,858 B2 | 10/2019 | Naughton |
| 10,516,670 B2 | 12/2019 | Hawthorne |
| 10,572,831 B1 | 2/2020 | Do |
| 10,643,740 B2 | 5/2020 | Avey |
| 10,658,071 B2 | 5/2020 | Do |
| 10,691,725 B2 | 6/2020 | Naughton |
| 10,699,803 B1 | 6/2020 | Do |
| 10,755,805 B1 | 8/2020 | Do |
| 10,777,302 B2 | 9/2020 | Chowdry |
| 10,790,041 B2 | 9/2020 | Macpherson |
| 10,803,134 B2 | 10/2020 | Kenedy |
| 10,841,312 B2 | 11/2020 | Hawthorne |
| 10,854,318 B2 | 12/2020 | Macpherson |
| 10,891,317 B1 | 1/2021 | Chowdry |
| 10,896,233 B2 | 1/2021 | Kenedy |
| 10,936,626 B1 | 3/2021 | Naughton |
| 10,957,455 B2 | 3/2021 | Kenedy |
| 10,991,467 B2 | 4/2021 | Kenedy |
| 10,999,285 B2 | 5/2021 | Hawthorne |
| 11,003,694 B2 | 5/2021 | Kenedy |
| 11,031,101 B2 | 6/2021 | Hon |
| 11,049,589 B2 | 6/2021 | Hon |
| 11,170,047 B2 | 11/2021 | Macpherson |
| 11,170,873 B2 | 11/2021 | Avey |
| 11,171,962 B2 | 11/2021 | Hawthorne |
| 11,211,149 B2 * | 12/2021 | Curtis .................. G16B 10/00 |
| 11,322,227 B2 | 5/2022 | Hon |
| 11,720,632 B2 | 8/2023 | Jiang |
| 2002/0095585 A1 | 7/2002 | Scott |
| 2002/0133495 A1 | 9/2002 | Hugh, Jr. |
| 2003/0113727 A1 | 6/2003 | Girn |
| 2003/0113729 A1 | 6/2003 | Daquino |
| 2003/0130798 A1 | 7/2003 | Hood |
| 2003/0135096 A1 | 7/2003 | Dodds |
| 2003/0172065 A1 | 9/2003 | Sorenson |
| 2003/0179223 A1 | 9/2003 | Ying |
| 2003/0186244 A1 | 10/2003 | Margus |
| 2004/0002818 A1 | 1/2004 | Kulp |
| 2004/0088191 A1 | 5/2004 | Holden |
| 2004/0146870 A1 | 7/2004 | Liao |
| 2004/0175700 A1 | 9/2004 | Geesaman |
| 2004/0229213 A1 | 11/2004 | Legrain |
| 2004/0229231 A1 | 11/2004 | Frudakis |
| 2004/0241730 A1 | 12/2004 | Yakhini |

(56) References Cited

U.S. PATENT DOCUMENTS

| | | |
|---|---|---|
| 2005/0039110 A1 | 2/2005 | De La Vega |
| 2005/0191731 A1 | 9/2005 | Judson |
| 2005/0250151 A1 | 11/2005 | Mei |
| 2006/0003354 A1 | 1/2006 | Krantz |
| 2006/0046256 A1 | 3/2006 | Halldorsson |
| 2006/0100872 A1 | 5/2006 | Yokoi |
| 2006/0142949 A1 | 6/2006 | Helt |
| 2006/0161460 A1 | 7/2006 | Smitherman |
| 2006/0166224 A1 | 7/2006 | Norviel |
| 2006/0257888 A1 | 11/2006 | Zabeau |
| 2006/0287876 A1 | 12/2006 | Jedlicka |
| 2007/0037182 A1 | 2/2007 | Gaskin |
| 2007/0150978 A1 | 6/2007 | Byrum |
| 2007/0178500 A1 | 8/2007 | Martin |
| 2007/0250809 A1 | 10/2007 | Kennedy |
| 2007/0277267 A1 | 11/2007 | Byrum |
| 2008/0004848 A1 | 1/2008 | Avey |
| 2008/0008996 A1 | 1/2008 | Byrum |
| 2008/0081331 A1 | 4/2008 | Myres |
| 2008/0131887 A1 | 6/2008 | Stephan |
| 2008/0154566 A1 | 6/2008 | Myres |
| 2008/0189047 A1 | 8/2008 | Wong |
| 2008/0227063 A1 | 9/2008 | Kenedy |
| 2008/0228043 A1 | 9/2008 | Kenedy |
| 2008/0228410 A1 | 9/2008 | Kenedy |
| 2008/0228451 A1 | 9/2008 | Kenedy |
| 2008/0228677 A1 | 9/2008 | Kenedy |
| 2008/0228698 A1 | 9/2008 | Kenedy |
| 2008/0228699 A1 | 9/2008 | Kenedy |
| 2008/0228700 A1 | 9/2008 | Kenedy |
| 2008/0228701 A1 | 9/2008 | Kenedy |
| 2008/0228702 A1 | 9/2008 | Kenedy |
| 2008/0228704 A1 | 9/2008 | Kenedy |
| 2008/0228705 A1 | 9/2008 | Kenedy |
| 2008/0228706 A1 | 9/2008 | Kenedy |
| 2008/0228708 A1 | 9/2008 | Kenedy |
| 2008/0228722 A1 | 9/2008 | Kenedy |
| 2008/0228753 A1 | 9/2008 | Kenedy |
| 2008/0228756 A1 | 9/2008 | Kenedy |
| 2008/0228757 A1 | 9/2008 | Kenedy |
| 2008/0228765 A1 | 9/2008 | Kenedy |
| 2008/0228766 A1 | 9/2008 | Kenedy |
| 2008/0228767 A1 | 9/2008 | Kenedy |
| 2008/0228768 A1 | 9/2008 | Kenedy |
| 2008/0228797 A1 | 9/2008 | Kenedy |
| 2008/0243843 A1 | 10/2008 | Kenedy |
| 2008/0255768 A1 | 10/2008 | Martin |
| 2008/0270366 A1 | 10/2008 | Frank |
| 2009/0043752 A1 | 2/2009 | Kenedy |
| 2009/0099789 A1 | 4/2009 | Stephan |
| 2009/0112871 A1 | 4/2009 | Hawthorne |
| 2009/0118131 A1 | 5/2009 | Avey |
| 2009/0119083 A1 | 5/2009 | Avey |
| 2009/0182579 A1 | 7/2009 | Liu |
| 2009/0198519 A1 | 8/2009 | McNamar |
| 2009/0299645 A1 | 12/2009 | Colby |
| 2010/0042438 A1 | 2/2010 | Moore |
| 2010/0063830 A1 | 3/2010 | Kenedy |
| 2010/0063835 A1 | 3/2010 | Kenedy |
| 2010/0063865 A1 | 3/2010 | Kenedy |
| 2010/0070292 A1 | 3/2010 | Kenedy |
| 2010/0070455 A1 | 3/2010 | Halperin |
| 2010/0076950 A1 | 3/2010 | Kenedy |
| 2010/0076988 A1 | 3/2010 | Kenedy |
| 2010/0145981 A1 | 6/2010 | Wojcicki |
| 2010/0169262 A1 | 7/2010 | Kenedy |
| 2010/0169313 A1 | 7/2010 | Kenedy |
| 2010/0169338 A1 | 7/2010 | Kenedy |
| 2010/0191513 A1 | 7/2010 | Listgarten |
| 2010/0281401 A1 | 11/2010 | Tebbs |
| 2011/0078168 A1 | 3/2011 | Kenedy |
| 2011/0130337 A1 | 6/2011 | Eriksson |
| 2011/0184656 A1 | 7/2011 | Kenedy |
| 2011/0257889 A1 | 10/2011 | Klammer |
| 2012/0270190 A1 | 10/2012 | Kenedy |
| 2012/0270794 A1 | 10/2012 | Eriksson |
| 2012/0301864 A1 | 11/2012 | Bagchi |
| 2013/0080068 A1 | 3/2013 | Dewey |
| 2013/0080365 A1 | 3/2013 | Dewey |
| 2013/0085728 A1 | 4/2013 | Tang |
| 2013/0149707 A1 | 6/2013 | Sorenson |
| 2013/0345988 A1 | 12/2013 | Avey |
| 2014/0006433 A1 | 1/2014 | Hon |
| 2014/0045705 A1 | 2/2014 | Bustamante |
| 2014/0067280 A1 | 3/2014 | Vockley |
| 2014/0067355 A1 | 3/2014 | Noto |
| 2015/0227610 A1 | 8/2015 | Chowdry |
| 2015/0248473 A1 | 9/2015 | Kenedy |
| 2015/0347566 A1 | 12/2015 | Kenedy |
| 2016/0026755 A1 | 1/2016 | Byrnes |
| 2016/0103950 A1 | 4/2016 | Myres |
| 2016/0171155 A1 | 6/2016 | Do |
| 2016/0277408 A1 | 9/2016 | Hawthorne |
| 2016/0350479 A1 | 12/2016 | Han |
| 2017/0011042 A1 | 1/2017 | Kermany |
| 2017/0017752 A1 | 1/2017 | Noto |
| 2017/0053089 A1 | 2/2017 | Kenedy |
| 2017/0185719 A1 | 6/2017 | Kenedy |
| 2017/0220738 A1 | 8/2017 | Barber |
| 2017/0228498 A1 | 8/2017 | Hon |
| 2017/0262577 A1 | 9/2017 | Ball |
| 2017/0277827 A1 | 9/2017 | Granka |
| 2017/0277828 A1 | 9/2017 | Avey |
| 2017/0329866 A1 | 11/2017 | Macpherson |
| 2017/0329891 A1 | 11/2017 | Macpherson |
| 2017/0329899 A1 | 11/2017 | Bryc |
| 2017/0329901 A1 | 11/2017 | Chowdry |
| 2017/0329902 A1 | 11/2017 | Bryc |
| 2017/0329904 A1 | 11/2017 | Naughton |
| 2017/0329915 A1 | 11/2017 | Kittredge |
| 2017/0329924 A1 | 11/2017 | Macpherson |
| 2017/0330358 A1 | 11/2017 | Macpherson |
| 2018/0181710 A1 | 6/2018 | Avey |
| 2018/0307778 A1 | 10/2018 | Macpherson |
| 2019/0012431 A1 | 1/2019 | Hon |
| 2019/0026604 A1 | 1/2019 | Sharma |
| 2019/0034163 A1 | 1/2019 | Kenedy |
| 2019/0114219 A1 | 4/2019 | Do |
| 2019/0139623 A1 | 5/2019 | Bryc |
| 2019/0206514 A1 | 7/2019 | Avey |
| 2019/0267115 A1 | 8/2019 | Avey |
| 2019/0281061 A1 | 9/2019 | Hawthorne |
| 2019/0384777 A1 | 12/2019 | Naughton |
| 2020/0137063 A1 | 4/2020 | Hawthorne |
| 2020/0210143 A1 | 7/2020 | Kenedy |
| 2020/0273542 A1 | 8/2020 | Song |
| 2020/0321073 A1 | 10/2020 | Zhi |
| 2020/0372974 A1 | 11/2020 | Chowdry |
| 2021/0020266 A1 | 1/2021 | Freyman |
| 2021/0043278 A1 | 2/2021 | Hon |
| 2021/0043279 A1 | 2/2021 | Hon |
| 2021/0043280 A1 | 2/2021 | Hon |
| 2021/0043281 A1 | 2/2021 | Macpherson |
| 2021/0057041 A1 | 2/2021 | Byrnes |
| 2021/0058398 A1 | 2/2021 | Hawthorne |
| 2021/0074385 A1 | 3/2021 | Hon |
| 2021/0082167 A1 | 3/2021 | Jewett |
| 2021/0166452 A1 | 6/2021 | Jewett |
| 2021/0166823 A1 | 6/2021 | Kenedy |
| 2021/0193257 A1 | 6/2021 | Freyman |
| 2021/0209134 A1 | 7/2021 | Kenedy |
| 2021/0225458 A1 | 7/2021 | Hon |
| 2021/0233665 A1 | 7/2021 | Kenedy |
| 2021/0250357 A1 | 8/2021 | Hawthorne |
| 2021/0313013 A1 | 10/2021 | Hon |
| 2021/0375392 A1 | 12/2021 | Polcari |
| 2022/0044761 A1 | 2/2022 | O'Connell |
| 2022/0051751 A1 | 2/2022 | Wilton |
| 2022/0103560 A1 | 3/2022 | Hawthorne |
| 2022/0115139 A1 | 4/2022 | Paradarami |
| 2022/0139501 A1 | 5/2022 | Hon |
| 2022/0157405 A1 | 5/2022 | Avey |
| 2022/0198726 A1 | 6/2022 | Jewett |

(56) References Cited

U.S. PATENT DOCUMENTS

| | | |
|---|---|---|
| 2022/0223233 A1 | 7/2022 | Bryc |
| 2023/0061512 A1 | 3/2023 | Sams |
| 2023/0352115 A1 | 11/2023 | Girshick |

FOREIGN PATENT DOCUMENTS

| | | |
|---|---|---|
| WO | 2009002942 W | 12/2008 |
| WO | 2009042975 W | 4/2009 |
| WO | 2012099890 W | 7/2012 |
| WO | 2016073953 W | 5/2016 |
| WO | 2017009788 A1 | 1/2017 |
| WO | 2021243094 W | 12/2021 |
| WO | 2022036178 W | 2/2022 |
| WO | 2022076909 W | 4/2022 |
| WO | 2022087478 W | 4/2022 |

OTHER PUBLICATIONS

Extended European Search Report, European Patent Application No. 21856763.4, mailed Nov. 16, 2023.

Khatri et al., Ontological Analysis of Gene Expression Data, 2005, Bioinformatics, vol. 21, No. 18 2005, pp. 3587-3595.

Notice of Allowance, U.S. Appl. No. 18/180,691, mailed Sep. 1, 2023.

Office Action, U.S. Appl. No. 18/157,595, mailed Aug. 24, 2023.

Office Action, U.S. Appl. No. 18/157,595, mailed Jan. 2, 2024.

Office Action, U.S. Appl. No. 18/503,841, mailed Jan. 9, 2024.

Stasko et al., Focus+Context Display and Navigation Techniques for Enhancing Radial, Space-Filling Hierarchy Visualizations, Proc. of the IEEE Symposium on Information Visualization, Feb. 2000.

Canadian Examination Report, Canadian Patent Application No. 3,147,888, mailed Apr. 18, 2024.

Notice of Allowance, U.S. Appl. No. 18/472,019, mailed Apr. 18, 2024.

Office Action, U.S. Appl. No. 18/157,595, mailed Jul. 1, 2024.

Office Action, U.S. Appl. No. 18/737,679, mailed Aug. 7, 2024.

Roberson, Elisha D. O. et al., Visualization of Shared Genomic Regions and Meiotic Recombination in High-Density SNP Data, PLoS One 4(8): e6711. doi:1 0.1371/journal.pone. 0006711 (Aug. 21, 2009).

23andMeBlog [webpage] "New Feature: Ancestry Painting," by 23andMe, Ancestry, published online Mar. 25, 2008, pp. 1. [retrieved May 23, 2018] .

Advisory Action, U.S. Appl. No. 15/950,023, mailed Nov. 23, 2022.

Akbani, R. et al., "Applying Support Vector Machines to Imbalanced Datasets", In Machine Learning: ECML 2004; Boulicaut, J.-F., Esposito, F., Giannotti, F., Pedreschi, D., Eds .; Lecture Notes in Computer Science; Springer Berlin Heidelberg: Berlin, Heidelberg, 2004; vol. 3201, pp. 39-50.

Alexander, et al., "Fast model-based estimation of ancestry in unrelated individuals", Genome Research 19, (2009) pp. 1655-1664.

Assareh, A., et al., "Interaction Trees: Optimizing Ensembles of Decision Trees for Gene-Gene Interaction Detections," 2012 11th International Conference on Machine Learning and Applications, vol. 1, Dec. 2012, pp. 616-621.

Ball, C. et al., "ancestryDNA—AncestryDNA Matching White Paper—Discovering genetic matches across a massive, expanding genetic database" AncestryDNA, Jul. 15, 2020, pp. 1-34.

Ball, C. et al., "ancestryDNA—DNA Circles White Paper—2014" AncestryDNA 2014, pp. 1-43.

Ball, C. et al., [Webpage] "ancestryDNA—Genetic Communities White Paper: Predicting fine-scale ancestral origins from the genetic sharing patterns among millions of individuals" Ancestry.com, Genetic Communities, pp. 1-28. [retrieved on Jan. 22, 2021].

Baran, Y. et al., "Fast and accurate inference of local ancestry in Latino populations", Bioinformatics, 2012, vol. 28, Issue 10, pp. 1359-1367.

Behnel, et al., "Cython: The Best of Both Worlds" Computing in Science and Engineering 13(2) May 2011, pp. 31-39.

Belbin, et al., "Genetic identification of a common collagen disease in Puerto Ricans via identity-by-descent mapping in a health system" eLife, Sep. 2017, 6:e25060, pp. 1-28.

Bercovici, et al., "Ancestry inference in complex admixtures via variablelength Markov chain linkage models" In Proceedings of the 16th Annual Conference on Research in Computational Molecular Biology (RECOMB 2012), pp. 12-28.

Bettinger, B., [webpage] "AncestryDNA Launches New Ethnicity Estimate," The Genetic Genealogist (Internet Blog), published online Sep. 12, 2013, pp. 1-4. [retrieved May 23, 2018].

Bettinger, B., [webpage] "AncestryDNA Officially Launches," The Genetic Genealogist (Internet Blog), published online May 3, 2012, pp. 1-2. [retrieved May 23, 2018].

Bettinger, B., [webpage] "The Monday Morning DNA Testing Company Review â€" AncestryByDNA, The Genetic Genealogist (Internet Blog), published Feb. 26, 2007, p. 1. [retrieved May 23, 2018].

Bohringer, S., et al., "A Software Package for Drawing Ideograms Automatically," Online J Bioinformatics, vol. 1, 2002, pp. 51-61.

Boser, et al., "A training algorithm for optimal margin classifiers" In Proceedings of the fifth annual workshop on computational learning theory, ACM, 1992, pp. 144-152.

Brion, M., et al., "Introduction of a Single Nucleodite Polymorphism—Based Major Y-Chromosome Haplogroup Typing Kit Suitable for Predicting the Geographical Origin of Male Lineages," Electrophoresis, vol. 26, 2005, pp. 4411-4420.

Brisbin, et al., "PCAdmix: principal components-based assignment of ancestry along each chromosome in individuals with admixed ancestry from two or more populations" Human Biology, vol. 84, No. 4 (2012) pp. 343-364.

Browning, Brian L., and Sharon R Browning, "Efficient multilocus association testing for whole genome association 42 studies using localized haplotype clustering", Genetic Epidemiology: The Official Publication of the International Genetic Epidemiology Society 31, No. 5 (2007): 365-375.

Browning, et al., "A Fast, Powerful Method for Detecting Identity by Descent", The American Journal of Human Genetics 88, Feb. 11, 2011, pp. 173-182.

Browning, et al., "Ancestry-specific recent effective population size in the Americas", PLoS Genet 14(5): e1007385, May 24, 2018, pp. 1-22.

Browning, et al., "Detecting Rare Variant Associations by Identity-by-Descent Mapping in Case-Control Studies", Genetics, vol. 190, Apr. 2012, pp. 1521-1531.

Browning, et al., "Identity by Descent Between Distant Relatives: Detection and Applications", Annu. Rev. Genet., Sep. 17, 2012, 46:617-33.

Browning, et al., "Improving the Accuracy and Efficiency of Identity-by-Descent Detection in Population Data", Genetics, vol. 194, Jun. 2013, pp. 459-471.

Browning, S.R., et al., "Haplotype phasing: existing methods and new developments," Nature Reviews | Genetics, vol. 12, Oct. 2011, pp. 703-714. [URL: http://www.nature.com/reviews/genetics].

Browning, Sharon R, and Brian L. Browning, "Rapid and accurate haplotype phasing and missing-data inference for whole-genome association studies by use of localized haplotype clustering," The American Journal of Human Genetics, No. 5 (2007): 1084-1097.

Browning, Sharon R., and Brian L. Browning. "High-resolution detection of identity by descent in unrelated individuals", The American Journal of Human Genetics, 86.4 (2010).

Bryc, et al., "The Genetic Ancestry of African Americans, Latinos, and European Americans across the United States," The American Journal of Human Genetics, vol. 96, Jan. 8, 2015, pp. 37-53.

Burroughs et al., "Analysis of Distributed Intrusion Detection Systems Using Bayesian Methods," Performance, Computing and Communications Conference, 2002, 21st IEEE International. IEEE, 2002, pp. 329-334.

Bycroft, et al., "The UK Biobank resource with deep phenotyping and genomic data", Nature, 562(7726), pp. 203-209, Oct. 2018. ISSN 1476-4687.

(56) References Cited

OTHER PUBLICATIONS

Byrne, J. et al., "The simulation life-cycle: supporting the data collection and representation phase," Simulation Conference (WSC), 2014 Wincer, pp. 2738-2749.
Cann, et al., "A human genome diversity cell line panel" Science, 296(5566), Apr. 12, 2002, vol. 296 No. 5566, pp. 261-262.
Cao, et al., "Design of Reliable System Based on Dynamic Bayesian Networks and Genetic Algorithm," Reliability and Maintainability Symposium (RAMS), 2012 Proceedings—Annual. IEEE, 2012.
Cardena, et al., "Assessment of the Relationship between Self-Declared Ethnicity, Mitochondrial Haplogroups and Genomic Ancestry in Brazilian Individuals," PLOS One, vol. 8, No. 4, Apr. 24, 2013, pp. 1-6.
Carmi, S. et al., "Sequencing and Ashkenazi reference panel supports population-targeted personal genomics and Illuminates Jewish and European origins" Nat. Commun. 5, Sep. 9, 2014, 4835.
Cavalli-Sforza, L., "The Human Genome Diversity Project: past, present and future," Nature Reviews, Genetics, vol. 6, Apr. 2005, pp. 333-340.
Centimorgan, ISOGG Wiki, Jul. 10, 2010 (date of initial version), https://isogg.org/wiki/CentiMorgan.
Chiang, et al., "Conflation of Short Identity-by-Descent Segments Bias Their Inferred Length Distribution", G3 Genes|Genomes|Genetics, vol. 6, No. 5, May 1, 2016, pp. 1287-1296.
Choi, et al., "Comparison of phasing strategies for whole human genomes" PLOS Genetics, 14(4): e1007308, Apr. 5, 2018, pp. 1-26.
Churchhouse, et al., "Multiway Admixture Deconvolution Using Phased or Unphased Ancestral Panels," Wiley Periodical, Inc., Genetic Epidemiology, 2012, pp. 1-12.
Crawford, et al., "Evidence for substantial fine-scale variation in recombination rates across the human genome," Nature Genetics, vol. 36, No. 7, Jul. 2004, pp. 700-706.
De Francesco, L., et al., "Efficient Genotype Elimination Via Adaptive Allele Consolidation," IEEE/ACM Transactions on Computational Biology and Bioinformatics (TCBB), vol. 9, No. 4, Jul. 2012, pp. 1180-1189.
Dean, M., et al., "Polymorphic Admixture Typing in Human Ethnic Populations," American Journal of Human Genetics, vol. 55:4, 1994, pp. 788-808.
Delaneau, et al., "A Linear complexity phasing method for thousands of genomes," Nature Methods, vol. 9, No. 2, Feb. 2012, pp. 179-184.
Delaneau, et al., "Accurate, scalable and integrative haplotype estimation," Nature Communications, (2019) 10:5436, pp. 1-20.
Delaneau, et al., "Integrative haplotype estimation with sub-linear complexity" bioRxiv, Jan. 1, 2018, 493403.
Dempster, et al., "Maximum likelihood from incomplete data via the EM algorithm" Journal of the Royal Statistical Society, Series B, 39(1), 1977, pp. 1-38.
Diaz-Papkovich, et al., "UMAP reveals cryptic population structure and phenotype heterogeneity in large genomic cohorts" PLOS Genetics, 15(II):e1008432, Nov. 1, 2019, pp. 1-24.
Do et al., "A scalable pipeline for local ancestry inference using thousands of reference individuals (Abstract)," From Abstract/Session Information for Program No. 3386W; Session Title: Evolutionary and Population Genetics), ASHG, Aug. 2012.
Dodecad Project, [webpage] "Clusters Galore results, K=73 for Dodecad Project members (up to DOD581)" Dodecad Ancestry Project (Internet Blog), published Mar. 31, 2011, pp. 1-11. [retrieved May 23, 2018].
Dr. D., [webpage] "Population Finder Traces Deep Ancestry," Dr. D Digs Up Ancestors (Internet Blog), DNA Testing, published online Apr. 9, 2011, p. 1. [retrieved May 23, 2018].
Druet, Tom, et al., "A Hidden Markov Model Combining Linkage and Linkage Disequilibrium Information for Haplotype Reconstruction and Quantitative Trait Locus Fine Mapping," Genetics vol. 184, No. 3, Jun. 2010, pp. 789-798.
Durand, E.Y. et al. "Reducing Pervasive False-Positive Identical-by-Descent Segments Detected by Large-Scale Pedigree Analysis" Mol. Bio. Evol. 31(8)(2014) pp. 2212-2222.
Durand, et al., "A scalable pipeline for local ancestry inference using tens of thousands of reference haplotypes" 23andMe, Inc., Oct. 7, 2020, pp. 1-14.
Durand, et al., "Ancestry Composition: A Novel, Efficient Pipeline for Ancestry Deconvolution" 23andMe White paper, Oct. 17, 2014, pp. 1-16.
Durbin, R., "Efficient haplotype matching and storage using the positional Burrows-Wheeler transform (PBWT)" Bioinformatics, Genetics and population analysis, vol. 30, No. 9, Jan. 9, 2014, pp. 1266-1272.
Extended European Search Report, European Patent Application No. 20843426.6, mailed Jul. 7, 2023.
Falush, et al., "Inference of population structure using multilocus genotype data:linked loci and correlated allele frequencies" Genetics 164, (2003) pp. 1567-1587.
Feng et al., "Mining Multiple Temporal Patterns of Complex Dynamic Data Systems," Computational Intelligence and Data Mining, IEEE, 2009, 7 pages.
Finke, K. et al., "Ancestral Haplotype Reconstruction in Endogamous Populations Using Identity-By-Descent" PLOS Computational Biology, Feb. 26, 2021, vol. 17(2):e1008638, pp. 1-14.
Freyman, et al., "Fast and accurate identity-by-descent inference despite haplotype and phasing errors" Phase Aware IBD SMBE 2019 Abstract, 1 page.
Freyman, et al., "Fast and Robust Identity-by-Descent Inference with the Templated Positional Burrows-Wheeler Transform," Mol. Biol. Evol., Advance Access publication: Dec. 23, 2020, pp. 1-21.
Freyman, et al., "Phased IBD: fast and accurate identity-by-descent inference despite haplotype and phasing errors," 23andMe, ProbGen2019 (2019) pp. 1-1.
Freyman, W., "Methods to Infer the Genetic Ancestry of Millions of People," UC Berkeley, Aug. 22, 2019, pp. 1-65.
Fu, W. et al., "Robust Inference of Identity by Descent from Exome-Sequencing Data" The American Journal of Human Genetics 99, Nov. 3, 2016, pp. 1106-1116.
Fuchsberger, et al., "Minimac2: faster genotype imputation," Bioinformatics, vol. 31, No. 5, Oct. 22, 2014, pp. 782-784.
Fujimura, J. H., et al., Different Differences: The Use of 'genetic Ancestry' versus Race in Biomedical Human Genetic Research, Soc. Stud Sci. Feb. 2011 ; 41(1): 5-30.
Gauvin, H. et al., "Genome-wide patterns of identity-by-descent sharing in the French Canadian founder population" European Journal of Human Genetics (2014) 22, pp. 814-821.
Goldberg, et al., "Autosomal Admixture Levels are Informative About Sex Bias in Admixed Populations," Genetics, Nov. 2014, vol. 198, pp. 1209-1229.
Gravel, et al., "Reconstructing Native American Migrations from Whole-Genome and Whole-Exome Data", PLOS Genetics, vol. 9, No. 12, Dec. 2013, e1004023 pp. 1-14.
Gravel, S., "Population Genetics Models of Local Ancestry," Genetics, Jun. 2012, 191(2), pp. 607-619.
Green, et al., "A Draft Sequence of the Neanderthal Genome," Science, vol. 328, May 7, 2010, pp. 710-722.
Gu et al., "Phenotypic Selection for Dormancy Introduced a Set of Adaptive Haplotypes from Weedy Into Cultivated Rice," Genetics Society of America, vol. 171, Oct. 2005, pp. 695-704.
Gusev, A. et al., "The Architecture of Long-Range Haplotypes Shared within and across Populations" Mol. Biol. Evol. 29(2) (2012) pp. 473-486.
Gusev, et al., "Whole population, genome-wide mapping of hidden relatedness," Genome Research, vol. 19, 2009, pp. 318-326.
Halder, Indrani, et al., "A Panel of Ancestry Informative Markers for Estimating Individual Biogeographical Ancestry and Admixture From Four Continents: Utility and Applications," Human Mutation, vol. 29, No. 5, 2008, pp. 648-658.
He, D. et al., "IPEDX: An Exact Algorithm for Pedigree Reconstruction Using Genotype Data," 2013 IEEE International Conference on Bioinformatics and Biomedicine, 2013, pp. 517-520.
He, et al., "Multiple Linear Regression for Index SNP Selection on Unphased Genotypes," Engineering in Medicine and Biology Society, EMBS Annual International Conference of the IEEE, Aug. 30-Sep. 3, 2006, pp. 5759-5762.

(56) References Cited

OTHER PUBLICATIONS

Hellenthal, et al. "A Genetic Atlas of Human Admixture History," Science, vol. 343, Feb. 14, 2014, pp. 747-751.
Henden L, et al., "IBD analysis of Australian amyotrophic lateral sclerosis SOD1-mutation carriers identifies five founder events and links sporadic cases to existing ALS families" bioRxiv. Jan. 1, 2019:685925 pp. 1-26.
Henn, et al., "Cryptic Distant Relatives Are Common in Both Isolated and Cosmopolitan Genetic Samples" PLOS One, 7(4):e34267, Apr. 2012, pp. 1-13.
Hill, et al. "Identification of Pedigree Relationship from Genome Sharing," G3: Gene | Genomes | Genetics, vol. 3, Sep. 2013, pp. 1553-1571.
Howie, et al., "A Flexible and Accurate Genotype Imputation Method for the Next Generation of Genome-Wide Association Studies," PLoS Genetics, vol. 5, No. 6, Jun. 2009, pp. 1-15.
Howie, et al., "Fast and accurate genotype imputation in genome-wide association studies through pre-phasing," Nature Genetics, vol. 44, No. 8, Aug. 2012, pp. 955-960.
Huff, C.D., et al., (2011) "Maximum-likelihood estimation of recent shared ancestry (ERSA)" Genome Research, 21, pp. 768-774.
International HapMap Consortium "A second generation human haplotype map of over 3.1 million SNPs" Nature 449 (764) Oct. 18, 2007, pp. 851-861.
International Search Report, PCT App. No. PCT/US2020/042628, mailed Dec. 29, 2020.
International Search Report, PCT App. No. PCT/US2021/045880, mailed Nov. 15, 2021.
Jaakkola, et al., "Exploiting generative models in discriminative classifiers" Advances in neural information processing systems, (1999) pp. 487-493.
Jia, Jing et al. "Developing a novel panel of genome-wide ancestry informative markers for bio-geographical ancestry estimates," Forensic Science International: Genetics, vol. 8 (2014) pp. 187-194.
Karakuzu, A., et al., "Assessment of In-Vivo Skeletal Muscle Mechanics During Joint Motion Using Multimodal Magnetic Resonance Imaging Based Approaches," Biomedical Engineering Meeting (BIYOMUT), 2014 18th National, pp. 1-4.
Kennedy, et al., "Visual Cleaning of Genotype Data," 2013 IEEE Symposium on Biological Data Visualization (BioVis), Atlanta, Ga., Oct. 2013, pp. 105-112.
Kerchner, [webpage] "DNAPrint Test Results—East Asian vs Native American Minority Admixture Detection," PA Deutsch Ethnic Group DNA Project, created Jun. 26, 2004, updated May 27, 2005, pp. 1-9. [retrieved May 23, 2018].
Kidd, et al. "Population Genetic Inference from Personal Genome Data: Impact of Ancestry and Admixture on Human Genomic Variation," The American Journal of Human Genetics, vol. 91, Oct. 5, 2012, pp. 660-671.
Notice of Allowance, U.S. Appl. No. 13/801,552, mailed Aug. 12, 2015.
Notice of Allowance, U.S. Appl. No. 13/801,653, mailed Dec. 28, 2017.
Notice of Allowance, U.S. Appl. No. 14/938,111, mailed Apr. 29, 2019.
Notice of Allowance, U.S. Appl. No. 14/938,111, mailed Jan. 9, 2020.
Notice of Allowance, U.S. Appl. No. 15/181,083, mailed Aug. 14, 2018.
Notice of Allowance, U.S. Appl. No. 15/181,083, mailed Nov. 15, 2018.
Notice of Allowance, U.S. Appl. No. 15/181,088, mailed Feb. 26, 2020.
Notice of Allowance, U.S. Appl. No. 16/044,364, mailed Nov. 12, 2019.
Notice of Allowance, U.S. Appl. No. 16/446,465, mailed Apr. 2, 2020.
Notice of Allowance, U.S. Appl. No. 17/161,140, mailed Aug. 23, 2022.
Notice of Allowance, U.S. Appl. No. 17/444,989, mailed Feb. 25, 2013.
Notice of Allowance, U.S. Appl. No. 17/682,761, mailed Aug. 10, 2022.
Notice of Allowance, U.S. Appl. No. 18/058,029, mailed Feb. 7, 2023.
Novembre, et al. "Recent advances in the study of fine-scale population structure in humans," Current Opinion in Genetics & Development, vol. 41 (2016), pp. 98-105.
Novembre, et al., "Perspectives on human population structure at the cusp of the sequencing era" Annual Review of Genomics and Human Genetics, 12(1); 2011, pp. 245-274.
O'Dushlaine, C. et al. "Genes Predict Village of Origin in Rural Europe", European Journal of Human Genetics 2010, vol. 18, No. 11, pp. 1269-1270.
Office Action, U.S. Appl. No. 12/381,992, mailed Aug. 2, 2011.
Office Action, U.S. Appl. No. 12/381,992, mailed Dec. 20, 2011.
Office Action, U.S. Appl. No. 12/381,992, mailed Aug. 6, 2013.
Office Action, U.S. Appl. No. 12/381,992, mailed Dec. 27, 2013.
Office Action, U.S. Appl. No. 12/381,992, mailed Aug. 7, 2014.
Office Action, U.S. Appl. No. 12/381,992, mailed Dec. 22, 2014.
Office Action, U.S. Appl. No. 12/381,992, mailed May 22, 2015.
Office Action, U.S. Appl. No. 12/381,992, mailed Nov. 3, 2015.
Office Action, U.S. Appl. No. 12/381,992, mailed Mar. 16, 2016.
Office Action, U.S. Appl. No. 13/800,683, mailed Aug. 12, 2015.
Office Action, U.S. Appl. No. 13/801,056, mailed Jan. 9, 2015.
Office Action, U.S. Appl. No. 13/801,386, mailed Jul. 8, 2015.
Office Action, U.S. Appl. No. 13/801,386, mailed Jan. 11, 2016.
Office Action, U.S. Appl. No. 13/801,386, mailed Oct. 27, 2016.
Office Action, U.S. Appl. No. 13/801,552, mailed Mar. 16, 2015.
Office Action, U.S. Appl. No. 13/801,653, mailed Sep. 30, 2015.
Office Action, U.S. Appl. No. 13/801,653, mailed May 31, 2016.
Office Action, U.S. Appl. No. 13/801,653, mailed Apr. 19, 2017.
Office Action, U.S. Appl. No. 14/924,552, mailed Feb. 9, 2018.
Office Action, U.S. Appl. No. 14/924,552, mailed Sep. 4, 2018.
Office Action, U.S. Appl. No. 14/924,562, mailed Jan. 30, 2018.
Office Action, U.S. Appl. No. 14/924,562, mailed Sep. 13, 2018.
Office Action, U.S. Appl. No. 14/924,562, mailed Jun. 5, 2019.
Office Action, U.S. Appl. No. 14/924,562, mailed Jan. 8, 2020.
Office Action, U.S. Appl. No. 14/938,111, mailed Sep. 25, 2018.
Office Action, U.S. Appl. No. 14/938,111, mailed Jun. 24, 2019.
Office Action, U.S. Appl. No. 15/181,083, mailed Jan. 23, 2018.
Office Action, U.S. Appl. No. 15/181,088, mailed Jun. 25, 2019.
Office Action, U.S. Appl. No. 15/267,053, mailed Sep. 26, 2018.
Office Action, U.S. Appl. No. 15/950,023, mailed Dec. 30. 2020.
Office Action, U.S. Appl. No. 15/950,023, mailed Jun. 29, 2021.
Office Action, U.S. Appl. No. 15/950,023, mailed Jan. 5, 2022.
Office Action, U.S. Appl. No. 15/950,023, mailed Aug. 12, 2022.
Kirkpatrick, B., et al. "Perfect Phylogeny Problems with Missing Values," IEEE/ACM Transactions on Computational Biology and Bioinformatics (TCBB), vol. 11, No. 5, Sep./Oct. 2014, pp. 928-941.
Kraak, M-J, "Visualising Spatial Distributions," Geographical Information Systems: Principles, Techniques, Applications and Management, New York, John Wiley and Sons, 1999, pp. 157-173.
Kumar, et al., "XGMix: Local-Ancestry Inference with Stacked XGBoost" bioRxiv, Apr. 21, 2020, 053876, pp. 1-8.
Lafferty, et al., "Conditional random fields: Probabilistic models for segmenting and labeling sequence data" Proceedings of the 18th International Conference on Machine Learning (ICML-2001), Jun. 28, 2001, pp. 1-10.
Lawson, et al., "Inference of Population Structure using Dense Haplotype Data," PLoS Genetics, vol. 8, No. 1, Jan. 2012, pp. 1-16.
Lazaridis et al., "Ancient Human Genomes Suggest Three Ancestral Populations for Present-Day Europeans," Nature, vol. 513, Sep. 18, 2014, doi:10.1038/nature 13673, pp. 409-413.
Lee, et al., "Comparing genetic ancestry and self-reported race/ethnicity in a multiethnic population in New York City," Journal of Genetics, vol. 89, No. 4, Dec. 2010, pp. 417-423.
Lei, X. et al., "Cloud-Assisted Privacy-Preserving Genetic Paternity Test," 2015 IEEE/CIC International Conference on Communications in China (ICCC), Apr. 7, 2016, pp. 1-6.

(56) References Cited

OTHER PUBLICATIONS

Li, et al. "Worldwide Human Relationships Inferred from Genome-Wide Patterns of Variation," Science, vol. 319, Feb. 22, 2008, pp. 1100-1104.

Li, et al., "Mapping short DNA sequencing reads and calling variants using mapping quality scores," Genome Research, Aug. 19, 2008, pp. 1851-1858.

Li, et al., "Modeling linkage disequilibrium and identifying recombination hotspots using single-nucleotide polymorphism data" Genetics 165, (2003) pp. 2213-2233.

Li, H., et al., "Relationship Estimation from Whole-Genome Sequence Data" PLoS Genet 10(1); (2014) e1004144.

Li, X., et al., "Integrating Phenotype-Genotype Data for Prioritization of Candidate Symptom Genes," 2013 IEEE International Conference on Bioinformatics and Biomedicine, Dec. 2013, pp. 279-280.

Liang et al., "A Deterministic Sequential Monte Carlo Method for Haplotype Inference," IEEE Journal of Selected Topics in Signal Processing, vol. 2, No. 3, Jun. 2008, pp. 322-331.

Liang et al., "The Lengths of Admixture Tracts," Genetics, vol. 197, Jul. 2014, pp. 953-967.

Lin et al. "Polyphase Speech Recognition," Acoustics, Speech and Signal Processing, IEEE International Conference on 2008, IEEE, 2008, 4 pages.

Lin, et al., "Identity-by-Descent Mapping to Detect Rare Variants Conferring Susceptibility to Multiple Sclerosis" PLoS One 8(3), Mar. 5, 2013, e56379, pp. 1-8. doi:10.1371/journal.pone.0056379.

Lipson, et al., "Reconstructing Austronesian population history in Island Southeast Asia," Nature Communications, 5:4689, DOI: 10.1038/ncomms5689, 2014, pp. 1-7.

Loh, et al., "Fast and accurate long-range phasing in a UK Biobank cohort" Nature Genetics, vol. 48, No. 7, Jul. 2016, pp. 811-817.

Loh, et al., "Inferring Admixture Histories of Human Populations Using Linkage Disequilibrium," Genetics, 193(4), Apr. 2013, pp. 1233-1254.

Loh, et al., "Reference-based phasing using the Haplotype Reference Consortium panel" Nat. Genet. Nov. 2016; 48(11): pp. 1443-1448.

Lunter, G., "Fast haplotype matching in very large cohorts using the Li and Stephens model" bioRxiv, Apr. 12, 2016, pp. 1-19.

Lunter, G., "Haplotype matching in large cohorts using the Li and Stephens model" Bioinformatics, Aug. 25, 2018, pp. 1-9.

Ma, et al., "PatternHunter: faster and more sensitive homology search" Bioinformatics, vol. 18, No. 3 (2002) pp. 440-445.

Mahieu, L., [webpage] "My (free) Ancestry.com DNA results—a comparison to FamilyTreeDNA," Genejourneys (Internet Blog), published online Mar. 6, 2012, pp. 1-3. [retrieved May 23, 2018].

Maples, et al. "RFMix: A Discriminitve Modeling Approach for Rapid and Robust Local-Ancestry Inference," American Journal of Human Genetics (AJHG) vol. 93, No. 2, Aug. 8, 2013, pp. 278-288. [retrieved Nov. 12, 2015].

Martin, et al., "Haplotype Sharing Provides Insights into Fine-Scale Population History and Disease in Finland", The American Journal of Human Genetics 102, May 3, 2018, pp. 760-775.

McCarthy, et al., "A reference panel of 64,976 haplotypes for genotype imputation" Nature genetics, 48(10), Oct. 2016, pp. 1279-1283.

McInnes, et al., "UMAP: Uniform Manifold Approximation and Projection for Dimension Reduction" arXiv preprint arXiv: 1802.03426 (2018), pp. 1-63.

Mersha, Tesfaye et al. "Self-reported race/ethnicity in the age of genomic research: its potential impact on understanding health disparities," Human Genomics, vol. 9, No. 1 (2015) pp. 1-15.

Montinaro, Francesco et al. "Unraveling the hidden ancestry of American admixed populations," Nature Communications, Mar. 24, 2015, pp. 1-7.

Montserrat, et al., "LAI-Net: Local-ancestry inference with neural networks" ICASSP 2020-2020 IEEE International Conference on Acoustics, Speech and Signal Processing (ICASSP), May 2020, pp. 1314-1318.

Moore, C., [webpage] "LivingSocial's AncestrybyDNA Offer is Not the AncestryDNA Test!" Your Genetic Genealogist (Internet Blog), published online Sep. 18, 2012, pp. 1-2. [retrieved May 23, 2018].

Moore, C., [webpage] "New Information on Ancestry.com's AncestryDNA Product," Your Genetic Genealogist (Internet Blog), published online Mar. 30, 2012, pp. 1-3. [retrieved May 23, 2018].

Moreno-Estrada, et al., "Reconstructing the Population Genetic History of the Caribbean," PLoS Genetics, 9(11), e1003925, Nov. 14, 2013, pp. 1-19.

Moreno-Estrada, et al., "The Genetics of Mexico Recapitulates Native American Substructure and Affects Biomedical Traits" Science, Jun. 13, 2014, 344(6189), pp. 1280-1285.

Naseri, et al., "Efficient Haplotype matching between a query and panel for genealogical search", Bioinformatics, 35, 2019, pp. i233-i241. <doi:10.1093/bioinformatics/btz347>.

Naseri, et al., "Personalized genealogical history inferred from biobank-scale IBD segments" bioRxiv, Dec. 20, 2019, pp. 1-27.

Naseri, et al., "RaPID: ultra-fast, powerful, and accurate detection of segments identical by descent (IBD) in biobank-scale cohorts" Genome Biology, 201:143 (2019) pp. 1-15.

Naseri, et al., "Ultra-fast Identity by Descent Detection in Biobank-Scale Cohorts using Positional Burrows-Wheeler Transform" bioRxiv, Jan. 26, 2017, pp. 1-13.

Ng, et al., "On discriminative vs. generative classifiers: A comparison of logistic regression and naive Bayes" Advances in neural information processing systems, 14:841, 2002.

Nievergeit, Caroline, et al., "Inference of human continental origin and admixture proportions using a highly discriminative ancestry informative 41-SNP panel," Investigative Genetics, vol. 4, No. 13 (2013), pp. 1-16.

Notice of Allowance, U.S. Appl. No. 13/800,683, mailed Jan. 20, 2016.

Notice of Allowance, U.S. Appl. No. 13/800,683, mailed May 3, 2016.

Notice of Allowance, U.S. Appl. No. 13/801,056, mailed May 18, 2015.

Notice of Allowance, U.S. Appl. No. 13/801,056, mailed Aug. 12, 2015.

Notice of Allowance, U.S. Appl. No. 13/801,386, mailed Jul. 24, 2017.

Notice of Allowance, U.S. Appl. No. 13/801,552, mailed Feb. 4, 2015.

Notice of Allowance, U.S. Appl. No. 13/801,552, mailed Jun. 26, 2015.

Ramstetter, et al., "Benchmarking Relatedness Inference Methods with Genome-Wide Data from Thousands of Relatives", Genetics, vol. 207, Sep. 2017, pp. 75-82.

Ramstetter, et al., "Inferring Identical-by-Descent Sharing of Sample Ancestors Promotes High-Resolution Relative Detection" The American Journal of Human Genetics 103, Jul. 5, 2018, pp. 30-44.

Ratsch, et al., "Learning Interpretable SVMs for Biological Sequence Classification" BMC Bioinformatics, Mar. 20, 2006, 7(Suppl1):S9, pp. 1-14.

Reddit.com [Webpage] "Potential Incoming Algorithm Update (Ancestry Composition v5.9)_23andme" posted by u/ Spacemutant14 (Aug. 12, 2020) pp. 1-7.

Roach JC, et al., Analysis of genetic inheritance in a family quartet by whole-genome sequencing. Science. Apr. 30, 2010;328(5978):636-9. doi: 10.1126/science.1186802. Epub Mar. 10, 2010. PMID: 20220176; PMCID: PMC3037280.

Royal, et al. "Inferring Genetic Ancestry: Opportunities, Challenges, and Implications," The American Journal of Human Genetics, vol. 86, May 14, 2010, pp. 661-673.

Sampson, et al., "Selecting SNPs to Identify Ancestry" Ann. Hum. Genet. 2011, 75(4) Jul. 2011, pp. 539-553.

Sankararaman, et al., "Estimating Local Ancestry in Admixed Populations," The American Journal of Human Genetics, vol. 82, Feb. 2008, pp. 290-303.

Sankararaman, et al., "On the inference of ancestries in admixed populations," Genome Research, Mar. 2008, vol. 18, pp. 668-675.

Scheet, et al., "A Fast and Flexible Statistical Model for Large-Scale Population Genotype Data: Applications to Inferring Missing Geno-

(56) References Cited

OTHER PUBLICATIONS types and Haplotypic Phase," The American Journal of Human Genetics, vol. 78, Apr. 2006, pp. 629-644.
Seidman, et al., "Rapid, Phase-free Detection of Long Identity by-Descent Segments Enables Effective Relationship Classification" The American Journal of Human Genetics 106, Apr. 2, 2020, pp. 453-466.
Seldin, et al., "New approaches to disease mapping in admixed populations" Nature Reviews Genetics, 12(8): Aug. 2011, pp. 523-528.
Sengupta, et al., "Polarity and Temporality of High-Resolution Y-Chromosome Distributions in India Identify Both Indigenous and Exogenous Expansions and Reveal Minor Genetic Influence of Central Asian Pastoralists," The American Journal of Human Genetics, vol. 78, Feb. 2006, pp. 202-221.
Shemirani, et al., "Rapid detection of identity-by-descent tracts for mega-scale datasets" bioRxiv, Sep. 8, 2019, pp. 1-21.
Shriver, et al., "Ethnic-Affiliation Estimation by Use of Population-Specific DNA Markers," American Journal of Human Genetics, vol. 60, 1997, pp. 957-964.
Shriver, et al., "Genetic ancestry and the Search for Personalized Genetic Histories," Nature Reviews Genetics, vol. 5, Aug. 2004, pp. 611-618.
Shriver, M.D. et al., "The Genomic Distribution of Population Substructure in Four Populations Using 8,525 Autosomal SNPs", Human Genomics, 2004, vol. 1, No. 4, pp. 274-286.
Sohn, et al. "Robust Estimation of Local Genetic Ancestry in Admixed Populations Using a Nonparametric Bayesian Approach," Genetics, vol. 191, Aug. 2012, pp. 1295-1308.
Stephens, et al., "A Comparison of Bayesian Methods for Haplotype Reconstruction from Population Genotype Data," Am. J. Hum. Genet., vol. 73, 2003, pp. 1162-1169.
Stephens, et al., "A New Statistical Method for Haplotype Reconstruction from Population Data," Am. J. Hum. Genet., vol. 68, 2001, pp. 978-989.
Stephens, et al., "Accounting for Decay of Linkage Disequilibrium in Haplotype Inference and Missing-Data Imputation," Am. J. Hum. Genet., vol. 76, 2005, pp. 449-462.
Sundquist, et al., "Effect of genetic divergence in identifying ancestral origin using HAPAA" Genome Research, vol. 18, No. 4, Apr. 2008, pp. 676-682.
Tang, et al., "Reconstructing Genetic Ancestry Blocks in Admixed Individuals," The American Journal of Human Genetics, vol. 79, No. 1, Jul. 2006, pp. 1-12.
Tang, Hua, et al., "Estimation of Individual Admixture: Analytical and Study Design Considerations", Genetic Epidemiology 28: 289-301 (2005).
The 1000 Genomes Project Consortium "A global reference for human genetic variation" Nature, 526(7571); 2015, pp. 68-74.
The International HapMap Consortium, "A haplotype map of the human genome" vol. 437, Oct. 27, 2005, pp. 1300-1320. doi:10.1038/nature04226.
The International HapMap Consortium, "A second generation human haplotype map of over 3.1 million SNPs," Nature, vol. 449, Oct. 18, 2007, pp. 851-860. <doi: 10.1038/nature06258>.
Thiele, H., et al., HaploPainter: a tool for drawing Pedigrees with complex haplotypes, vol. 21 No. 8, 2005, pp. 1730-1732.
Thompson, E. "Identity by Descent Variation in Meiosis; Across Genomes, and in Populations" Genetics, vol. 194, Jun. 2013, pp. 301-326.
Thornton, et al., "Local and Global Ancestry Inference, and Applications to Genetic Association Analysis for Admixed Populations" Genet. Epidemiol., Sep. 2014, 38(01): S5-S12.
U.S. Appl. No. 12/381,992, filed Mar. 18, 2009.
U.S. Appl. No. 13/800,683, filed Mar. 13, 2013.
U.S. Appl. No. 15/181,083, filed Jun. 13, 2016.
U.S. Appl. No. 15/181,088, filed Jun. 13, 2016.
U.S. Appl. No. 15/950,023, filed Apr. 10, 2018.
U.S. Appl. No. 16/044,364, filed Jul. 24, 2018.
U.S. Appl. No. 16/219,597, filed Dec. 13, 2018.
U.S. Appl. No. 16/226,116, filed Dec. 19, 2018.
U.S. Appl. No. 16/282,221, filed Feb. 21, 2019.
U.S. Appl. No. 16/844,758, filed Apr. 9, 2020.
U.S. Appl. No. 16/915,868, filed Jun. 29, 2020.
U.S. Appl. No. 16/946,829, filed Jul. 8, 2020.
U.S. Appl. No. 17/161,140, filed Jan. 28, 2021.
U.S. Appl. No. 17/387,940, filed Jul. 28, 2021.
U.S. Appl. No. 17/443,946, filed Jul. 28, 2021.
U.S. Appl. No. 17/444,989, filed Aug. 12, 2021.
U.S. Appl. No. 17/662,040, filed May 4, 2022.
U.S. Appl. No. 17/682,761, filed Feb. 28, 2022.
International Search Report and Written Opinion, PCT Application PCT/US2023/075521, mailed Jan. 12, 2024.
Notice of Allowance, U.S. Appl. No. 18/503,841, mailed Apr. 2, 2024.
Office Action, U.S. Appl. No. 17/444,989, mailed Jun. 7, 2023.
Office Action, U.S. Appl. No. 18/143,905, mailed Apr. 2, 2024.
Office Action, U.S. Appl. No. 18/503,841, mailed Feb. 27, 2024.
U.S. Appl. No. 17/707,790, filed Mar. 29, 2022.
Uddin, et al., "Variability of Haplotype Phase and Its Effect on Genetic Analysis," Electrical and Computer Engineering, 2008, CCECE 2008, Canadian Conference on, IEEE, 2008, pp. 000596-000600.
Underhill, et al., "Use of Y Chromosome and Mitochondrial DNA Population Structure in Tracing Human Migrations," Annu. Rev. Genet., vol. 41, 2007, pp. 539-564.
Upton et al., Review: High-Performance computing to detect epistasis in genome scale data sets, 2016, Briefings in Bioinformatics, 17(30, p. 368-379 (2016).
Vacic, V. et al., "Genome-wide mapping of IBD segments in an Ashkenazi PD cohort identifies associated haplotypes", Human Molecular Genetics, 2014, vol. 23, No. 17 pp. 4693-4702.
Van Rossum, G., "Python reference manual" Computer Science/Department of Algorithmics and Architecture, CS- R9525, Apr. 10, 1995, version 1.2, pp. 1-59.
van Rossum, G., "The Python Language Reference", Release 3.2.3, Python Software Foundation, Jun. 18, 2012, pp. 1-125.
Vanitha, et al., "Implementation of an Integrated FPGA Based Automatic Test Equipment and Test Generation for Digital Circuits," Information Communication and Embedded Systems (ICICES), 2013 International Conference on. IEEE, 2013.
Ward, J.J. et al., "Secondary Structure Prediction with Support Vector Machines", Bioinformatics, 2003, vol. 19, No. 13, pp. 1650-1655.
Williams, et al., "A rapid, accurate approach to inferring pedigrees in endogamous populations" bioRxiv, Jan. 29, 2020, pp. 1-27.
Yang, et al., "Examination of Ancestry and Ethnic Affiliation Using Highly Informative Diallelic DNA Markers: Application to Diverse and Admixed Populations and Implications for Clinical Epidemiology and Forensic Medicine," Human Genetics, vol. 118, 2005, pp. 382-392.
Yang, X. et al., "Identity-by-Descent Analysis Reveals Susceptibility Loci for Severe Acne in Chinese Han Cohort" Journal of Investigative Dermatology 139, Mar. 25, 2019, pp. 2049-2051. doi: 10.1016/j.jid.2019.03.1132.
Yoon, Byung-Jun, "Hidden Markov Models and their Applications in Biological Sequence Analysis," Current Genomics, vol. 10, 2009, pp. 402-415.
Yousef, Malik, et al., "Recursive Cluster Elimination (RCE) for Classification and Feature Selection From Gene Expression Data," BMC Bioinformatics, vol. 8, May 2007, pp. 1-12.
Yu, Haiyuan et al., "Total Ancestry Measure: quantifying the similarity in tree-like classification, with genomic applications" Bioinformatics, vol. 23, No. 16, May 31, 2007, pp. 2163-2173.
Zheng, X. and Weir, B. "Eigenanalysis of SNP data with an identity by descent interpretation" Theoretical Population Biology 107 (2016) pp. 65-76.
Zhou, et al., "A Fast and Simple Method for Detecting Identity by-Descent Segments in Large-Scale Data" The American Journal of Human Genetics 106, Apr. 2, 2020, pp. 426-437.
Zhou, Nina, et al., "Effective Selection of Informative SNPs and Classification on the HapMap Genotype Data," BMC Bioinformatics, vol. 8, No. 1, 2007, pp. 1-9.

(56) References Cited

OTHER PUBLICATIONS

Office Action, U.S. Appl. No. 16/044,364, mailed Feb. 11, 2019.
Office Action, U.S. Appl. No. 16/226,116, mailed Nov. 1, 2021.
Office Action, U.S. Appl. No. 16/240,641, mailed Nov. 19, 2021.
Office Action, U.S. Appl. No. 16/282,221, mailed Feb. 4, 2022.
Office Action, U.S. Appl. No. 16/446,465, mailed Oct. 11, 2019.
Office Action, U.S. Appl. No. 16/844,758, mailed Oct. 5, 2020.
Office Action, U.S. Appl. No. 16/844,758, mailed Feb. 2, 2021.
Office Action, U.S. Appl. No. 16/844,758, mailed Oct. 1, 2021.
Office Action, U.S. Appl. No. 16/844,758, mailed Apr. 11, 2022.
Office Action, U.S. Appl. No. 16/844,758, mailed Sep. 1, 2022.
Office Action, U.S. Appl. No. 16/915,868, mailed Oct. 20, 2020.
Office Action, U.S. Appl. No. 16/915,868, mailed Feb. 10, 2021.
Office Action, U.S. Appl. No. 16/946,829, mailed Nov. 16, 2022.
Office Action, U.S. Appl. No. 16/947,107, mailed Mar. 13, 2023.
Office Action, U.S. Appl. No. 16/947,107, mailed Aug. 17, 2023.
Office Action, U.S. Appl. No. 17/161,140, mailed Jun. 3, 2021.
Office Action, U.S. Appl. No. 17/161,140, mailed Oct. 1, 2021.
Office Action, U.S. Appl. No. 17/161,140, mailed Apr. 15, 2022.
Office Action, U.S. Appl. No. 17/249,520, mailed Jun. 1, 2021.
Office Action, U.S. Appl. No. 17/249,520, mailed Dec. 29, 2021.
Office Action, U.S. Appl. No. 17/249,520, mailed Nov. 23, 2022.
Office Action, U.S. Appl. No. 17/249,520, mailed Feb. 7, 2023.
Office Action, U.S. Appl. No. 17/387,940, mailed Jan. 24, 2022.
Office Action, U.S. Appl. No. 17/662,040, mailed Jul. 10, 2023.
Office Action, U.S. Appl. No. 17/682,761, mailed Jun. 7, 2022.
Office Action, U.S. Appl. No. 17/707,790, mailed Dec. 15, 2022.
Office Action, U.S. Appl. No. 18/157,595, mailed May 1, 2023.
Omberg, L., et al., "Inferring Genome-Wide Patterns of Admixture in Qataris Using Fifty-Five Ancestral Populations," BMC Genetics, 2012, ISSN 1471-2156, BioMed Central, Ltd., 18 pages.
Padhukasahasram, B., "Inferring ancestry from population genomic data and its applications" Front. Genet. Jul. 2014, vol. 5, Article 204, pp.
Palamara, et al., "Inference of historical migration rates via haplotype sharing" Bioinformatics, vol. 29 (2013) pp. i180-i188.
Palamara, et al., "Length Distributions of Identity by Descent Reveal Fine-Scale Demographic History" The American Journal of Human Genetics 91, Nov. 2, 2012, pp. 809-822.
Pasaniuc et al., "Highly Scalable Genotype Phasing By Entropy Minimization," Engineering in Medicine and Biology Society, 2006, EMBS'06, 28th Annual International Conference of the IEEE, 2006, 5 pages.
Pasaniuc, et al., "Inference of locus-specific ancestry in closely related populations," Bioinformatics, 25(12) Jun. 2009, pp. i213-i221.
Pathak, et al., "The Genetic Ancestry of Modern Indus Valley Populations from Northwest India" The American Journal of Human Genetics 103, Dec. 6, 2018, pp. 918-929.
Patterson, et al., "Methods for High-Density Admixture Mapping of Disease Genes," AJHG, vol. 74, No. 5, May 2004, pp. 1-33.
Patterson, et al., "Population Structure and Eigenanalysis," PLoS Genetics, vol. 2, No. 12, e190, Dec. 2006, pp. 2074-2093.
Phelps, C.I., et al. "Signal Classification by probablistic reasoning," Radio and Wireless Symposium (RWS), 2013 IEEE Year: 2013, pp. 154-156.
Phillips, C., Forensic Genetic Analysis of Bio-Geographical Ancestry, Forensic Science International: Genetics, pp. 49-65, 2015.
Phillips, et al., "Inferring Ancestral Origin Using a Single Multiplex Assay of Ancestry-Informative Marker SNPs," Forensic Science International, Genetics, vol. 1, 2007, pp. 273-280.
Pirola, et al., "A Fast and Practical Approach to Genotype Phasing and Imputation on a Pedigree with Erroneous and Incomplete Information," IEEE/ACM Transactions on Computational Biology and Bioinformatics, vol. 9, No. 6. Nov./Dec. 2012, pp. 1582-1594.
Pool, et al., "Inference of Historical Changes in Migration Rate From the Lengths of Migrant Tracts," Genetics, 181(2), Feb. 2009, pp. 711-719.
Porras-Hurtado, et al., "An overview of Structure: applications, parameter settings, and supporting software," Frontiers in Genetics, vol. 4, No. 96, May 29, 2013, pp. 1-13.
Price, et al. "Sensitive Detection of Chromosomal Segments of Distinct Ancestry in Admixed Populations," PLoS Genetics, vol. 5, No. 6, Jun. 19, 2009 (e1000519) pp. 1-18.
Price, et al., "New approaches to population stratification in genome-wide association studies" Nature Reviews Genetics, 11(7): Jun. 2010, pp. 459-463.
Pritchard, et al., "Association Mapping in Structured Populations," Am. J. Hum. Genet., vol. 67, 2000, pp. 170-181.
Pritchard, et al., "Inference of population structure using multilocus genotype data" Genetics 155, (2000) pp. 945-959.
Purcell, et al., "PLINK: a toolset for whole-genome association and population-based linkage analysis", Am. J. Hum. Genet., vol. 81, Sep. 2007, pp. 559-575.
Rabiner, L., "A Tutorial on Hidden Markov Models and Selected Applications in Speech Recognition," Proceedings of the IEEE, vol. 77, No. 2, Feb. 1989, pp. 257-286.
Ralph, et al., "The Geography of Recent Genetic Ancestry across Europe" PLoS Biol 11(5): e1001555, May 7, 2013, pp. 1-20.

\* cited by examiner

| ... | AA | AC | GC | TC | ... | ⎯502

FIG. 5A

| ... | A | C | G | T | ... | ⎯504

| ... | A | A | C | C | ... | ⎯506

FIG. 5B

|      | Afri | NAme | Ashk | EAsi | Balk | EEur | MEas | BIsl | Scan | Finl | Ocea | SAsi | Sard | Ital | Iber | Gree | Arab | WEur |
|------|------|------|------|------|------|------|------|------|------|------|------|------|------|------|------|------|------|------|
| Afri | 0.82 | 0.01 | 0.01 | 0.03 | 0.01 | 0.01 | 0.01 | 0.01 | 0.00 | 0.01 | 0.01 | 0.02 | 0.01 | 0.01 | 0.01 | 0.01 | 0.03 | 0.01 |
| NAme | 0.01 | 0.71 | 0.01 | 0.10 | 0.01 | 0.01 | 0.01 | 0.01 | 0.01 | 0.02 | 0.04 | 0.02 | 0.02 | 0.01 | 0.01 | 0.01 | 0.01 | 0.01 |
| Ashk | 0.01 | 0.03 | 0.40 | 0.03 | 0.04 | 0.03 | 0.04 | 0.02 | 0.03 | 0.05 | 0.03 | 0.03 | 0.10 | 0.02 | 0.03 | 0.05 | 0.05 | 0.02 |
| EAsi | 0.01 | 0.10 | 0.02 | 0.57 | 0.01 | 0.01 | 0.02 | 0.01 | 0.01 | 0.03 | 0.07 | 0.05 | 0.02 | 0.01 | 0.01 | 0.02 | 0.02 | 0.01 |
| Balk | 0.01 | 0.04 | 0.06 | 0.04 | 0.08 | 0.08 | 0.05 | 0.05 | 0.06 | 0.08 | 0.03 | 0.04 | 0.10 | 0.05 | 0.04 | 0.08 | 0.05 | 0.04 |
| EEur | 0.01 | 0.05 | 0.06 | 0.04 | 0.07 | 0.12 | 0.04 | 0.05 | 0.07 | 0.11 | 0.03 | 0.04 | 0.09 | 0.03 | 0.04 | 0.07 | 0.04 | 0.04 |
| MEas | 0.02 | 0.04 | 0.08 | 0.05 | 0.05 | 0.04 | 0.10 | 0.04 | 0.04 | 0.05 | 0.04 | 0.09 | 0.09 | 0.05 | 0.04 | 0.07 | 0.07 | 0.03 |
| BIsl | 0.01 | 0.04 | 0.05 | 0.03 | 0.05 | 0.06 | 0.04 | 0.10 | 0.09 | 0.10 | 0.03 | 0.04 | 0.11 | 0.04 | 0.06 | 0.06 | 0.04 | 0.05 |
| Scan | 0.01 | 0.04 | 0.05 | 0.03 | 0.05 | 0.06 | 0.04 | 0.08 | 0.12 | 0.12 | 0.03 | 0.03 | 0.10 | 0.03 | 0.05 | 0.06 | 0.04 | 0.05 |
| Finl | 0.00 | 0.05 | 0.04 | 0.05 | 0.04 | 0.06 | 0.03 | 0.04 | 0.07 | 0.31 | 0.03 | 0.03 | 0.09 | 0.02 | 0.03 | 0.05 | 0.03 | 0.03 |
| Ocea | 0.04 | 0.04 | 0.02 | 0.19 | 0.01 | 0.01 | 0.02 | 0.02 | 0.01 | 0.02 | 0.47 | 0.07 | 0.02 | 0.02 | 0.01 | 0.01 | 0.02 | 0.01 |
| SAsi | 0.02 | 0.05 | 0.05 | 0.11 | 0.04 | 0.04 | 0.06 | 0.04 | 0.03 | 0.05 | 0.05 | 0.23 | 0.06 | 0.03 | 0.03 | 0.05 | 0.04 | 0.02 |
| Sard | 0.01 | 0.03 | 0.06 | 0.04 | 0.05 | 0.04 | 0.05 | 0.06 | 0.05 | 0.06 | 0.03 | 0.04 | 0.21 | 0.05 | 0.06 | 0.06 | 0.06 | 0.04 |
| Ital | 0.02 | 0.04 | 0.07 | 0.04 | 0.05 | 0.05 | 0.06 | 0.06 | 0.05 | 0.07 | 0.03 | 0.05 | 0.11 | 0.06 | 0.06 | 0.07 | 0.06 | 0.04 |
| Iber | 0.02 | 0.04 | 0.06 | 0.04 | 0.05 | 0.06 | 0.04 | 0.05 | 0.06 | 0.08 | 0.03 | 0.04 | 0.12 | 0.05 | 0.09 | 0.06 | 0.05 | 0.05 |
| Gree | 0.02 | 0.03 | 0.07 | 0.04 | 0.06 | 0.03 | 0.06 | 0.04 | 0.05 | 0.06 | 0.03 | 0.05 | 0.11 | 0.06 | 0.05 | 0.09 | 0.06 | 0.04 |
| Arab | 0.07 | 0.03 | 0.07 | 0.05 | 0.04 | 0.06 | 0.07 | 0.04 | 0.03 | 0.04 | 0.03 | 0.06 | 0.08 | 0.05 | 0.04 | 0.06 | 0.19 | 0.03 |
| WEur | 0.01 | 0.04 | 0.06 | 0.03 | 0.05 | 0.06 | 0.04 | 0.08 | 0.09 | 0.10 | 0.03 | 0.04 | 0.11 | 0.04 | 0.06 | 0.06 | 0.04 | 0.06 |

FIG. 19

|  | Before | | | | After | | | |
|---|---|---|---|---|---|---|---|---|
|  | Unadmixed | | Admixed | | Unadmixed | | Admixed | |
|  | Recall | Prec | Recall | Prec | Recall | Prec | Recall | Prec |
| African | 0.82 | 0.83 | 0.77 | 0.70 | 1.00 | 0.99 | 0.94 | 0.93 |
| Native American | 0.71 | 0.19 | 0.64 | 0.45 | 0.99 | 1.00 | 0.90 | 0.92 |
| Ashkenazi | 0.40 | 0.57 | 0.41 | 0.32 | 0.91 | 0.98 | 0.88 | 0.92 |
| East Asian | 0.57 | 0.68 | 0.53 | 0.36 | 1.00 | 0.99 | 0.88 | 0.86 |
| Balkans | 0.08 | 0.04 | 0.08 | 0.10 | 0.71 | 0.75 | 0.29 | 0.45 |
| Eastern Europe | 0.12 | 0.16 | 0.11 | 0.13 | 0.80 | 0.75 | 0.55 | 0.47 |
| Middle East | 0.10 | 0.08 | 0.10 | 0.10 | 0.89 | 0.78 | 0.55 | 0.47 |
| British Isles | 0.10 | 0.25 | 0.10 | 0.11 | 0.96 | 0.53 | 0.68 | 0.22 |
| Scandinavia | 0.12 | 0.12 | 0.12 | 0.13 | 0.60 | 0.62 | 0.35 | 0.51 |

- Sub-Saharan Africa
  - West Africa
    - Senegal, The Gambia & Guinea
    - Sierra Leone, Libera, Ivory Coast & Ghana
    - Nigeria
    - Sudan
  - Northern East Africa
    - Ethiopia & Eritrea
    - Somalia
  - Congo & Southern East Africa
    - Congo
    - Southern East Africa
    - Biaka, Mbuti & San
- East Asia & Americas
  - Japan & Korea
    - Japan
    - Korea
  - China & Southeast Asia
    - China
    - Chinese Dai
    - Vietnam
    - Philippines & Austronesia
    - Myanmar, Thailand, Cambodia, & Indonesia
  - Northern Asia
    - Mongolia & Manchuria
    - Sibera
    - Americas
    - Melanesia
- South Asia & Central Asia
  - Northern South Asia & Central Asia
    - Central Asia
    - Northern India & Southern Pakistan
    - Bengal & Northeast India
    - Gujarat Subgroup
    - Southern Brahmin
  - Southern India & Sri Lanka
    - Southern India Other & Sri Lanka
    - Kerala
- West Asia & North Africa
  - Northern West Asia
    - Cyprus
    - Turkey
    - Causcasus, Assyria & Iran
  - Arabia, Levant & Egypt
    - Arabia
    - Levant
    - Egypt Other
    - Copt
    - Maghreb
- Europe
  - Northwest Europe
    - Britain & Ireland
    - Central & West Europe
    - Scandinavia
    - Finland
  - South Europe
    - Spain & Portugal
    - Sardinia
    - Italy
    - Balkans & Greece
    - East Europe
    - Ashkenazi Jewis

FIG. 24B

| | Precision t=0.5 | Recall t=0.5 | Precision t=0.8 | Recall t=0.8 |
|---|---|---|---|---|
| Sub-Saharan Africa | 99.3 | 99 | 99.6 | 98.6 |
|   West Africa | 99.2 | 98.4 | 99.6 | 96.8 |
|     Senegal, The Gambia & Guinea | 98.8 | 94.1 | 99.6 | 82 |
|     Sierra Leone, Liberia, Ivory Coast & Ghana | 96.5 | 87.5 | 98.8 | 74.8 |
|     Nigeria | 91.7 | 98.4 | 97.4 | 94 |
|   Northern East Africa | 98.7 | 93 | 99.4 | 90.8 |
|     Sudan | 96.1 | 85 | 97.3 | 80.1 |
|     Ethiopia & Eritrea | 96.1 | 96.8 | 98.2 | 95.1 |
|     Somalia | 99.7 | 92.3 | 99.9 | 90.9 |
|   Congo & Southern East Africa | 95.4 | 99.8 | 97.4 | 99.5 |
|     Congo | 95.7 | 99.9 | 97.9 | 99.7 |
|     Southern East Africa | 92 | 93.1 | 96.1 | 85.1 |
|   Biaka, Mbuti & San | 99.9 | 82.7 | 100 | 78.2 |
| East Asia & Americas | 98.8 | 99.8 | 99.3 | 99.7 |
|   Japan & Korea | 99.5 | 99.9 | 99.7 | 99.7 |
|     Japan | 99.9 | 99.6 | 100 | 99.1 |
|     Korea | 98.7 | 99.8 | 99.3 | 99.5 |
|   China & Southeast Asia | 99.2 | 99.7 | 99.5 | 99.3 |
|     China | 96.2 | 99.4 | 97.7 | 97.9 |
|     Chinese Dai | 94.4 | 98.5 | 98 | 96.6 |
|     Vietnam | 98.7 | 97 | 100 | 93.4 |
|     Philippines & Austronesia | 94.9 | 95 | 96.1 | 91.7 |
|     Myanmar, Thailand, Cambodia, & Indonesia | 94.1 | 62.6 | 94.7 | 49.5 |
|   Northern Asia | 63.3 | 81.8 | 78 | 79.5 |
|     Mongolia & Manchuria | 41.2 | 68.5 | 57.9 | 63.3 |
|     Siberia | 98.2 | 90.5 | 99.8 | 86.2 |
|   Americas | 99.5 | 95.3 | 99.9 | 90.5 |
| Melanesia | 99.6 | 96.5 | 99.7 | 93.5 |
| South Asia & Central Asia | 99.4 | 97 | 99.7 | 96 |
|   Northern South Asia & Central Asia | 95 | 92.9 | 97.6 | 89.8 |
|     Central Asia | 94.9 | 49.8 | 97.9 | 36.1 |
|     Northern India & Southern Pakistan | 84.7 | 88.2 | 91.5 | 80.3 |
|     Bengal & Northeast India | 90.9 | 98.9 | 95.8 | 97.6 |
|     Gujarati Patel | 99.6 | 99.5 | 100 | 99.1 |
|   Southern Brahmin | 97.4 | 80.8 | 99 | 72.1 |
|   Southern India & Sri Lanka | 92.1 | 95.9 | 95.9 | 91.7 |
|     Southern India Other & Sri Lanka | 76.4 | 95.1 | 82.6 | 90.4 |
|     Kerala | 98.2 | 69.7 | 98.9 | 66.7 |
| West Asia & North Africa | 98.1 | 92.6 | 99 | 89.4 |
|   Northern West Asia | 84.8 | 89.7 | 89.9 | 85.3 |
|     Cyprus | 97.4 | 90.7 | 98.7 | 85.7 |
|     Turkey | 87.5 | 71.2 | 94.1 | 57.8 |
|     Caucasus, Assyria & Iran | 72.6 | 91.1 | 83.7 | 85.6 |
|   Arabia, Levant & Egypt | 97.6 | 81.2 | 98.3 | 75 |
|     Arabia | 97.4 | 69.5 | 98.9 | 62.5 |
|     Levant | 96.5 | 66.7 | 98.2 | 55.9 |
|     Egypt Other | 76.7 | 89 | 87.1 | 85.3 |
|     Copt | 98.7 | 86.7 | 99.8 | 83.4 |
|   Maghreb | 99.3 | 89.6 | 99.7 | 84.4 |
| Europe | 97.6 | 99.7 | 98.3 | 99.4 |
|   Northwest Europe | 94.4 | 98.1 | 96.9 | 95.8 |
|     Britain & Ireland | 89.8 | 95 | 96.2 | 84 |
|     Central & West Europe | 80.5 | 86 | 91.1 | 66.4 |
|     Scandinavia | 97.3 | 83.5 | 99.2 | 67.2 |
|     Finland | 96 | 95.8 | 97.5 | 92.4 |
|   South Europe | 91 | 88.8 | 93.5 | 81.4 |
|     Spain & Portugal | 95.8 | 94.3 | 97.7 | 88.8 |
|     Sardinia | 92.8 | 98.3 | 94.6 | 96 |
|     Italy | 82.6 | 85.5 | 89.1 | 77.1 |
|     Balkans & Greece | 91.7 | 80 | 93.9 | 69 |
|   East Europe | 86.4 | 90.8 | 92.4 | 83.7 |
| Ashkenazi Jewish | 99.3 | 98.9 | 99.4 | 98.4 |

FIG. 24C

| Population | African American Change from Multi-Module to Single Module | African American Multi-Module | Ashkenazi Change from Multi-Module to Single Module | Ashkenazi Multi-Module |
|---|---|---|---|---|
| Root | -0.6 | 1 | 0.1 | 0 |
| Sub-Saharan Africa | -2.2 | 3 | 0 | 0 |
| West Africa | -0.3 | 8 | 0 | 0 |
| Senegal, The Gambia & Guinea | -0.6 | 5 | 0 | 0 |
| Sierra Leone, Liberia, Ivory Coast & Ghana | 0.1 | 17 | 0 | 0 |
| Nigeria | 3.6 | 25 | 0 | 0 |
| Northern East Africa | 0 | 0 | 0 | 0 |
| Sudan | 0 | 0 | 0 | 0 |
| Ethiopia & Eritrea | 0 | 1 | 0 | 0 |
| Somalia | 0 | 0 | 0 | 0 |
| Congo & Southern East Africa | -1 | 2 | 0 | 0 |
| Congo | 0.9 | 7 | 0 | 0 |
| Southern East Africa | -0.2 | 1 | 0 | 0 |
| Biaka, Mbuti & San | -0.1 | 0 | 0 | 0 |
| East Asia & Americas | 0 | 0 | 0 | 0 |
| Japan & Korea | 0 | 0 | 0 | 0 |
| Japan | 0.1 | 0 | 0 | 0 |
| Korea | 0 | 0 | 0 | 0 |
| China & Southeast Asia | 0 | 0 | 0 | 0 |
| China | 0.1 | 0 | 0 | 0 |
| Chinese Dai | 0.1 | 0 | 0 | 0 |
| Vietnam | 0 | 0 | 0 | 0 |
| Philippines & Austronesia | 0 | 0 | 0 | 0 |
| Myanmar, Thailand, Cambodia, & Indonesia | 0 | 0 | 0 | 0 |
| Northern Asia | 0 | 0 | 0 | 0 |
| Mongolia & Manchuria | 0 | 0 | 0 | 0 |
| Siberia | 0 | 0 | 0 | 0 |
| Americas | 0 | 1 | 0 | 0 |
| Melanesia | 0 | 0 | 0 | 0 |
| South Asia & Central Asia | 0 | 0 | 0 | 0 |
| Northern South Asia & Central Asia | 0 | 0 | 0 | 0 |
| Central Asia | 0 | 0 | 0 | 0 |
| Northern India & Southern Pakistan | 0 | 0 | 0 | 0 |
| Bengal & Northeast India | 0 | 0 | 0 | 0 |
| Gujarati Patel | 0 | 0 | 0 | 0 |
| Southern Brahmin | 0 | 0 | 0 | 0 |
| Southern India & Sri Lanka | 0 | 0 | 0 | 0 |
| Southern India Other & Sri Lanka | 0 | 0 | 0 | 0 |
| Kerala | 0 | 0 | 0 | 0 |
| West Asia & North Africa | -0.2 | 0 | -0.1 | 0 |
| Northern West Asia | 0 | 0 | 0 | 0 |
| Cyprus | 0 | 0 | 0 | 0 |
| Turkey | 0 | 0 | 0 | 0 |
| Caucasus, Assyria & Iran | 0 | 0 | 0.1 | 0 |
| Arabia, Levant & Egypt | 0.2 | 0 | 0 | 0 |
| Arabia | 0.1 | 0 | 0 | 0 |
| Levant | -0.1 | 0 | 0 | 0 |
| Egypt Other | 0.2 | 0 | 0 | 0 |
| Copt | 0 | 0 | 0 | 0 |
| Maghreb | 0 | 1 | 0 | 0 |
| Europe | -1.3 | 2 | 0.3 | 0 |
| Northwest Europe | -3.8 | 6 | -0.1 | 0 |
| Britain & Ireland | 3.9 | 9 | 0.1 | 0 |
| Central & West Europe | 0.8 | 5 | 0.1 | 0 |
| Scandinavia | 0.2 | 1 | 0 | 0 |
| Finland | 0 | 0 | 0 | 0 |
| South Europe | 0.6 | 1 | 0 | 0 |
| Spain & Portugal | 0.6 | 1 | 0 | 0 |
| Sardinia | 0 | 0 | 0 | 0 |
| Italy | 0.4 | 0 | 0.1 | 0 |
| Balkans & Greece | 0 | 0 | 0 | 0 |
| East Europe | 0.1 | 0 | 0.1 | 0 |
| Ashkenazi Jewish | 0 | 0 | 0 | 99 |

FIG. 24D

| Population | East Asian Change from Multi-Module to Single Module | East Asian Multi-Module | Latino Change from Multi-Module to Single Module | Latino Multi-Module |
|---|---|---|---|---|
| Root | 0.1 | 0 | 4.7 | 5 |
| Sub-Saharan Africa | 0 | 0 | -0.4 | 1 |
| West Africa | 0 | 0 | -0.1 | 1 |
| Senegal, The Gambia & Guinea | 0 | 0 | 0 | 1 |
| Sierra Leone, Liberia, Ivory Coast & Ghana | 0 | 0 | 0.1 | 0 |
| Nigeria | 0 | 0 | 0.3 | 1 |
| Northern East Africa | 0 | 0 | 0 | 0 |
| Sudan | 0 | 0 | 0 | 0 |
| Ethiopia & Eritrea | 0 | 0 | 0 | 0 |
| Somalia | 0 | 0 | 0 | 0 |
| Congo & Southern East Africa | 0 | 0 | -0.2 | 0 |
| Congo | 0 | 0 | 0.3 | 1 |
| Southern East Africa | 0 | 0 | 0 | 0 |
| Biaka, Mbuti & San | 0 | 0 | 0 | 0 |
| East Asia & Americas | -0.3 | 1 | 1.3 | 2 |
| Japan & Korea | -0.2 | 0 | 0 | 0 |
| Japan | 0.8 | 9 | 0 | 0 |
| Korea | -2.6 | 14 | 0 | 0 |
| China & Southeast Asia | -0.2 | 3 | 0.2 | 0 |
| China | 1.2 | 49 | 0.1 | 0 |
| Chinese Dai | 1.1 | 2 | 0 | 0 |
| Vietnam | 0.2 | 9 | 0.1 | 0 |
| Philippines & Austronesia | 0 | 11 | 0.1 | 1 |
| Myanmar, Thailand, Cambodia, & Indonesia | 0 | 2 | 0 | 0 |
| Northern Asia | 0 | 0 | 0 | 0 |
| Mongolia & Manchuria | 0.6 | 0 | 0.1 | 0 |
| Siberia | 0 | 0 | 0 | 0 |
| Americas | 0 | 0 | 1.3 | 20 |
| Melanesia | 0 | 0 | 0 | 0 |
| South Asia & Central Asia | -0.1 | 0 | -0.1 | 0 |
| Northern South Asia & Central Asia | -0.1 | 0 | 0 | 0 |
| Central Asia | 0 | 0 | 0 | 0 |
| Northern India & Southern Pakistan | 0 | 0 | 0 | 0 |
| Bengal & Northeast India | 0 | 0 | 0 | 0 |
| Gujarati Patel | 0 | 0 | 0 | 0 |
| Southern Brahmin | 0 | 0 | 0 | 0 |
| Southern India & Sri Lanka | 0 | 0 | 0 | 0 |
| Southern India Other & Sri Lanka | 0 | 0 | 0 | 0 |
| Kerala | 0 | 0 | 0 | 0 |
| West Asia & North Africa | 0 | 0 | -0.8 | 1 |
| Northern West Asia | 0 | 0 | 0 | 0 |
| Cyprus | 0 | 0 | 0.1 | 0 |
| Turkey | 0 | 0 | 0 | 0 |
| Caucasus, Assyria & Iran | 0 | 0 | 0.2 | 0 |
| Arabia, Levant & Egypt | 0 | 0 | 0.1 | 0 |
| Arabia | 0 | 0 | 0 | 0 |
| Levant | 0 | 0 | 0.1 | 0 |
| Egypt Other | 0 | 0 | 0.1 | 0 |
| Copt | 0 | 0 | 0.1 | 0 |
| Maghreb | 0 | 0 | 0.2 | 1 |
| Europe | 0 | 0 | 2.4 | 3 |
| Northwest Europe | 0 | 0 | -2.2 | 5 |
| Britain & Ireland | 0 | 0 | 2.4 | 12 |
| Central & West Europe | 0 | 0 | 0.3 | 7 |
| Scandinavia | 0 | 0 | 0.1 | 1 |
| Finland | 0 | 0 | 0 | 0 |
| South Europe | 0 | 0 | 5.9 | 8 |
| Spain & Portugal | 0 | 0 | 10.6 | 27 |
| Sardinia | 0 | 0 | 0 | 0 |
| Italy | 0 | 0 | 1 | 2 |
| Balkans & Greece | 0 | 0 | 0.1 | 0 |
| East Europe | 0 | 0 | 0.2 | 1 |
| Ashkenaz Jewish | 0 | 0 | 0.2 | 1 |

FIG. 24E

| Population | Middle-Eastern Change from Multi-Module to Single Module | Middle-Eastern Multi-Module | North European Change from Multi-Module to Single Module | North European Multi-Module |
|---|---|---|---|---|
| Root | -0.4 | 0 | -0.1 | 0 |
| Sub-Saharan Africa | 0 | 0 | 0 | 0 |
| West Africa | 0 | 0 | 0 | 0 |
| Senegal, The Gambia & Guinea | 0 | 0 | 0 | 0 |
| Sierra Leone, Liberia, Ivory Coast & Ghana | 0 | 0 | 0 | 0 |
| Nigeria | 0 | 0 | 0 | 0 |
| Northern East Africa | 0 | 0 | 0 | 0 |
| Sudan | 0.1 | 0 | 0 | 0 |
| Ethiopia & Eritrea | 0 | 0 | 0 | 0 |
| Somalia | 0 | 0 | 0 | 0 |
| Congo & Southern East Africa | 0 | 0 | 0 | 0 |
| Congo | 0 | 0 | 0 | 0 |
| Southern East Africa | 0 | 0 | 0 | 0 |
| Biaka, Mbuti & San | 0 | 0 | 0 | 0 |
| East Asia & Americas | 0 | 0 | 0 | 0 |
| Japan & Korea | 0 | 0 | 0 | 0 |
| Japan | 0 | 0 | 0 | 0 |
| Korea | 0 | 0 | 0 | 0 |
| China & Southeast Asia | 0 | 0 | 0 | 0 |
| China | 0 | 0 | 0 | 0 |
| Chinese Dai | 0 | 0 | 0 | 0 |
| Vietnam | 0 | 0 | 0 | 0 |
| Philippines & Austronesia | 0 | 0 | 0 | 0 |
| Myanmar, Thailand, Cambodia, & Indonesia | 0 | 0 | 0 | 0 |
| Northern Asia | 0 | 0 | 0 | 0 |
| Mongolia & Manchuria | 0 | 0 | 0 | 0 |
| Siberia | 0 | 0 | 0 | 0 |
| Americas | 0 | 0 | 0 | 0 |
| Melanesia | 0 | 0 | 0 | 0 |
| South Asia & Central Asia | -0.1 | 0 | 0 | 0 |
| Northern South Asia & Central Asia | -0.1 | 0 | 0 | 0 |
| Central Asia | 0.1 | 0 | 0 | 0 |
| Northern India & Southern Pakistan | 0 | 0 | 0 | 0 |
| Bengal & Northeast India | 0 | 0 | 0 | 0 |
| Gujarati Patel | 0 | 0 | 0 | 0 |
| Southern Brahmin | 0 | 0 | 0 | 0 |
| Southern India & Sri Lanka | 0 | 0 | 0 | 0 |
| Southern India Other & Sri Lanka | 0 | 0 | 0 | 0 |
| Kerala | 0 | 0 | 0 | 0 |
| West Asia & North Africa | -1.8 | 2 | -0.1 | 0 |
| Northern West Asia | .5 | 5 | 0 | 0 |
| Cyprus | 0.3 | 3 | 0 | 0 |
| Turkey | -2.1 | 5 | 0 | 0 |
| Caucasus, Assyria & Iran | 10.2 | 40 | 0 | 0 |
| Arabia, Levant & Egypt | -3.7 | 5 | 0 | 0 |
| Arabia | 0.1 | 6 | 0 | 0 |
| Levant | 1.2 | 21 | 0 | 0 |
| Egypt Other | 0.7 | 3 | 0 | 0 |
| Copt | 0 | 3 | 0 | 0 |
| Maghreb | -0.2 | 2 | 0 | 0 |
| Europe | 0 | 0 | -1.2 | 1 |
| Northwest Europe | 0 | 0 | -.9 | 14 |
| Britain & Ireland | 0 | 0 | 5.5 | 49 |
| Central & West Europe | 0 | 0 | 4.6 | 26 |
| Scandinavia | 0 | 0 | 0.2 | 6 |
| Finland | 0 | 0 | 0 | 0 |
| South Europe | -0.4 | 0 | -0.5 | 1 |
| Spain & Portugal | 0 | 0 | 0.2 | 0 |
| Sardinia | 0 | 0 | 0.1 | 0 |
| Italy | -0.2 | 1 | 0.1 | 0 |
| Balkans & Greece | 0 | 0 | 0 | 0 |
| East Europe | 0.1 | 0 | 0 | 1 |
| Ashkenazi Jewish | 0.1 | 0 | 0 | 0 |

FIG. 24F

| Population | Other - Change from Multi-Module to Single Module | Other - Multi-Module | South Asian - Change from Multi-Module to Single Module | South Asian - Multi-Module |
|---|---|---|---|---|
| Root | -0.9 | 1 | -0.4 | 0 |
| Sub-Saharan Africa | -0.1 | 0 | 0 | 0 |
| West Africa | -0.1 | 0 | 0 | 0 |
| Senegal, The Gambia & Guinea | 0 | 0 | 0 | 0 |
| Sierra Leone, Liberia, Ivory Coast & Ghana | 0.1 | 0 | 0 | 0 |
| Nigeria | 0.1 | 0 | 0 | 0 |
| Northern East Africa | 0 | 0 | 0 | 0 |
| Sudan | 0 | 0 | 0 | 0 |
| Ethiopia & Eritrea | 0 | 0 | 0 | 0 |
| Somalia | 0 | 0 | 0 | 0 |
| Congo & Southern East Africa | 0 | 0 | 0 | 0 |
| Congo | 0.1 | 0 | 0 | 0 |
| Southern East Africa | 0 | 0 | 0 | 0 |
| Biaka, Mbuti & San | 0 | 0 | 0 | 0 |
| East Asia & Americas | -0.5 | 1 | 0 | 0 |
| Japan & Korea | -0.3 | 0 | 0 | 0 |
| Japan | 0.1 | 5 | 0 | 0 |
| Korea | 0.3 | 2 | 0 | 0 |
| China & Southeast Asia | -1.7 | 2 | 0 | 0 |
| China | 1.3 | 3 | 0 | 0 |
| Chinese Dai | 0.1 | 0 | 0 | 0 |
| Vietnam | 0.2 | 1 | 0 | 0 |
| Philippines & Austronesia | 0.4 | 7 | 0 | 0 |
| Myanmar, Thailand, Cambodia, & Indonesia | -0.1 | 2 | 0 | 0 |
| Northern Asia | 0 | 0 | 0 | 0 |
| Mongolia & Manchuria | 0.8 | 1 | 0 | 0 |
| Siberia | -0.1 | 0 | 0 | 0 |
| Americas | 0 | 0 | 0 | 0 |
| Melanesia | 0 | 0 | 0 | 0 |
| South Asia & Central Asia | -0.4 | 0 | -4.9 | 5 |
| Northern South Asia & Central Asia | -0.5 | 1 | -5.6 | 6 |
| Central Asia | -0.5 | 2 | -0.1 | 1 |
| Northern India & Southern Pakistan | 0.5 | 1 | 6.5 | 42 |
| Bengal & Northeast India | 0.2 | 1 | 1.3 | 10 |
| Gujarati Patel | 0 | 0 | 0.2 | 4 |
| Southern Brahmin | 0 | 0 | 1.2 | 10 |
| Southern India & Sri Lanka | -0.1 | 0 | -1.8 | 2 |
| Southern India Other & Sri Lanka | 0.4 | 1 | 3 | 16 |
| Kerala | 0 | 0 | 0.6 | 5 |
| West Asia & North Africa | -0.8 | 1 | -0.1 | 0 |
| Northern West Asia | -1.1 | 1 | 0 | 0 |
| Cyprus | 0.1 | 1 | 0 | 0 |
| Turkey | 0.1 | 2 | 0 | 0 |
| Caucasus, Assyria & Iran | 2.1 | 4 | 0.1 | 0 |
| Arabia, Levant & Egypt | 0.5 | 1 | 0 | 0 |
| Arabia | 0.1 | 0 | 0 | 0 |
| Levant | 0.6 | 3 | 0 | 0 |
| Egypt Other | 0.2 | 0 | 0 | 0 |
| Copt | 0.1 | 0 | 0 | 0 |
| Maghreb | 0.1 | 1 | 0 | 0 |
| Europe | -2 | 2 | 0 | 0 |
| Northwest Europe | -4.2 | 6 | 0 | 0 |
| Britain & Ireland | 2.4 | 14 | 0 | 0 |
| Central & West Europe | 3.1 | 9 | 0 | 0 |
| Scandinavia | 0.2 | 2 | 0 | 0 |
| Finland | 0.1 | 0 | 0 | 0 |
| South Europe | -1.8 | 2 | 0 | 0 |
| Spain & Portugal | 0.7 | 2 | 0 | 0 |
| Sardinia | 0 | 0 | 0 | 0 |
| Italy | 0.8 | 6 | 0 | 0 |
| Balkans & Greece | 0 | 2 | 0 | 0 |
| East Europe | 0.6 | 3 | 0 | 0 |
| Ashkenazi Jewish | 0 | 3 | 0 | 0 |

FIG. 24G

| Population | South European Change from Multi-Module to Single Module | Multi-Module |
|---|---|---|
| Root | -0.6 | 1 |
| Sub-Saharan Africa | 0 | 0 |
| West Africa | 0 | 0 |
|   Senegal, The Gambia & Guinea | 0 | 0 |
|   Sierra Leone, Liberia, Ivory Coast & Ghana | 0 | 0 |
|   Nigeria | 0 | 0 |
| Northern East Africa | 0 | 0 |
|   Sudan | 0 | 0 |
|   Ethiopia & Eritrea | 0 | 0 |
|   Somalia | 0 | 0 |
| Congo & Southern East Africa | 0 | 0 |
|   Congo | 0 | 0 |
|   Southern East Africa | 0 | 0 |
| Biaka, Mbuti & San | 0 | 0 |
| East Asia & Americas | 0 | 0 |
| Japan & Korea | 0 | 0 |
|   Japan | 0 | 0 |
|   Korea | 0 | 0 |
| China & Southeast Asia | 0 | 0 |
|   China | 0 | 0 |
|   Chinese Dai | 0 | 0 |
|   Vietnam | 0 | 0 |
|   Philippines & Austronesia | 0 | 0 |
|   Myanmar, Thailand, Cambodia, & Indonesia | 0 | 0 |
| Northern Asia | 0 | 0 |
|   Mongolia & Manchuria | 0 | 0 |
|   Siberia | 0 | 0 |
|   Americas | 0 | 0 |
| Melanesia | 0 | 0 |
| South Asia & Central Asia | 0 | 0 |
| Northern South Asia & Central Asia | 0 | 0 |
|   Central Asia | 0 | 0 |
|   Northern India & Southern Pakistan | 0 | 0 |
|   Bengal & Northeast India | 0 | 0 |
|   Gujarati Patel | 0 | 0 |
|   Southern Brahmin | 0 | 0 |
| Southern India & Sri Lanka | 0 | 0 |
|   Southern India Other & Sri Lanka | 0 | 0 |
|   Kerala | 0 | 0 |
| West Asia & North Africa | -1.7 | 3 |
| Northern West Asia | -1 | 2 |
|   Cyprus | 0.4 | 0 |
|   Turkey | -0.3 | 1 |
|   Caucasus, Assyria & Iran | 1.4 | 0 |
| Arabia, Levant & Egypt | -0.4 | 1 |
|   Arabia | 0 | 0 |
|   Levant | 0.3 | 0 |
|   Egypt Other | 0.2 | 0 |
|   Copt | 0.1 | 0 |
| Maghreb | 0.1 | 0 |
| Europe | 1.6 | 2 |
| Northwest Europe | 1.1 | 1 |
|   Britain & Ireland | -0.4 | 1 |
|   Central & West Europe | -0.9 | 1 |
|   Scandinavia | 0 | 0 |
|   Finland | 0 | 0 |
| South Europe | 7 | 8 |
|   Spain & Portugal | 3.5 | 15 |
|   Sardinia | 0.1 | 0 |
|   Italy | 7.9 | 44 |
|   Balkans & Greece | 2.1 | 18 |
| East Europe | -1 | 2 |
| Ashkenazi Jewish | 0 | 0 |

ANCESTRY COMPOSITION DETERMINATION

CROSS-REFERENCE TO RELATED APPLICATION

This application is a continuation of and claims priority to U.S. patent application Ser. No. 17/444,989, filed Aug. 12, 2021, which is hereby incorporated by reference in its entirety.

BACKGROUND

Ancestry deconvolution refers to identifying the ancestral origin of chromosomal segments in individuals. Ancestry deconvolution in admixed individuals (i.e., individuals whose ancestors such as grandparents are from different regions) is straightforward when the ancestral populations considered are sufficiently distinct (e.g., one grandparent is from Europe and another from Asia). To date, however, existing approaches are typically ineffective at distinguishing between closely related populations (e.g., within Europe). Moreover, due to their computational complexity, most existing methods for ancestry deconvolution are unsuitable for application in large-scale settings, where the reference panels used contain thousands of individuals.

BRIEF DESCRIPTION OF THE DRAWINGS

Various embodiments of the invention are disclosed in the following detailed description and the accompanying drawings.

FIG. 5A illustrates an example of a section of unphased genotype data.

FIG. 5B illustrates an example of two sets of phased genotype data.

FIG. 19 is an example data table displaying the emission parameters.

FIG. 21 is a table comparing the predictive accuracies of ancestry assignments with and without error correction.

FIG. 24A presents a population hierarchy that may be used for determining ancestry composition.

FIG. 24B presents a table showing precision and recall results for a single smoother module process for the ancestries listed in FIG. 24A.

FIGS. 24C-G are tables comparing the results of a single smoother module process and a multiple module process for different computed ethnicities.

FIGS. 32 and 33 are diagrams illustrating embodiments of a chromosome-specific view.

DETAILED DESCRIPTION

Figure 1:
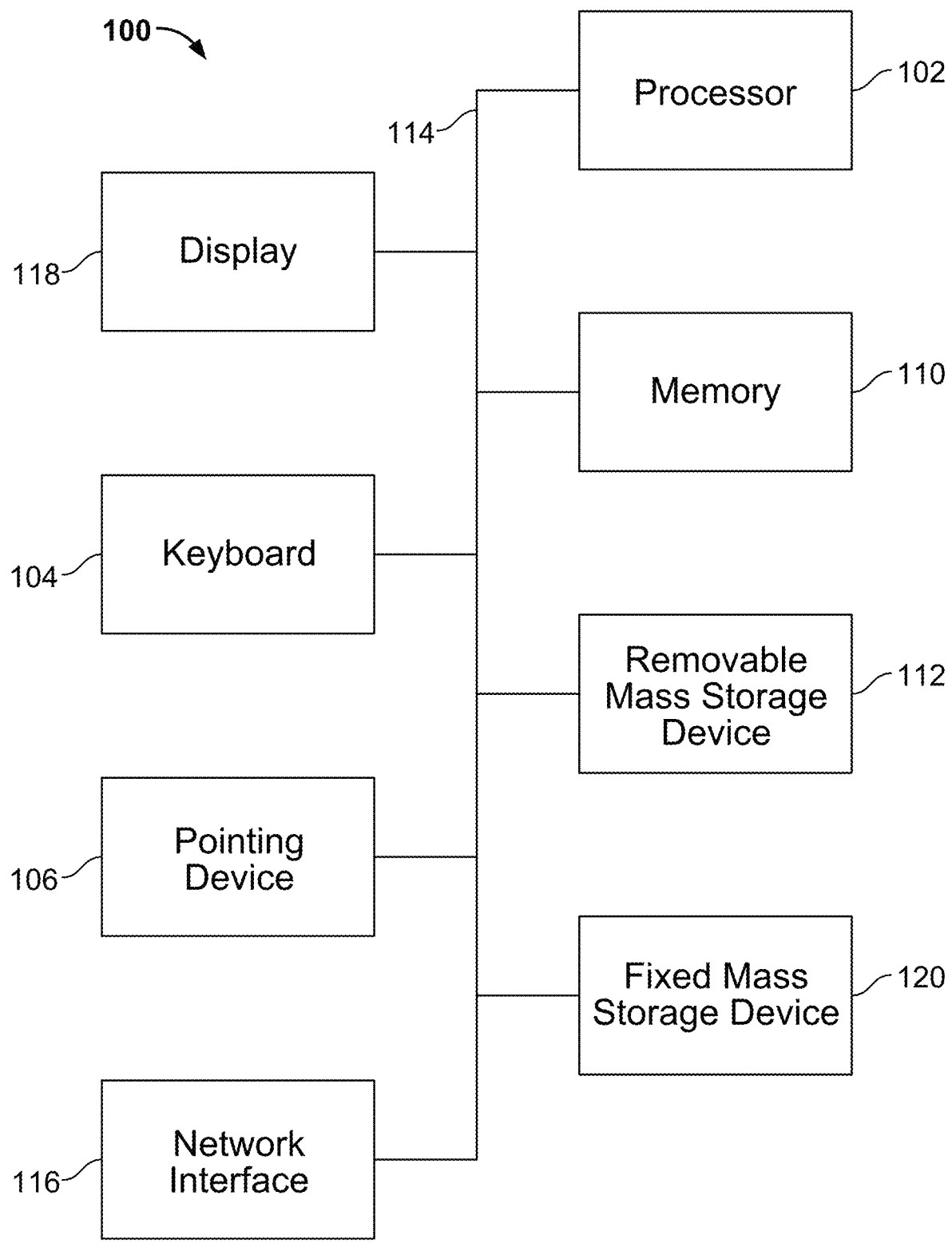
FIG. 1 is a functional diagram illustrating a programmed computer system for performing the pipelined ancestry prediction process in accordance with some embodiments.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A pipelined ancestry deconvolution process to predict an individual's ancestry based on genetic information is disclosed. Unphased genotype data associated with the individual's chromosomes is received and phased to generate phased haplotype data. In some embodiments, dynamic programming that does not require the unphased genotype data to be included in the reference data is implemented to facilitate phasing. The phased data is divided into segments, which are classified as being associated with specific ancestries. The classification is performed using a learning machine in some embodiments. The classification output undergoes an error correction process to reduce noise and correct for any phasing errors (also referred to as switch errors) and/or correlated classification errors. The error-corrected output is optionally recalibrated, and ancestry labels are optionally clustered according to a geographical hierarchy to be displayed to the user.

In some embodiments, genotype data comprising gene sequences and/or genetic markers is used to represent an individual's genome. Examples of such genetic markers include Single Nucleotide Polymorphisms (SNPs), which are points along the genome, each corresponding to two or more common variations; Short Tandem Repeats (STRs), which are repeated patterns of two or more repeated nucleotide sequences adjacent to each other; and Copy-Number Variants (CNVs), which include longer sequences of deoxyribonucleic acid (DNA) that could be present in varying numbers in different individuals. Although SNP-based genotype data is described extensively below for purposes of illustration, the technique is also applicable to other types of genotype data such as STRs and CNVs. As used herein, a haplotype refers to DNA on a single chromosome of a chromosome pair. Haplotype data representing a haplotype can be expressed as a set of markers (e.g., SNPs, STRs, CNVs, etc.) or a full DNA sequence set.

FIG. 1 is a functional diagram illustrating a programmed computer system for performing the pipelined ancestry prediction process in accordance with some embodiments. Computer system 100, which includes various subsystems as described below, includes at least one microprocessor subsystem (also referred to as a processor or a central processing unit (CPU)) 102. For example, processor 102 can be implemented by a single-chip processor or by multiple processors. In some embodiments, processor 102 is a general purpose digital processor that controls the operation of the computer system 100. Using instructions retrieved from memory 110, the processor 102 controls the reception and manipulation of input data, and the output and display of data on output devices (e.g., display 118). In some embodiments, processor 102 includes and/or is used to provide phasing, local classification, error correction, recalibration, and/or label clustering as described below.

Processor 102 is coupled bi-directionally with memory 110, which can include a first primary storage, typically a random access memory (RAM), and a second primary storage area, typically a read-only memory (ROM). As is well known in the art, primary storage can be used as a general storage area and as scratch-pad memory, and can also be used to store input data and processed data. Primary storage can also store programming instructions and data, in the form of data objects and text objects, in addition to other data and instructions for processes operating on processor 102. Also as is well known in the art, primary storage typically includes basic operating instructions, program code, data, and objects used by the processor 102 to perform its functions (e.g., programmed instructions). For example, memory 110 can include any suitable computer-readable storage media, described below, depending on whether, for example, data access needs to be bi-directional or uni-directional. For example, processor 102 can also directly and very rapidly retrieve and store frequently needed data in a cache memory (not shown).

A removable mass storage device 112 provides additional data storage capacity for the computer system 100, and is coupled either bi-directionally (read/write) or uni-directionally (read only) to processor 102. For example, storage 112 can also include computer-readable media such as magnetic tape, flash memory, PC-CARDS, portable mass storage devices, holographic storage devices, and other storage devices. A fixed mass storage 120 can also, for example, provide additional data storage capacity. The most common example of mass storage 120 is a hard disk drive. Mass storage 112, 120 generally store additional programming instructions, data, and the like that typically are not in active use by the processor 102. It will be appreciated that the information retained within mass storage 112 and 120 can be incorporated, if needed, in standard fashion as part of memory 110 (e.g., RAM) as virtual memory.

In addition to providing processor 102 access to storage subsystems, bus 114 can also be used to provide access to other subsystems and devices. As shown, these can include a display monitor 118, a network interface 116, a keyboard 104, and a pointing device 106, as well as an auxiliary input/output device interface, a sound card, speakers, and other subsystems as needed. For example, the pointing device 106 can be a mouse, stylus, track ball, or tablet, and is useful for interacting with a graphical user interface.

The network interface 116 allows processor 102 to be coupled to another computer, computer network, or telecommunications network using a network connection as shown. For example, through the network interface 116, the processor 102 can receive information (e.g., data objects or program instructions) from another network or output information to another network in the course of performing method/process steps. Information, often represented as a sequence of instructions to be executed on a processor, can be received from and outputted to another network. An interface card or similar device and appropriate software implemented by (e.g., executed/performed on) processor 102 can be used to connect the computer system 100 to an external network and transfer data according to standard protocols. For example, various process embodiments disclosed herein can be executed on processor 102, or can be performed across a network such as the Internet, intranet networks, or local area networks, in conjunction with a remote processor that shares a portion of the processing. Additional mass storage devices (not shown) can also be connected to processor 102 through network interface 116.

An auxiliary I/O device interface (not shown) can be used in conjunction with computer system 100. The auxiliary I/O device interface can include general and customized interfaces that allow the processor 102 to send and, more typically, receive data from other devices such as microphones, touch-sensitive displays, transducer card readers, tape readers, voice or handwriting recognizers, biometrics readers, cameras, portable mass storage devices, and other computers.

In addition, various embodiments disclosed herein further relate to computer storage products with a computer readable medium that includes program code for performing various computer-implemented operations. The computer-readable medium is any data storage device that can store data which can thereafter be read by a computer system. Examples of computer-readable media include, but are not limited to, all the media mentioned above: magnetic media such as hard disks, floppy disks, and magnetic tape; optical media such as CD-ROM disks; magneto-optical media such as optical disks; and specially configured hardware devices such as application-specific integrated circuits (ASICs), programmable logic devices (PLDs), and ROM and RAM devices. Examples of program code include both machine code, as produced, for example, by a compiler, or files containing higher level code (e.g., script) that can be executed using an interpreter.

The computer system shown in FIG. 1 is but an example of a computer system suitable for use with the various embodiments disclosed herein. Other computer systems suitable for such use can include additional or fewer subsystems. In addition, bus 114 is illustrative of any interconnection scheme serving to link the subsystems. Other computer architectures having different configurations of subsystems can also be utilized.

Figure 2:
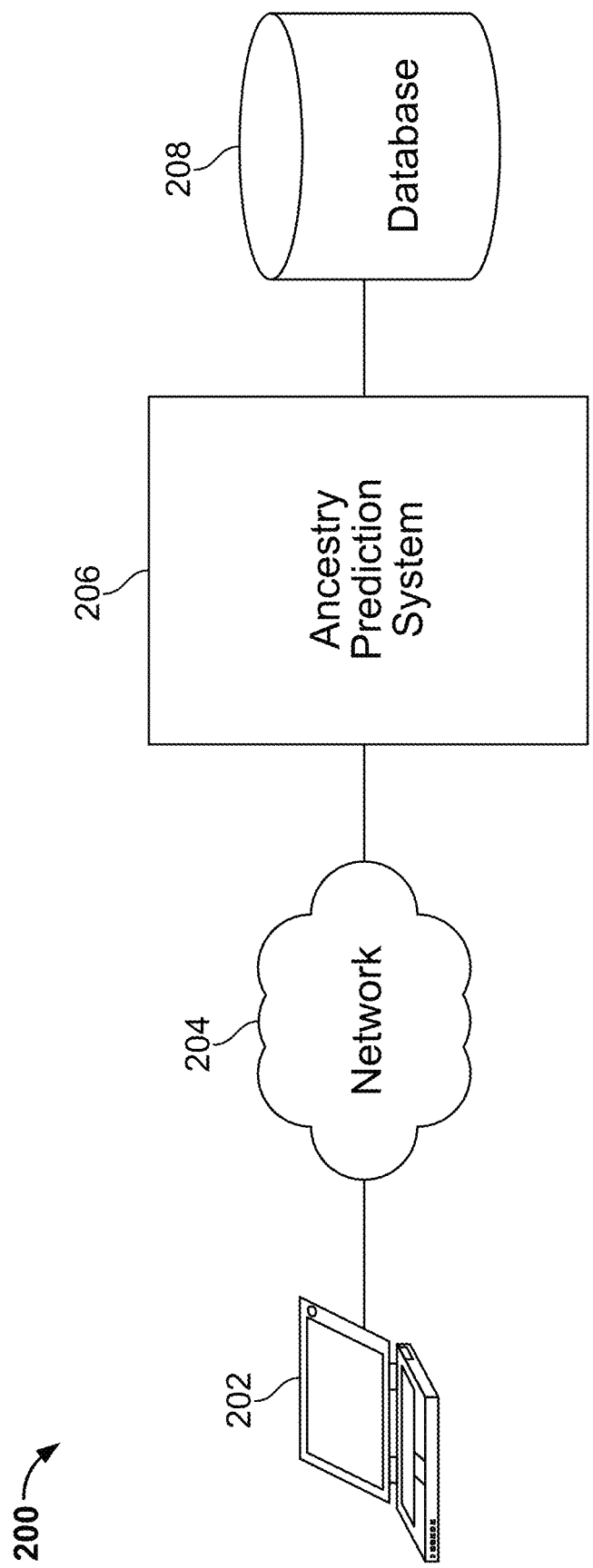
FIG. 2 is a block diagram illustrating an embodiment of an ancestry prediction platform.

FIG. 2 is a block diagram illustrating an embodiment of an ancestry prediction platform. In this example, a user uses a client device 202 to communicate with an ancestry prediction system 206 via a network 204. Examples of device 202 include a laptop computer, a desktop computer, a smart phone, a mobile device, a tablet device or any other computing device. Ancestry prediction system 206 is used to perform a pipelined process to predict ancestry based on a user's genotype information. Ancestry prediction system 206 can be implemented on a networked platform (e.g., a server or cloud-based platform, a peer-to-peer platform, etc.) that supports various applications. For example, embodiments of the platform perform ancestry prediction and provide users with access (e.g., via appropriate user interfaces) to their personal genetic information (e.g., genetic sequence information and/or genotype information obtained by assaying genetic materials such as blood or saliva samples) and predicted ancestry information. In some embodiments, the platform also allows users to connect with each other and share information. Device 100 can be used to implement 202 or 206.

In some embodiments, DNA samples (e.g., saliva, blood, etc.) are collected from genotyped individuals and analyzed using DNA microarray or other appropriate techniques. The genotype information is obtained (e.g., from genotyping chips directly or from genotyping services that provide assayed results) and stored in database 208 and is used by system 206 to make ancestry predictions. Reference data, including genotype data of unadmixed individuals (e.g., individuals whose ancestors came from the same region), simulated data (e.g., results of machine-based processes that simulate biological processes such as recombination of parents' DNA), pre-computed data (e.g., a precomputed reference haplotype graph used in out-of-sample phasing) and the like can also be stored in database 208 or any other appropriate storage unit.

Figure 3:
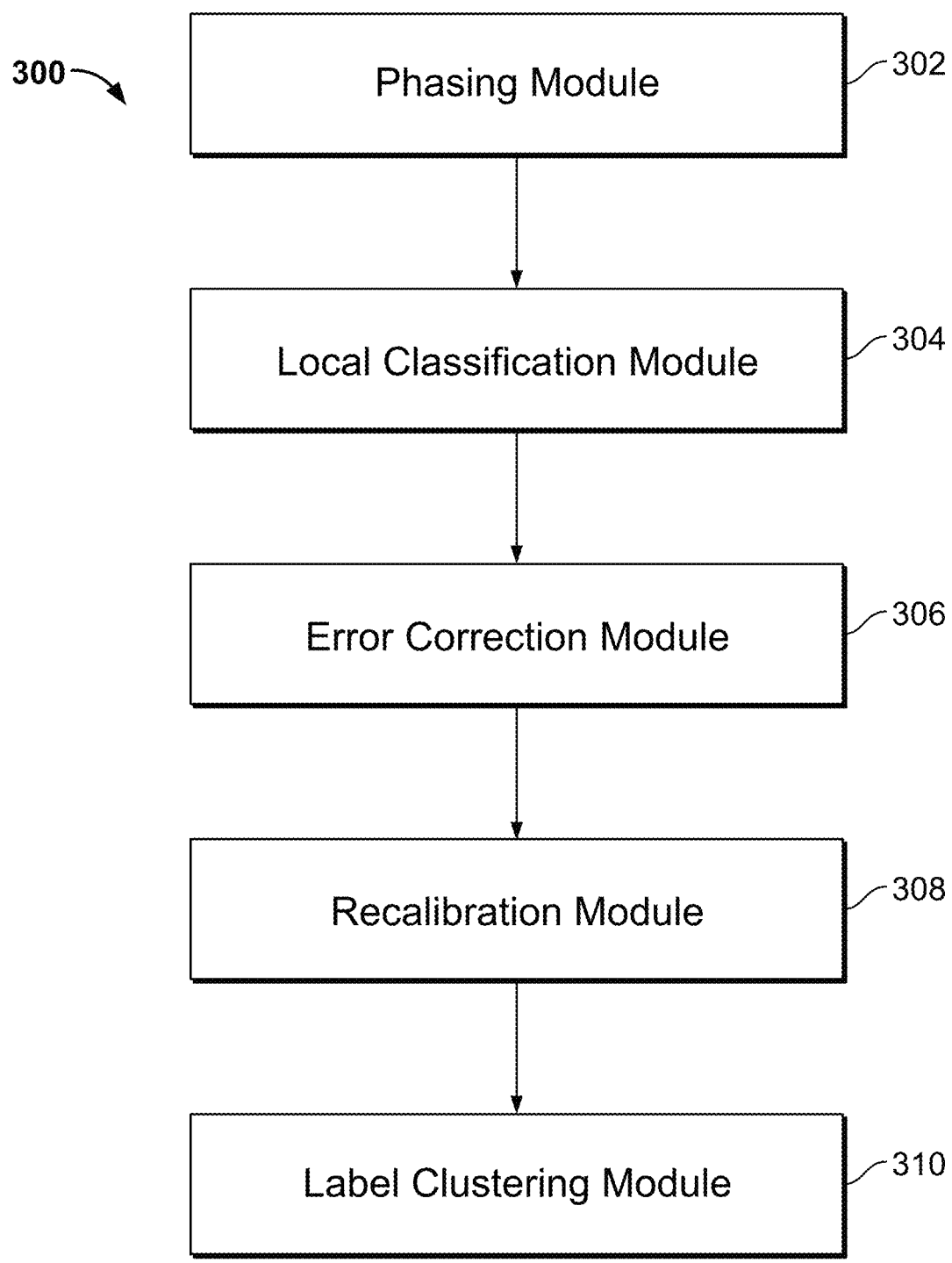
FIG. 3 is an architecture diagram illustrating an embodiment of an ancestry prediction system.

FIG. 3 is an architecture diagram illustrating an embodiment of an ancestry prediction system. System 300 can be used to implement 206 of FIG. 2, and can be implemented using system 100 of FIG. 1. The processing pipeline of system 300 includes a phasing module 302, a local classification module 304, and an error correction module 306. These modules form a predictive engine that makes predictions about the respective ancestries that correspond to the individual's chromosome portions. Optionally, a recalibration module 308 and/or a label clustering module 310 can also be included to refine the output of the predictive engine.

The input to phasing module 302 comprises unphased genotype data, and the output of the phasing module comprises phased genotype data (e.g., two sets of haplotype data). In some embodiments, phasing module 302 performs out-of-sample phasing where the unphased genotype data being phased is not included in the reference data used to perform phasing. The phased genotype data is input into local classification module 304, which outputs predicted ancestry information associated with the phased genotype data. In some embodiments, the phased genotype data is segmented, and the predicted ancestry information includes one or more ancestry predictions associated with the segments. The posterior probabilities associated with the predictions are also optionally output. The predicted ancestry information is sent to error correction module 306, which averages out noise in the predicted ancestry information and corrects for phasing errors introduced by the phasing module and/or correlated prediction errors introduced by the local classification module. The output of the error correction module can be presented to the user (e.g., via an appropriate user interface). Optionally, the error correction module sends its output (e.g., error corrected posterior probabilities) to a recalibration module 308, which recalibrates the output to establish confidence levels based on the error corrected posterior probabilities. Also optionally, the calibrated confidence levels are further sent to label clustering module 310 to identify appropriate ancestry assignments that meet a confidence level requirement.

The modules described above can be implemented as software components executing on one or more processors, as hardware such as programmable logic devices and/or Application Specific Integrated Circuits designed to perform certain functions or a combination thereof. In some embodiments, the modules can be embodied by a form of software products which can be stored in a nonvolatile storage medium (such as optical disk, flash storage device, mobile hard disk, etc.), including a number of instructions for making a computer device (such as personal computers, servers, network equipment, etc.) implement the methods described in the embodiments of the present application. The modules may be implemented on a single device or distributed across multiple devices. The functions of the modules may be merged into one another or further split into multiple sub-modules.

In addition to being a part of the pipelined ancestry prediction process, the modules and their outputs can be used in other applications. For example, the output of the phasing module can be used to identify familial relatives of individuals in the reference database.

Figure 4:
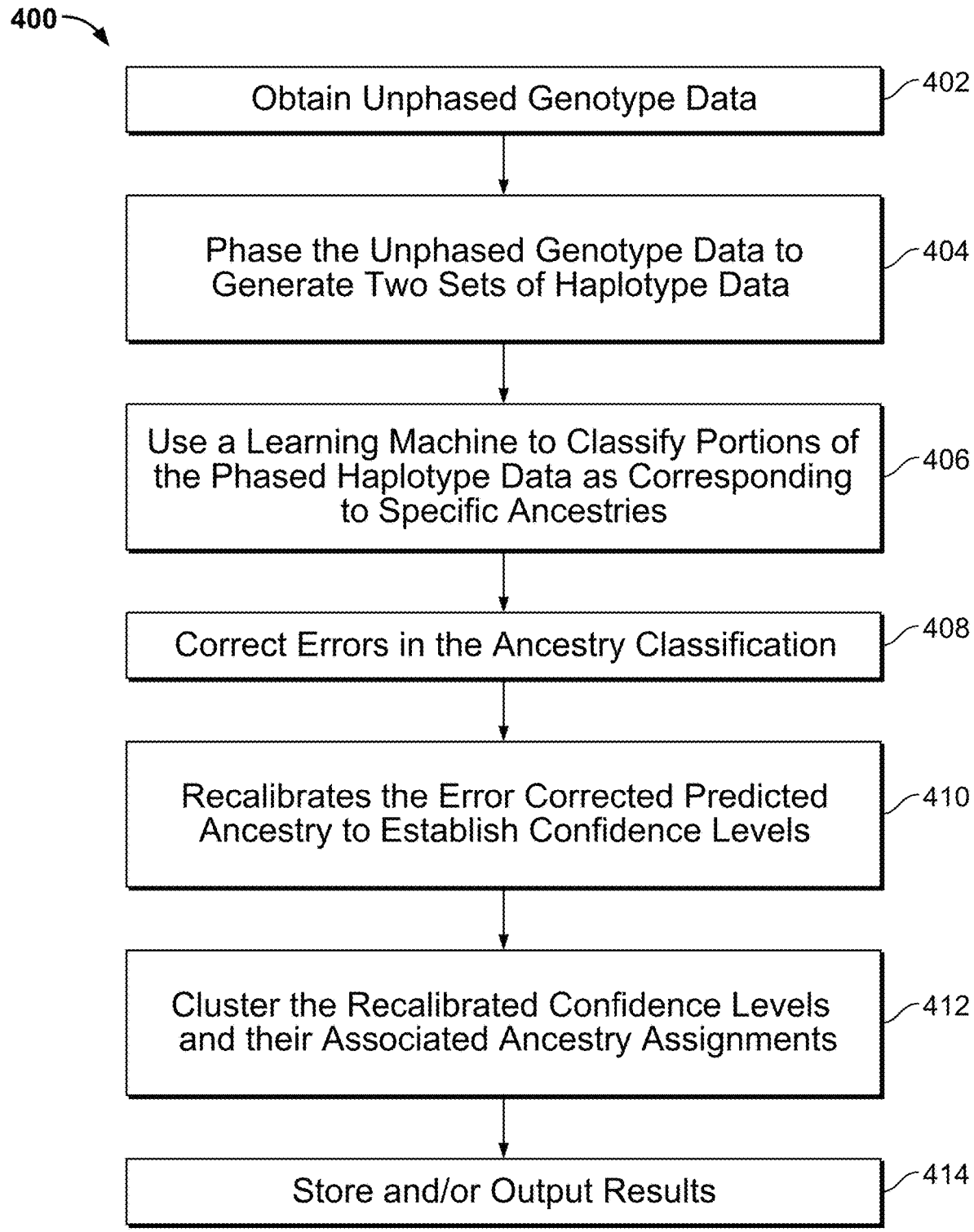
FIG. 4 is a flowchart illustrating an embodiment of a process for ancestry prediction.

FIG. 4 is a flowchart illustrating an embodiment of a process for ancestry prediction. Process 400 initiates at 402, when unphased genotype data associated with one or more chromosomes of an individual is obtained. The unphased genotype data can be received from a data source such as a database or a genotyping service, or obtained by user upload. At 404, the unphased genotype data are phased using an out-of-sample technique to generate two sets of phased haplotype data. Each set of phased haplotype data corresponds to the DNA the individual inherited from one biological parent. At 406, a learning machine (e.g., a support vector machine (SVM)) is used to classify portions of the two sets of haplotype data as being associated with specific ancestries respectively and generate ancestry classification results. At 408, errors in the results of the ancestry classification are corrected. In some embodiments, error correction removes noise, corrects phasing errors and/or corrects correlated prediction errors. In some implementations, error correction is performed using a single module (e.g., a Hidden Markov Model (HMM)) that operates on the ancestry classification results from multiple chromosomes of the individual. In other implementations, error correction is performed using separate modules for each of two or more chromosomes. In other words, a first error correction module is dedicated to a first chromosome, a second error correction module is dedicated to a second chromosome, and so on. Optionally, at 410, the error corrected predicted ancestry information is recalibrated to establish confidence levels. Optionally, at 412, the recalibrated confidence levels and their associated ancestry assignments are clustered as appropriate to identify ancestry assignments that meet a confidence level requirement. Optionally, at 414, the resulting confidence levels and their associated ancestry assignments are stored to a database and/or output to another application (e.g., an application that analyzes the results and/or displays predicted ancestry information to users).

Details of the modules and their operations are described below.

Phasing

At a given gene locus on a pair of autosomal chromosomes, a diploid organism (e.g., a human being) inherits one allele of the gene from the mother and another allele of the gene from the father. At a heterozygous gene locus, two parents contribute different alleles (e.g., one A and one C). Without additional processing, it is impossible to tell which parent contributed which allele. Such genotype data that is not attributed to a particular parent is referred to as unphased genotype data. Typically, initial genotype readings obtained from genotyping chips manufactured by companies such as Illumina® are in an unphased form.

Figures 5A, 5B:
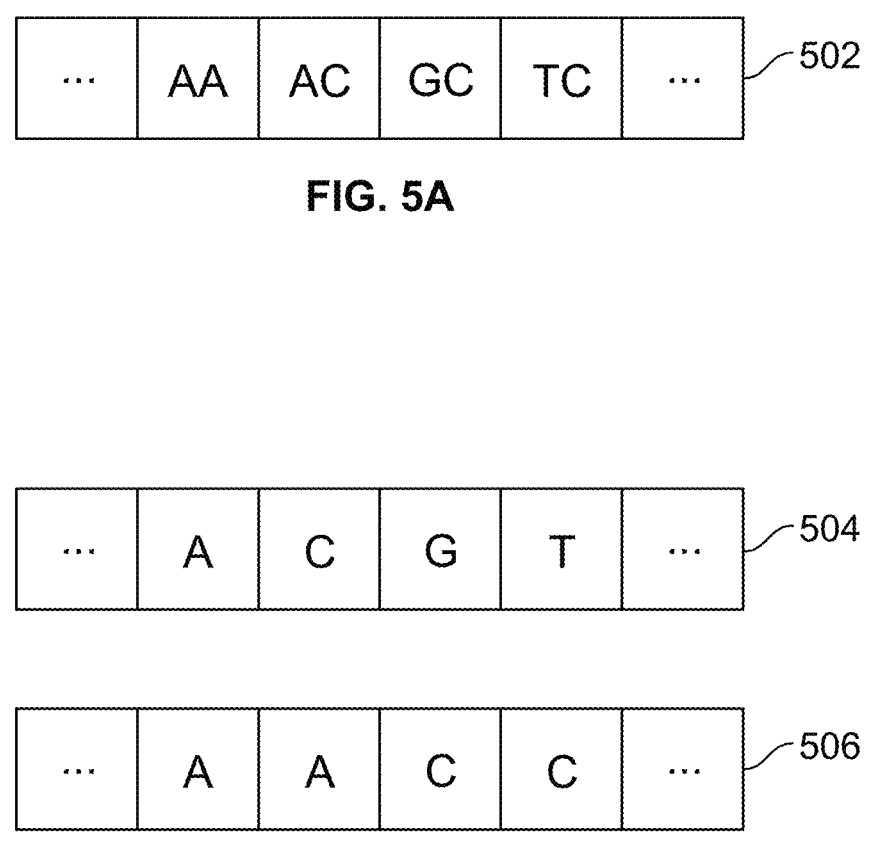

FIG. 5A illustrates an example of a section of unphased genotype data. Genotype data section 502 includes genotype calls at known SNP locations of a chromosome pair. The process of phasing is to split a stretch of unphased genotype calls such as 502 into two sets of phased genotype data (also referred to as haplotype data) attributed to a particular parent. Phasing is needed for identifying ancestry from each parent and classifying haplotypes from different ancestral origins. Further, a specific marker alone tends not to offer good ancestral (e.g., geographical or ethic) specificity, but a run of multiple markers can offer better specificity. For example, a particular SNP of "A" is not very informative with respect to the ancestry origin of the section of DNA, but a haplotype of a longer stretch (e.g., "ACGA") starting at a specific location can be highly correlated with Northern European ancestry.

FIG. 5B illustrates an example of two sets of phased genotype data. In this example, phased genotype data (i.e., haplotype data) 504 and 506 is obtained from unphased genotype data 502 based on statistical techniques. Haplotype block 504 ("ACGT") is determined to be attributed to (i.e., inherited from) one parent, and haplotype block 506 ("AACC") is determined to be attributed to another parent.

Population-Based Phasing

Phasing is often done using statistical techniques. Such techniques are also referred to as population-based phasing because genotype data from a reference collection of a population of individuals (e.g., a few hundred to a thousand) is analyzed. BEAGLE is a commonly used population-based phasing technique. It makes statistical determinations based on the assumption that certain blocks of haplotypes are inherited in blocks and therefore shared amongst individuals. For example, if the genotype data of a sample population comprising many individuals shows a common pattern of "?A ?C ?G ?T" (where "?" can be any other allele), then the block "ACGT" is likely to be a common block of haplotypes that is present in these individuals. The population-based phasing technique would therefore identify the block "ACGT" as coming from one parent whenever "?A ?C ?G ?T" is present in the genotype data. Because BEAGLE requires that the genotype data being analyzed be included in the reference collection, the technique is referred to as in-sample phasing.

In-sample phasing is often computationally inefficient. Phasing of a large database of a user's genome (e.g., 100,000 or more) can take many days, and it can take just as long whenever a new user has to be added to the database since the technique would recompute the full set of data (including the new user's data). There can also be mistakes during in-sample phasing. One type of mistake, referred to as phasing errors or switch errors, occurs where a section of the chromosome is in fact attributed to one parent but is mis-identified as attributed to another parent. Switch errors can occur when a stretch of genotype data is not common in the reference population. For example, suppose that a parent actually contributed the haplotype of "ACCC" and another parent actually contributed the haplotype of "AAGT" to genotype 502. Because the block "ACGT" is common in the reference collection and "ACCC" has never appeared in the reference collection, the technique attributes "ACGT" and "AACC" to two parents respectively, resulting in a switch error.

Embodiments of the phasing technique described below permit out-of-sample population-based phasing. In out-of-sample phasing, when genotype data of a new individual needs to be phased, the genotype data is not necessarily immediately combined with the reference collection to obtain phasing for this individual. Instead, a precomputed data structure such as a predetermined reference haplotype graph is used to facilitate a dynamic programming based process that quickly phases the genotype data. For example, given the haplotype graph and unphased data, the likely sequence of genotype data can be solved using the Viterbi algorithm. This way, on a platform with a large number of users forming a large reference collection (e.g., at least 100,000 individuals), when a new individual signs up with the service and provides his/her genotype data, the platform is able to quickly phase the genotype data without having to recompute the common haplotypes of the existing users plus the new individual.

Figure 6:
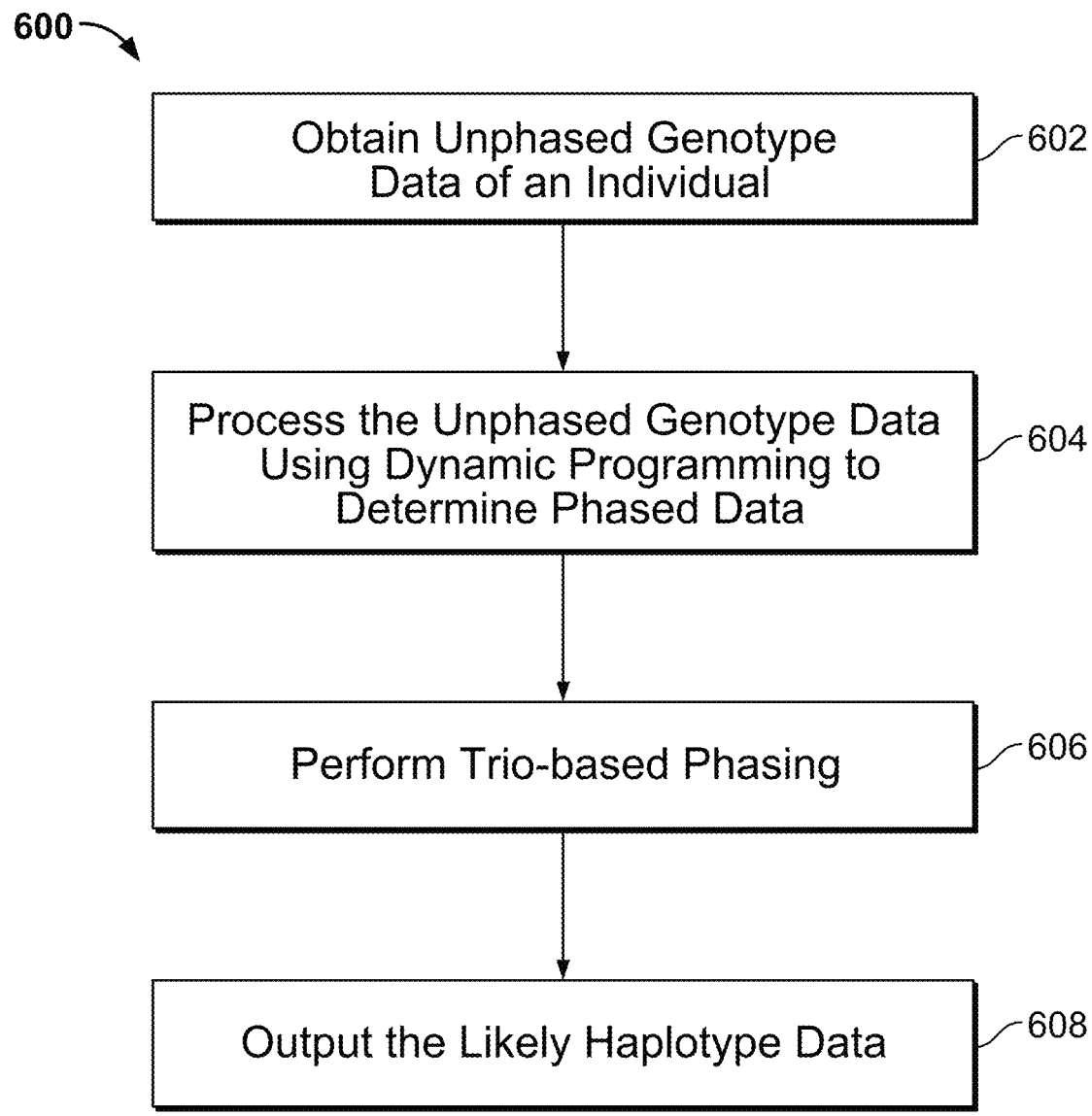
FIG. 6 is a flowchart illustrating an embodiment of a process for performing out-of-sample phasing.

FIG. 6 is a flowchart illustrating an embodiment of a process for performing out-of-sample phasing. Process 600 can be performed on a system such as 100 or 206, and can be used to implement phasing module 302.

At 602, unphased genotype data of the individual is obtained. In some embodiments, the unphased genotype data such as sequence data 502 is received from a database, a genotyping service, or as an upload by a user of a platform such as 100.

At 604, the unphased genotype data is processed using dynamic programming to determine phased data, i.e., sets of likely haplotypes. The processing requires a reference population and is therefore referred to as population-based phasing. In some embodiments, the dynamic programming relies on a predetermined reference haplotype graph. The predetermined haplotype graph is precomputed without referencing the unphased genotype data of the individual. Thus, the unphased genotype data is said to be out-of-sample with respect to a collection of reference genotype data used to compute the predetermined reference haplotype graph. In other words, if the unphased genotype data is from a new user whose genotype data is not already included in the reference genotype data and therefore is not incorporated into the predetermined reference haplotype graph, it is not necessary to include the unphased genotype data from the new user in the reference genotype data and recompute the reference haplotype graph. Details of dynamic programming and the predetermined reference haplotype graph are described below.

At 606, trio-based phasing is optionally performed to improve upon the results from population-based phasing. As used herein, trio-based phasing refers to phasing by accounting for the genotyping data of one or more biological parents of the individual.

At 608, the likely haplotype data is output to be stored to a database and/or processed further. In some embodiments, the likely haplotype data is further processed by a local classifier as shown in FIG. 3 for ancestry prediction purposes.

The likely haplotype data can also be used in other applications, such as being compared with haplotype data of other individuals in a database to identify the amount of DNA shared among individuals, thereby determining people who are related to each other and/or people belonging to the same population groups.

In some embodiments, the dynamic programming process performed in step 604 uses a predetermined reference haplotype graph to examine possible sequences of haplotypes that could be combined to generate the unphased genotype data, and determine the most likely sequences of haplotypes. Given a collection of binary strings of length L, a haplotype graph is a probabilistic deterministic finite automaton (DFA) defined over a directed acyclic graph. The nodes of the multigraph are organized into L+1 levels (numbered from 0 to L), such that level 0 has a single node representing the source (i.e., initial state) of the DFA and level L has a single node representing the sink (i.e., accepting state) of the DFA. Every directed edge in the multigraph connects a node from some level i to a node in level (i+1) and is labeled with either 0 or 1. Every node is reachable from the source and has a directed path to the sink. For each path through the haplotype graph from the source to the sink, the concatenation of the labels on the edges traversed by the path is a binary string of length L. Semantically, paths through the graph represent haplotypes over a genomic region comprising L biallelic markers (assuming an arbitrary binary encoding of the alleles at each site). A probability distribution over the set of haplotypes included in a haplotype graph can be defined by associating a conditional probability with each edge (such that the sum of the probabilities of the outgoing edges for each node is equal to 1), and generated by starting from the initial state at level 0, and choosing successor states by following random outgoing edges according to their assigned conditional probabilities.

Figure 7:
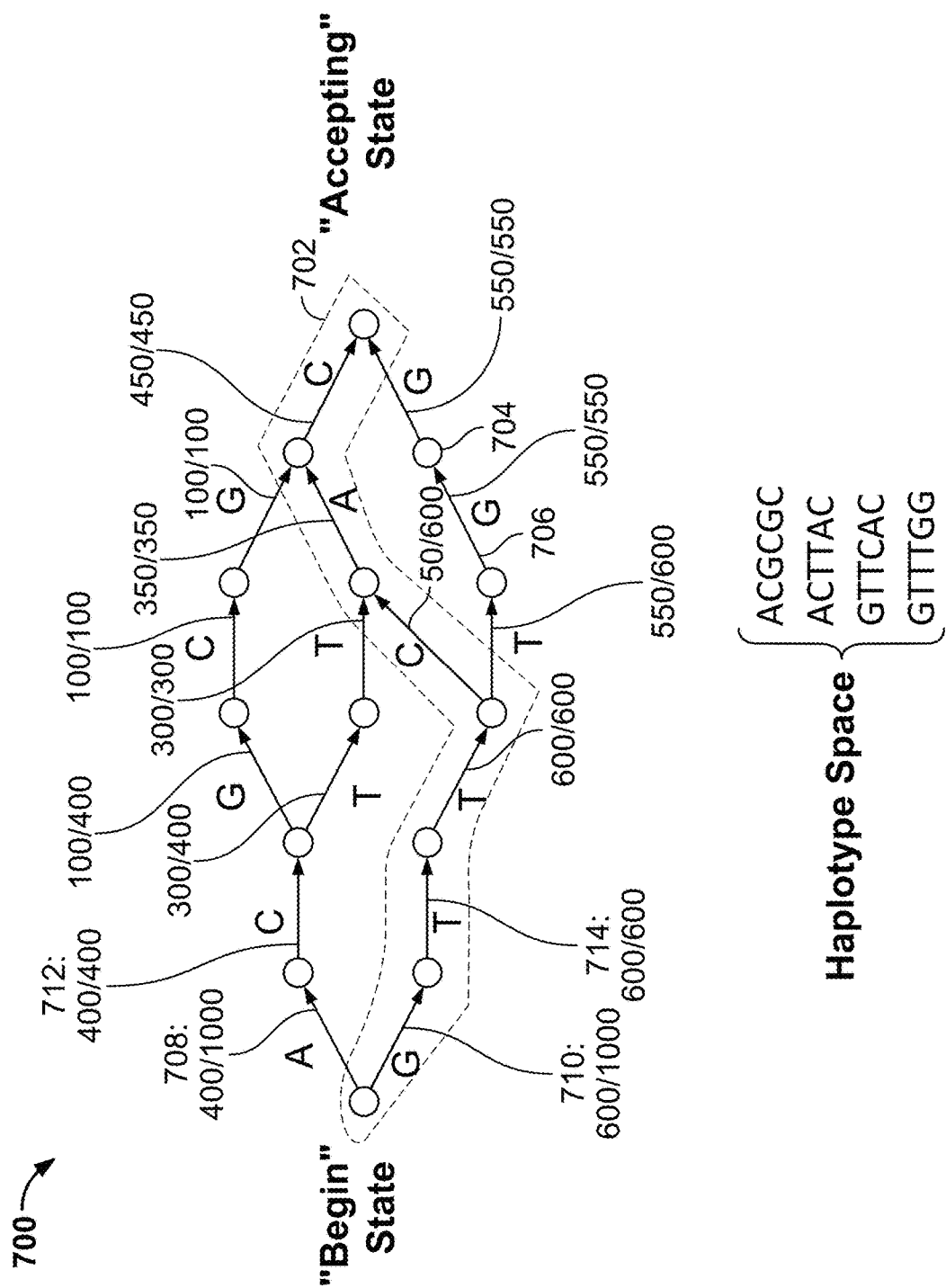
FIG. 7 is a diagram illustrating an example of a predetermined reference haplotype graph that is built based on a reference collection of genotype data.

FIG. 7 is a diagram illustrating an example of a predetermined reference haplotype graph that is built based on a reference collection of genotype data (e.g., population-based data). In this example, the reference collection of genotype data includes a set of L genetic markers (e.g., SNPs). Haplotype graph 700 is a Directed Acyclic Graph (DAG) having nodes (e.g., 704) and edges (e.g., 706). The haplotype graph starts with a single node (the "begin state") and ends on a single node (the "accepting state"), and the intermediate nodes correspond to the states of the markers at respective gene loci. There is a total of L+1 levels of nodes from left to right. An edge, e, represents the set of haplotypes whose path from the initial node to the terminating node of the graph traverses e. The possible paths define the haplotype space of possible genotype sequences. For example, in haplotype graph 700, a possible path 702 corresponds to the genotype sequence "GTTCAC". There are four possible paths/genotype sequences in the haplotype space shown in this diagram ("ACGCGC," "ACTTAC," "GTTCAC," and "GTTTGG").

Each edge is associated with a probability computed based on the reference collection of genotype data. In this example, a collection of genotype data is comprised of genotype data from 1000 individuals, of which 400 have the "A" allele at the first locus, and 600 have the "G" allele at the first locus. Accordingly, the probability associated with edge 708 is 400/1000 and the probability associated with edge 710 is 600/1000. All of the first 400 individuals have the "C" allele at the second locus, giving edge 712 a probability of 400/400. All of the next 600 individuals who had the "G" allele at the first locus have the "T" allele at the second locus, giving edge 714 a probability of 600/600, and so on. The probabilities associated with the respective edges are labeled in the diagram. The probability associated with a specific path is expressed as the product of the probabilities associated with the edges included in the path. For example, the probability associated with path 702 is computed as:

$$P(h) = \left(\frac{600}{1000}\right)\left(\frac{600}{600}\right)\left(\frac{600}{600}\right)\left(\frac{50}{600}\right)\left(\frac{350}{350}\right)\left(\frac{450}{450}\right) = 0.05$$

The dynamic programming process searches the haplotype graph for possible paths, selecting two paths $h_1$ and $h_2$ for which the product of their associated probabilities is maximized, subject to the constraint that when the two paths are combined, the alleles at each locus must match the corresponding alleles in the unphased genotype data (g). The following expression is used in some cases to characterize the process:

maximize $P(h_1)P(h_2)$, subject to $h_1+h_2=g$

For out-of-sample phasing, the reference haplotype graph is built once and reused to identify possible haplotype paths that correspond to the unphased genotype data of a new individual (a process also referred to as "threading" the new individual's haplotype along the graph). The individual's genotype data sometimes does not correspond to any existing path in the graph (e.g., the individual has genotype sequences that are unique and not included in the reference population), and therefore cannot be successfully threaded based on existing paths of the reference haplotype graph. To cope with the possibility of a non-existent path, several modifications are made to the reference haplotype graph to facilitate the out-of-sample phasing process.

Figure 8A:
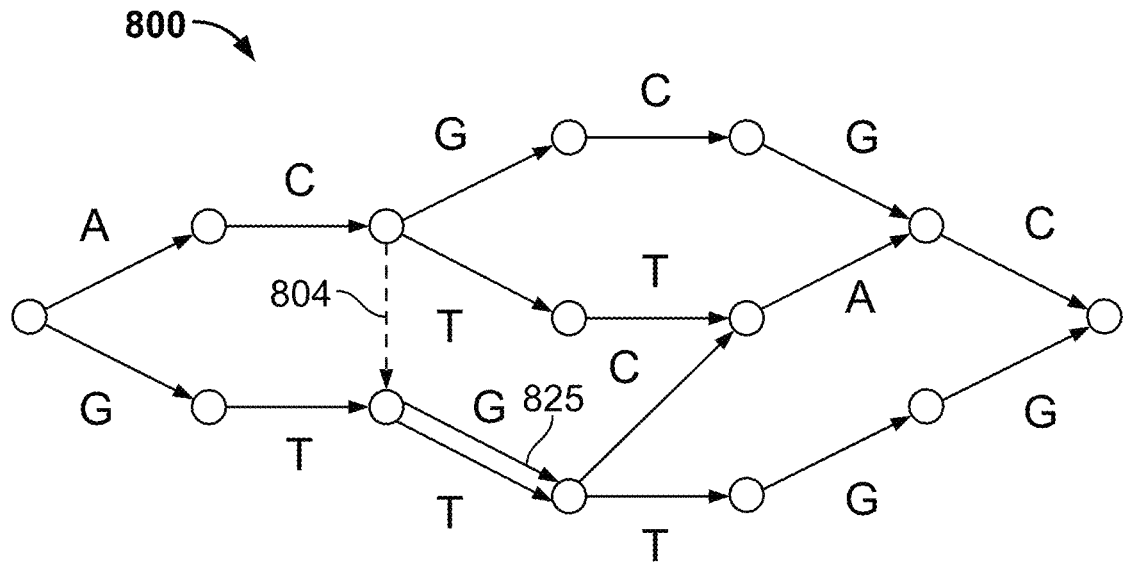
FIGS. 8A and 8B are diagrams illustrating embodiments of modified haplotype graphs.
Figure 8B:
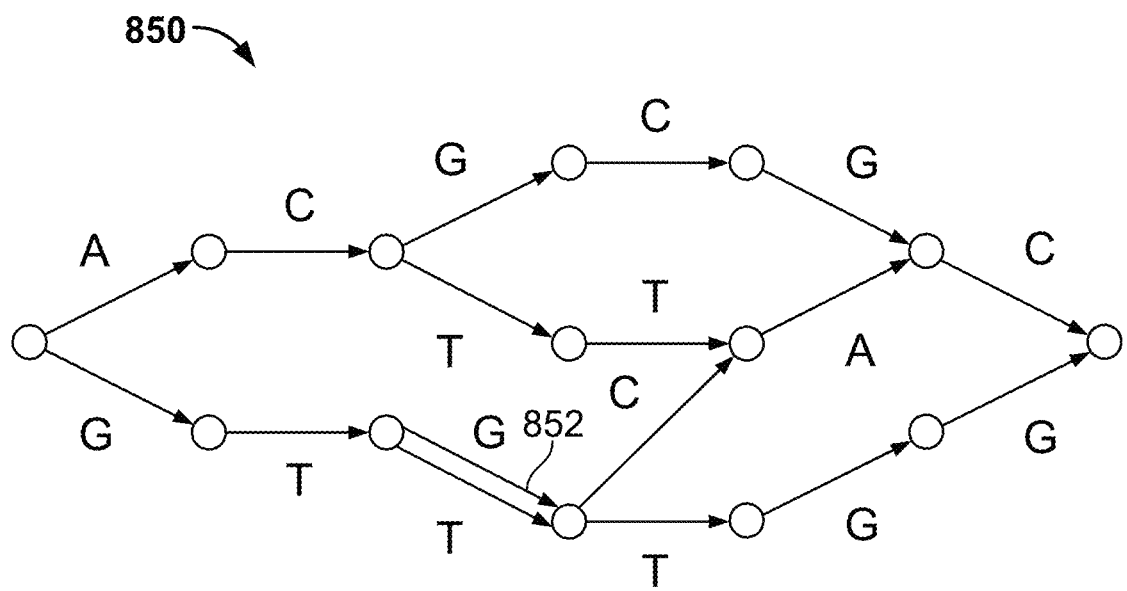

FIGS. 8A-8B are diagrams illustrating embodiments of modified haplotype graph used for out-of-sample, population-based phasing. In these examples, modified reference haplotype graphs 800 and 850 are based on graph 700. Unlike graph 700, which is based on exact readings of genotype sequences of the reference individuals, the modified graphs permit recombination and genotyping errors and include modifications (e.g., extra edges) that account for recombination and genotyping errors.

Recombination is one reason to extend graph 700 for out-of-sample phasing. As used herein, recombination refers to the switching of a haplotype along one path to a different path. Recombination can happen when segments of parental chromosomes cross over during meiosis. In some embodiments, reference haplotype graph 700 is extended to account for the possibility of recombination/path switching. Recombination events are modeled by allowing a new haplotype state to be selected (independent of the previous haplotype state) with probability $\tau$ at each level of the haplotype graph. By default, $\tau \approx 0.00448$, which is an estimate of the probability of recombination between adjacent sites, assuming 500,000 uniformly spaced markers, a genome length of 37.5 Morgans, and 30 generations since admixture. Referring to the example of FIG. 8A, suppose the new individual's unphased genotype data is "AG, CT, TT, TT, GG, GG," (SEQ ID NO: 1) which cannot be split into two haplotypes by threading along existing paths in graph 700. The modified reference haplotype graph 800 permits recombination by including additional edges representing recombination (e.g., edge 804) so that new paths can be formed along these edges. In this example, the unphased genotype data can map onto two paths corresponding to haplotypes "ACTTGG" and "GTTTGG", the former being a new path due to recombination with a recombination occurring between "C" and "T" along edge 804. $\tau$ is associated with edge 804 and used to compute the probability of the path through 804.

Genotyping error is another reason to extend graph 700 for out-of-sample phasing. Genotyping errors can occur because the genotyping technology is imperfect and can make false readings. The rate of genotyping error for a given technology (e.g., a particular genotyping chip) can be obtained from the manufacturer. In some embodiments, when the search for possible paths for a new individual cannot be done according to the existing reference graph, the existing reference haplotype graph is extended to account for the possibility of genotyping errors. For example, suppose the new individual's unphased genotype data is "AG, CT, GG, CT, GG, CG," (SEQ ID NO: 2) which cannot be split into two haplotypes by threading along existing paths in graph 700. Referring to FIG. 8B, the reference haplotype graph is extended to permit genotyping errors and a new edge 852 is added to the graph, permitting a reading of "G" instead of "T" at this locus. The probability associated with this edge is determined based on the rate of genotyping error for the genotyping technology used. The unphased genotype data can therefore be split into haplotypes "ACGCGC" and "GTGTGG", the latter being a new path based on the extended reference haplotype graph. In some embodiments, to account for genotyping error, the out-of-sample phaser explicitly allows genotyping error with a constant probability of y (which depends on the error rate of the given technology, and is set to 0.01 in some cases) for each emitted edge label.

The example graphs shown include a small number of nodes and edges, and thus represent short sequences of genotype data. In practice, the begin state node corresponds to the first locus on the chromosome and the accepting state node the last locus on the chromosome, and the number of edges in a path corresponds to the number of SNPs in a chromosome (L), which can be on the order of 50,000 in some embodiments. The thickest portion of the graph (i.e., a locus with the greatest number of possible paths), which depends at least in part on the DNA sequences of individuals used to construct the graph (K), can be on the order of 5,000 in some embodiments. A large number of computations would be needed ($O(L1(4)$ in the worst case) for a naïve implementation of a dynamic programming solution based on the Viterbi algorithm.

In some embodiments, the paths are pruned at each state of the graph to further improve performance. In other words, only likely paths are kept in the modified graph and unlikely paths are discarded. In some embodiments, after i markers (e.g., 3 markers), paths with probabilities below a certain threshold E (e.g., less than 0.0001%) are discarded. For example, a haplotype along a new path that accounts for both recombination and switching error would have very low probability of being formed, and thus can be discarded. As another example, in the case of unphased genotype data of "AG, CT, GG, CT, GG, CG," (SEQ ID NO: 2) a new haplotype accounting for recombination can be forged by switching paths several times along the graph (additional edges would need to be added but are not shown in the diagram). Given the low probability associated with each switch, however, the formation of such a haplotype is very unlikely and would be pruned from the resulting graph, while the path that includes the genotyping error 825 has sufficiently high probability, and is kept in the graph and used to thread the unphased genotype data into phased genotype data. By pruning unlikely paths from the modified graph, the dynamic programming-based phasing process is prevented from exploring very unlikely paths in the graph when threading a new haplotype along it. The choice of E determines the trade-off between the efficiency of the algorithm (in both time and space) and the risk of prematurely excluding the best Viterbi path. Computation savings provided by pruning can be significant. In some cases, phasing using a naïve implementation can require 15 days per person while phasing with pruning only requires several minutes per person.

In some embodiments, the nodes and edges of the haplography can be represented as follows:

```
struct Node {
    int32 tid;
    int32 t level;
    Edge *outgoing[2];
};
struct Edge {
    int16 tid;
    int8 t allele;
```

```
    float weight;
    Node *to;
}
```

Even with a pruned haplotype graph, the number of nodes and edges can be large and using the above data structures to represent the graph would require a vast amount of memory (on the order of several gigabytes in some cases). In some embodiments, the graph is represented in a compressed form, using segments. The term "segment" used herein refers to the data structure used to represent the graph in a compressed form and is different from the DNA segments used elsewhere in the specification. Each segment corresponds to a contiguous set of edges in the graph, with the following constraints: the end of the segment has up to 1 branch (0 branches are permitted), and no segment points to the middle of another segment. In some embodiments, the data structure of a segment is represented as follows:

```
struct Segment {
    int32_t timestamp;
    int32_t index;
    int32_t begin;
    int32_t end;
    int32_t count[2];
    Segment *edges[2];
}
```

Figure 9:
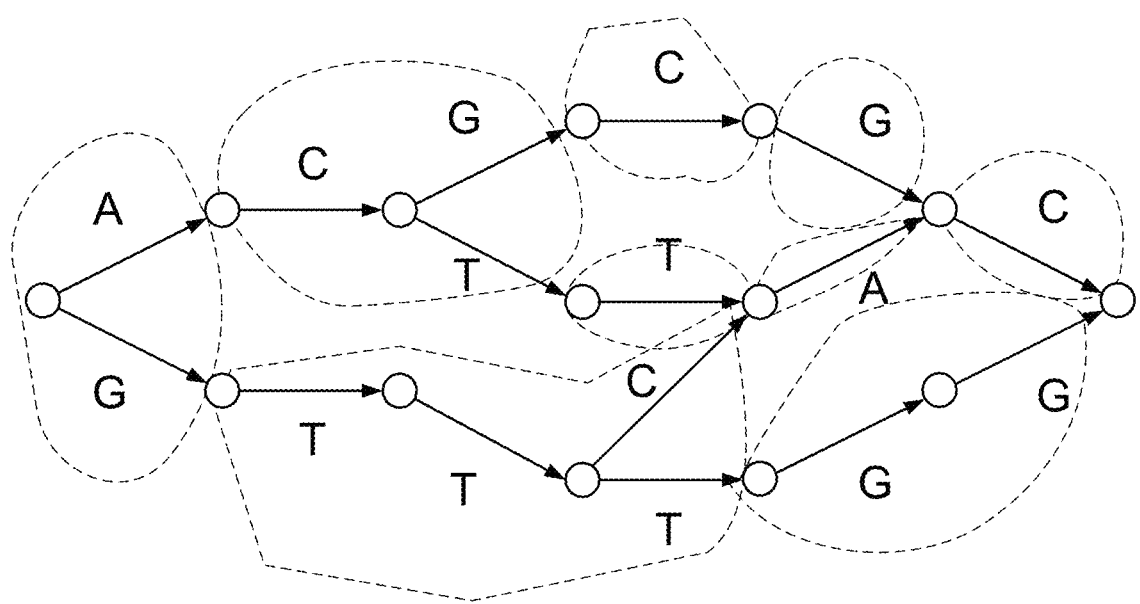
FIG. 9 is a diagram illustrating an embodiment of a compressed haplotype graph with segments.

FIG. 9 is a diagram illustrating an embodiment of a compressed haplotype graph with segments. In this example, dashed shapes are used to illustrate the individual segments enclosed within. In some cases, a compressed graph associated with a chromosome can be represented using several megabytes of memory, achieving memory reduction by a factor of 1000 compared to the naïve implementation of nodes and edges.

Trio-Based Phasing

On a system such as the personal genomics services platform provided by 23andMe®, DNA sequence information of one or both parents of the individual is sometimes available and can be used to further refine phasing. With the exception of sites where all three individuals are heterozygous, the parental origin of each allele can be determined unambiguously. For ambiguous sites, knowledge of patterns of local linkage disequilibrium can be used to statistically estimate the most likely phase. In some embodiments, a refinement process that accounts for parental DNA sequence information, referred to as trio-based phasing, is optionally performed following the population-based phasing process to correct any errors in the output of the population-based phasing process and improve phasing accuracy. In some embodiments, the trio-based phasing technique is a post-processing step to be applied to sequences for which a previous population-based linkage-disequilibrium phasing approach has already been applied. The trio-based phasing technique can be used in combination with any existing phasing process to improve phasing quality, provided that an estimate of the switch error rate (also referred to as the phasing error rate) is available.

In some embodiments, trio-based phasing receives as inputs a set of preliminary phased haplotype data (e.g., output of an out-of-sample population-based phasing technique described above), and employs a probabilistic graphic model (also referred to as a dynamic Bayesian network) that models the observed alleles, hidden states, and relationships of the parental and child haplotypes. The input includes the set of preliminary phased haplotype data as well as the phased haplotype data of at least one parent. The genotype data at a particular site (e.g., the i-th SNP on a chromosome) for each individual in the trio (i.e., mom, dad, or child (i.e. the individual whose genetic data is being phased)) are represented by the following variables:

$G_0^{*,i}, G_1^{*,i} \in \{0,1\}$: the observed alleles for haplotypes 0 and 1, provided as input data. For the child, the input data can be obtained from the output of the population-based phasing process (e.g., the preliminary haplotype data). For the parent, the input data can be the output of the population-based phasing process or the final output of a refined process.

$H_m^{*,i}, H_p^{*,i} \in \{0,1\}$: the hidden true alleles of the individual's maternal (m) and paternal (p) haplotypes.

$p^{*,i} \in E \{m, d\}$: a hidden binary phase indicator variable that is set to m whenever $G_0^{*,i}$ corresponds to $H_m^{*,i}$ and set to p whenever $G_0^{*,i}$ corresponds to $H_p^{*,i}$.

The relationship between parental and child haplotypes are encoded by two additional variables, $T^{mom,i}, T^{dad,i} \in \{a, b\}$, where a indicates transmission of the parent's maternal haplotype to the child and b indicates transmission of the parent's paternal haplotype to the child. In some embodiments, a=0 and b=1.

The following assumptions are made about the model:

1. The hidden true alleles for each parent at each position (i.e., $H_*^{(mom,dad),i}$), the initial phase for each individual (i.e., $p^{*,1}$), and the initial transmission for each parent (i.e., $T^{*,1}$) are independently drawn from uniform Bernoulli priors.

2. The phase indicator variables for each individual and the transmission indicator variables for each parent are each sampled according to independent first order Markov processes. Specifically, $$P(P^{*,i} \mid P^{*,i-1}) = \begin{cases} 1-s & \text{if } P^{*,i} = P^{*,i-1} \\ s & \text{otherwise} \end{cases}$$

$$P(T^{*,i} \mid T^{*,i-1}) = \begin{cases} 1-r & \text{if } T^{*,i} = T^{*,i-1} \\ r & \text{otherwise} \end{cases}$$

where s is the estimated switch error probability between consecutive sites in the input haplotypes and r is the estimated recombination probability between sites in a single meiosis. In some embodiments, s is set to a default value of 0.02 and r is set to a default value of $$\frac{1}{2}\left(1 - e^{-2\left(\frac{37.5}{500000}\right)}\right) \approx 0.000075.$$

3. The hidden true alleles for the child at each position (i.e., $H_*^{kid,i}$) are deterministically set on the parents' true hidden haplotypes (i.e., neglecting the possibility of private mutations) and their respective transmission variables.

4. The observed alleles are sampled conditionally on the true alleles and the phase variables with genotyping error, according to the following model:

$$P(G_0^{*,i} \mid H_m^{*,i}, H_p^{*,i}, P^{*,i}) = \begin{cases} 1-g & \text{if } G_0^{*,i} = H_{p^*,t}^{*,i} \\ g & \text{otherwise} \end{cases}$$

according to the estimated genotyping error rate.

Figure 10:
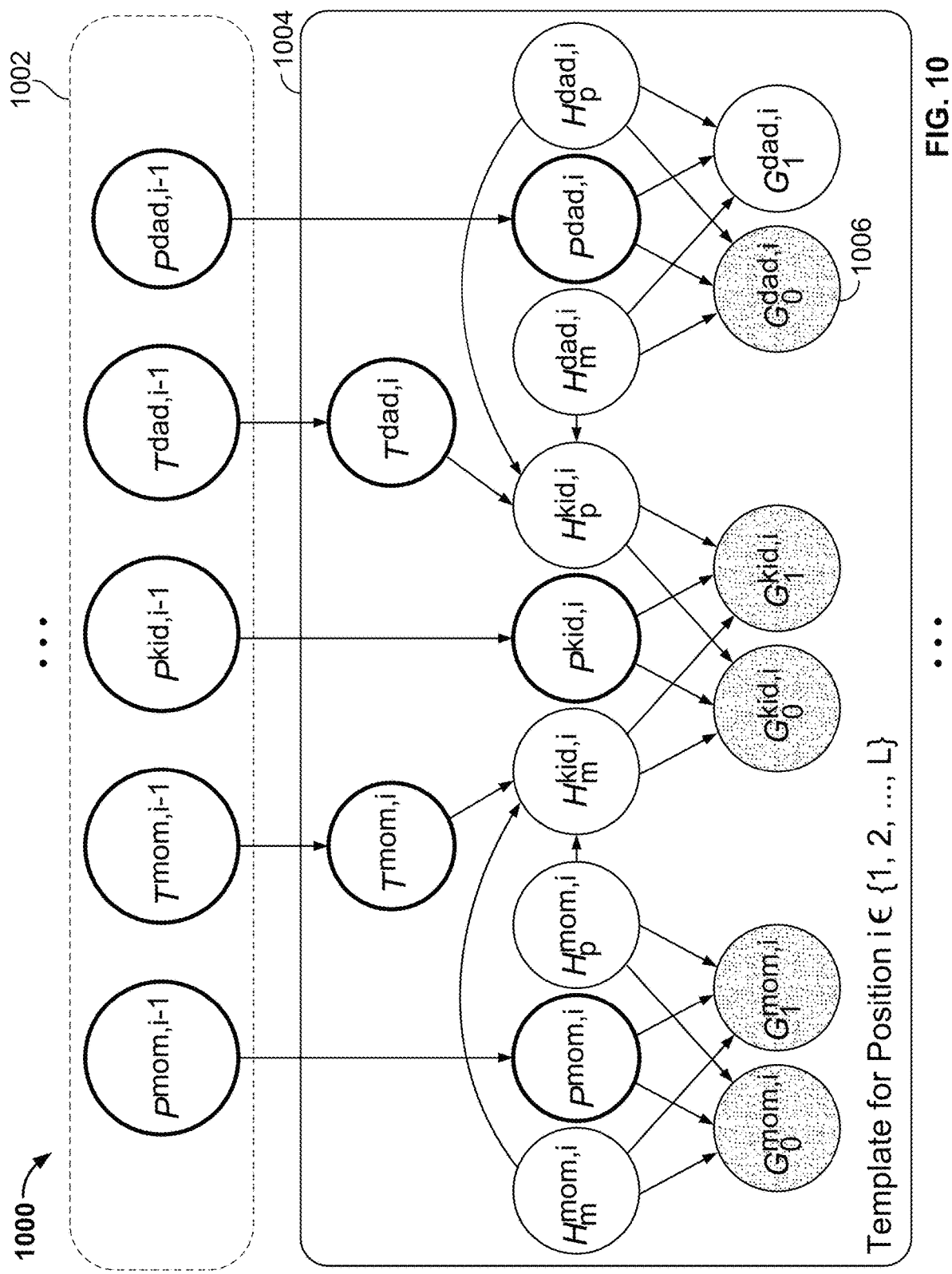
FIG. 10 is a diagram illustrating an embodiment of a dynamic Bayesian network used to implement trio-based phasing.

The following expression is used to characterize the trio-based phasing process:

maximize $Pr(H_m^{kid}, H_p^{kid}, H_m^{mom}, H_p^{mom}, H_m^{dad}, H_p^{dad})$ given $H_m^i + H_p^i = G_0^i + G_1^i \forall i \in \{kid, mom, dad\}$ FIG. 10 is a diagram illustrating an embodiment of a dynamic Bayesian network used to implement trio-based phasing. The diagram depicts the structure of the dynamic Bayesian network using plate notation. Rounded rectangles (also referred to as plates) such as 1002 and 1004 are used to denote repeated structures in the graph model. Each plate corresponds to a position (e.g., the i-th marker) on the individual's chromosome. In plate 1002 which corresponds to position i−1, variables which are not connected to any variables from other plates (e.g., $H_m^{kid,i-1}$) are omitted from the diagram. Plate 1004 shows a detailed template for position i E {1, 2, . . . , L}. As shown, nodes represent random variables in the model, and edges represent conditional dependencies. Shaded nodes (e.g., node 1006) represent random variables which are observed at testing time, and nodes with thickened edges (e.g., node 1008) represent variables which have dependencies across plates.

Trio-based phasing includes using the probabilistic model to estimate the most probable setting of all unobserved variables, conditioned on the observed alleles. In some embodiments, the most probable H variables are determined using a standard dynamic programming-based technique (e.g., Viterbi). One can visualize the model as plates corresponding to i∈{1, 2, . . . , L} being stacked in sequential order, and the paths are formed by the interconnections of nodes on the same plate, as well as nodes across plates.

Figure 11:
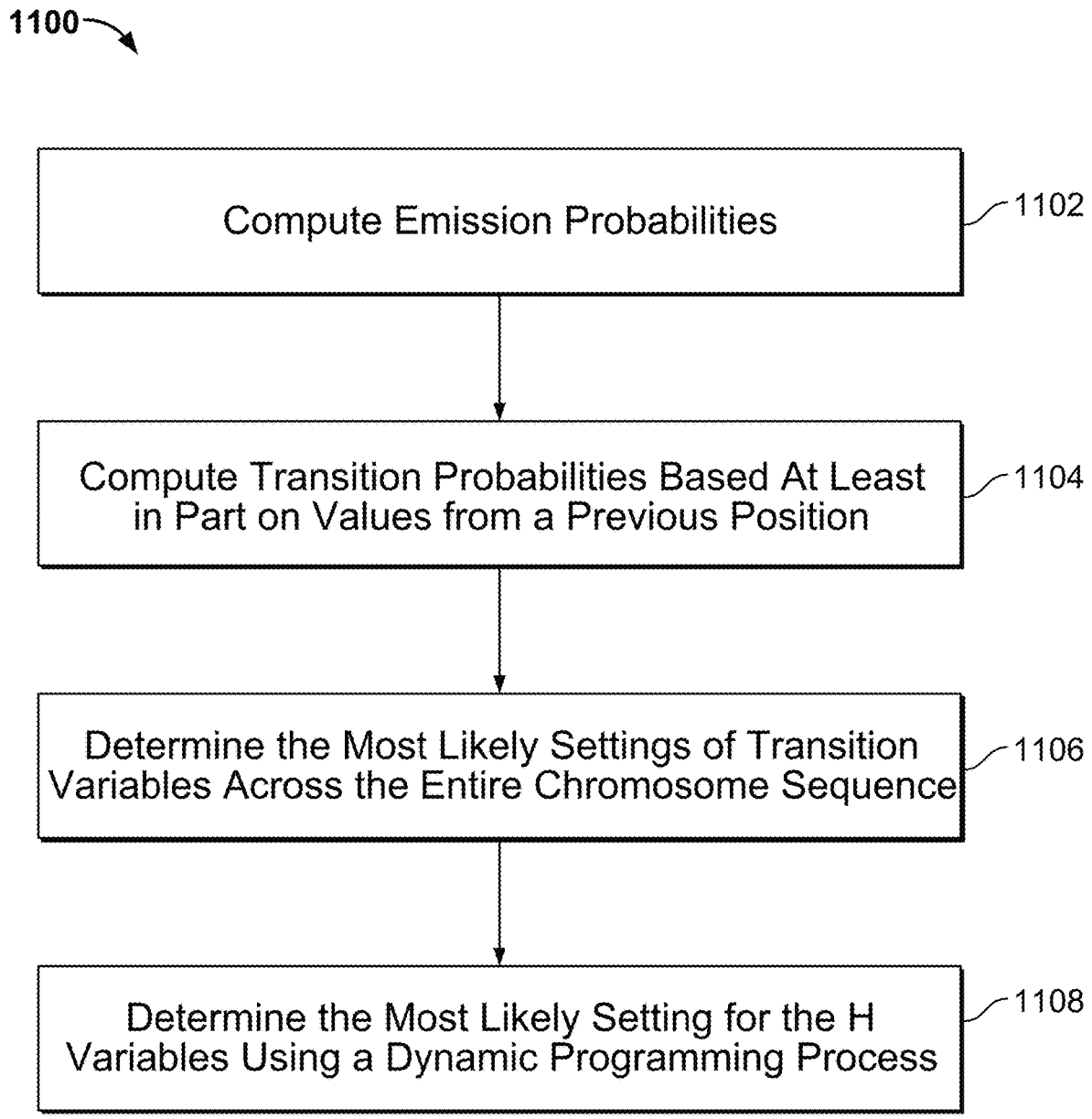
FIG. 11 is a flowchart illustrating an embodiment of a process to perform trio-based phasing.

FIG. 11 is a flowchart illustrating an embodiment of a process to perform trio-based phasing based on the model of FIG. 10. Process 1100 can be performed on a system such as 100 or 206, and can be used to implement phasing module 302 to perform post-processing of population-based phasing. It is assumed that a model such as 1000 is already established.

At 1102, emission probabilities are precomputed for each plate of model 1000. In some embodiments, the emission probabilities, which correspond to the most likely setting for the H variables given the G, P, and T variables, are found using a dynamic programming (e.g., Viterbi) based process. Referring to FIG. 10, for a given position i, there are 2 possible settings (0 or 1) for each for the variables $P^{mom}$, $P^{kid}$, $P^{dad}$, $T^{mom}$, $T^{dad}$; there are two possible settings (0 or 1) for each of the six H variables; and there are 3 possible settings (0, 1 or missing) or each of the six G variables, $2^5 * 2^6 * 3^6 = 1.5$ million possible combinations. In subsequent steps, a dynamic programming process will search these combinations to identify the most likely setting for the H variables.

At 1104, transition probabilities are computed based at least in part on the values of transition probabilities from the previous position. Referring to FIG. 10, at a given position i, the values of transition variables T and P are dependent on the values of the T and P variables from the previous position. There are 2 possible settings (0 or 1) for each of the 5 P and T variables in the upper box 1002, and 2 possible settings (0 or 1) for each of the 5 P and T variables in the lower box. The possible combinations of the T and P values are therefore $2^5 * 2^5 = 1024$.

At 1106, based on the computed probabilities, the settings of transition variables T and P across the entire chromosome sequence (i.e., for i=1, L) are searched to determine the settings that would most likely result in the observed values. In some embodiments, the determination is made using a dynamic programming technique such as Viterbi, and $2^5 * 2^5 * L$ states are searched.

At 1108, the setting of H variables is looked up across the entire sequence to determine the settings that would most likely result in the given G, P, and T variables. This requires L table lookups.

The trio-based phasing solves the most likely settings for the H variables (the hidden true alleles for the individual's maternal and paternal haplotypes at a given location). The solution is useful for phasing the child's DNA sequence information as well as for phasing a parent's DNA sequence information (if the parent's DNA sequence information is unphased initially). In the event that only one parent's DNA sequence information is available, the other parent's DNA sequence information can be partially determined based on the DNA sequence information of the known parent and the child (e.g., if the child's alleles at a particular location is "AC" and the mother's alleles at the same location are "CC", then one of the father's alleles would be "A" and the other one is unknown). The partial information can be marked (e.g., represented using a special notation) and input to the model. The quality of trio-based phasing based on only one parent's information is still higher than population-based phasing without using the trio-based method.

In addition to improved haplotypes data, the result of trio-based phasing also indicates whether a specific allele is deemed to be inherited from the mother or the father. This information is stored and can be presented to the user in some embodiments.

Correcting Phased Genotype Data

In certain embodiments, phased genotype data is processed using one or more tools configured to account for and/or correct genotyping errors and/or phase switch errors. In some cases, a positional Burrows-Wheeler transform (PBWT) such as a templated PBWT routine is used to account for genotype errors and/or correct phasing errors. Examples of templated PBWT routines are described in PCT Patent Application No. PCT/US2020/042628, filed Jul. 17, 2020, which is incorporated herein by reference in its entirety. In some implementations, Hidden Markov Models and/or one or more heuristics are used to identify and correct phase switch errors or phased genotype errors. In some implementations, Hidden Markov Models and/or one or more heuristics are incorporated into the TPBWT or used sequentially with the TPBWT to identify and correct phase switch errors or phased genotype errors. Examples of phase-switch error correction routines are also described in PCT Patent Application No. PCT/US2020/042628, filed Jul. 17, 2020, previously incorporated herein by reference in its entirety. In various embodiments, genotype data from an individual is processed using one or more of these correction routines prior to performing local classification on the genotype data.

Local Classification

Local classification refers to the classification of DNA segments as originating from an ancestry associated with a specific geographical region (e.g., Eastern Asia, Scandinavia, etc.) or ethnicity (e.g., Ashkenazi Jew).

Local classification is based on the premise that, T generations ago, all the ancestors of an individual were unadmixed (i.e., originating from the same geographical region). Starting at generation 1, ancestors from different geographical regions produced admixed offspring. Genetic recombination breaks chromosomes and recombines them at each generation. After T generations, 2T meiosis occurred. As a result, the expected length of a recombination-free segment is expressed as:

$$L = \frac{F}{2T} cM$$

where F corresponds to a segment 100 cM in length. In some embodiments, the expected length L is taken to be the recombination distance corresponding to 100 SNPs. In some embodiments 100 SNPs are used as the window size. This length is typically much smaller than the expected length, L. For a typical T of 5 generations we obtain L as 10 cM, which is roughly 10 MB. This is much longer than the 100 SNP windows.

Figure 12:
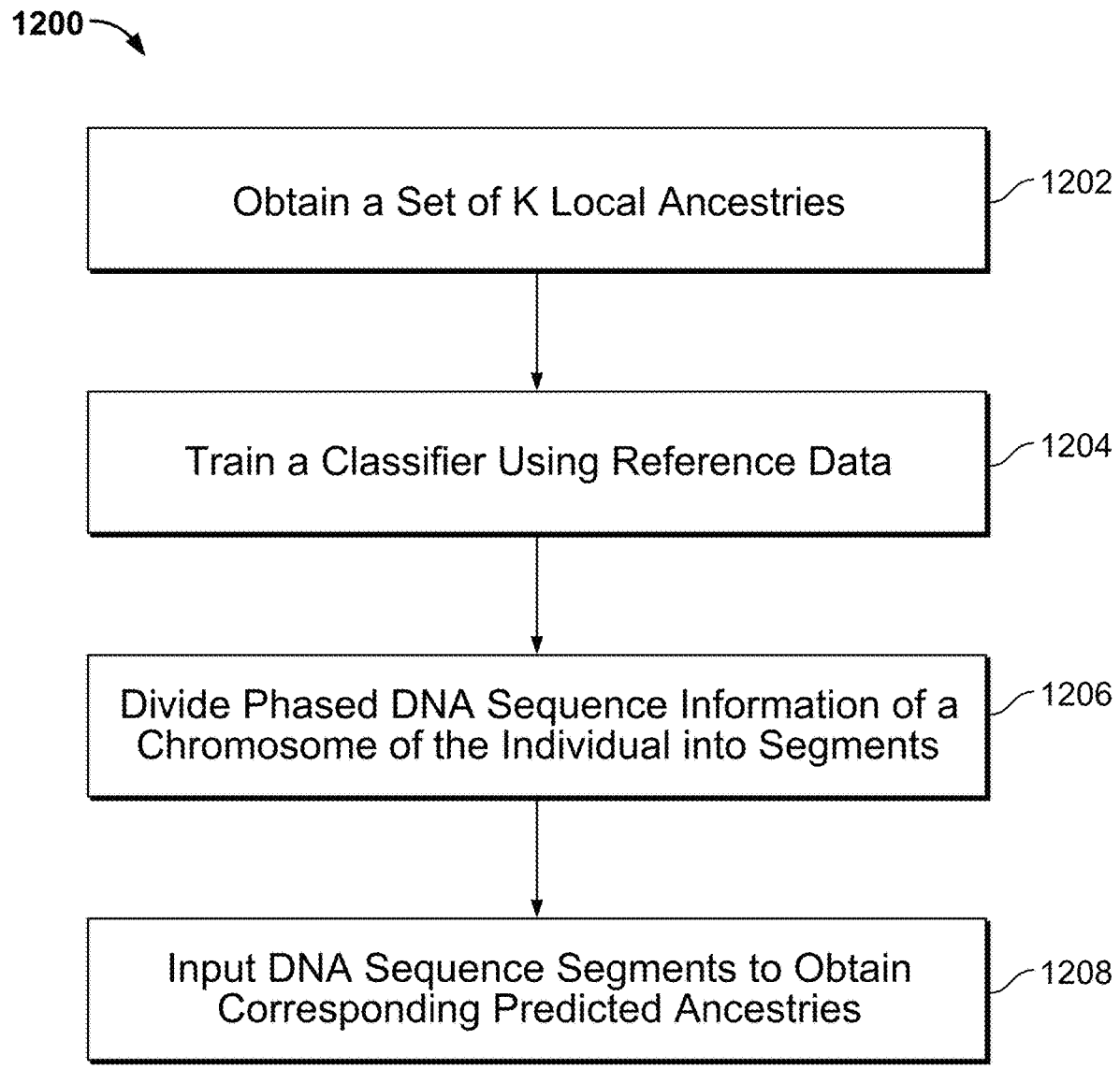
FIG. 12 is a flowchart illustrating an embodiment of a local classification process.

FIG. 12 is a flowchart illustrating an embodiment of a local classification process. Process 1200 can be performed on a platform such as 200 or a system such as 300.

Initially, at 1202, a set of K ancestries is obtained. In some embodiments, the specification of the ancestries depends on the ancestries of unadmixed individuals whose DNA sequence information is used as reference data. For example, the set of ancestries can be pre-specified to include the following: African, Native American, Ashkenazi, Eastern Asian, Southern Asian, Balkan, Eastern European, Western European, Middle Eastern, British Isles, Scandinavian, Finnish, Oceanian, Iberian, Greek, Sardinian, Italian, and Arabic. Many other specifications are possible; for example, in some embodiments the set of ancestries correspond to individual countries such as the UK, Ireland, France, Germany, Finland, China, India, etc. In some cases the set of ancestries can include sub-regions in countries, for example Northern Italy, Southern Italy, etc. or cultural groups such as Copt.

An example of a more extensive list of ancestries includes: Senegal, The Gambia & Guinea; Sierra Leone, Liberia, Ivory Coast & Ghana; Nigeria; Sudan; Ethiopia & Eritrea; Somalia; Congo; South and East Africa; Biaka, Mbuti & San; Japan; Korea; China; Chinese Dai; Vietnam; Philippines & Austronesia; Myanmar, Thailand, Cambodia & Indonesia; Mongolia & Manchuria; Siberia; Americas; Melanesia; Central Asia; Northern India & Southern Pakistan; Bengal & Northeast India; Gujarat Patel; Southern Brahmin; Southern India Other & Sri Lanka; Kerala; Cyprus; Turkey; Caucasus, Assyria & Iran; Arabia; Levant; Egypt Other; Copt; Maghreb; Britain & Ireland; Central & West Europe; Scandinavia; Finland; Spain & Portugal; Sardinia; Italy; Balkans & Greece; East Europe; and Ashkenazi Jewish.

At 1204, a classifier is trained using reference data. In this example, the reference data includes DNA sequence information of unadmixed individuals, such as individuals who are self-identified or identified by the system as having four grandparents of the same ancestry (i.e., from the same region), DNA sequence information obtained from public databases such as 1000 Genomes, HGDP-CEPH, HapMap, etc. The DNA sequence information and their corresponding ancestry origins are input into the classifier, which learns the corresponding relationships between the DNA sequence information (e.g., DNA sequence segments) and the corresponding ancestry origins. In some embodiments, the classifier is implemented using a known machine learning technique such as a support vector machine (SVM), a neural network, etc. A SVM-based implementation is discussed below for purposes of illustration.

At 1206, phased DNA sequence information of a chromosome of the individual is divided into segments (also sometimes referred to as windows or blocks). In some embodiments, phased data is obtained using the improved phasing technique described above. Phased data can also be obtained using other phasing techniques such as BEAGLE (S R Browning and B L Browning (2007) Rapid and accurate haplotype phasing and missing data inference for whole genome association studies by use of localized haplotype clustering. Am J Hum Genet 81:1084-1097. doi: 10.1086/521987), which is incorporated herein by reference in its entirety. In some implementations EAGLE (Po-Ru Loh, Petr Danecek, Pier Francesco Palamara, Christian Fuchsberger, Yakir A Reshef, Hilary K Finucane, Sebastian Schoenherr, Lukas Forer, Shane McCarthy, Goncalo R Abecasis, Richard Durbin and Alkes L Price, "Reference-based phasing using the Haplotype Reference Consortium panel," Nature Genetics, 2016, 48(11), 1443-1450.), which is incorporated herein by reference in its entirety, is used for obtaining phased data. The length of the segments can be a predetermined fixed value, such as 100 SNPs. It is assumed that each segment corresponds to a single ancestry.

At 1208, the DNA sequence segments are input into the trained classifier to obtain corresponding predicted ancestries. In some embodiments, the classifier determines probabilities associated with the set of ancestries (i.e., how likely a segment is from a particular ancestry), and the ancestry associated with the highest probability is selected as the predicted ancestry for a particular segment.

In some embodiments, one or more SVMs are used to implement the classifier. An SVM is a known type of non-probabilistic binary classifier. It constructs a hyperplane that maximizes the distance to the closest training data point of each class (in this case, a class corresponds to a specific ancestry). A SVM can be expressed using the following general expression:

$$\begin{cases} \min_{w, \xi, b} \frac{1}{2} \|w\|^2 + C \sum_i \xi_i \\ y_i(w * x_i - b) \geq 1 - \xi_i \, \forall \, i \\ \xi_i \geq 0 \, \forall \, i \end{cases}$$

where w is the normal vector to the hyperplane, C is a penalty term (fixed), the $\xi$ are slack variables, $x_i$ represents the features of the data point i to be classified, and $y_i$ is the class of data point i.

Figure 13:
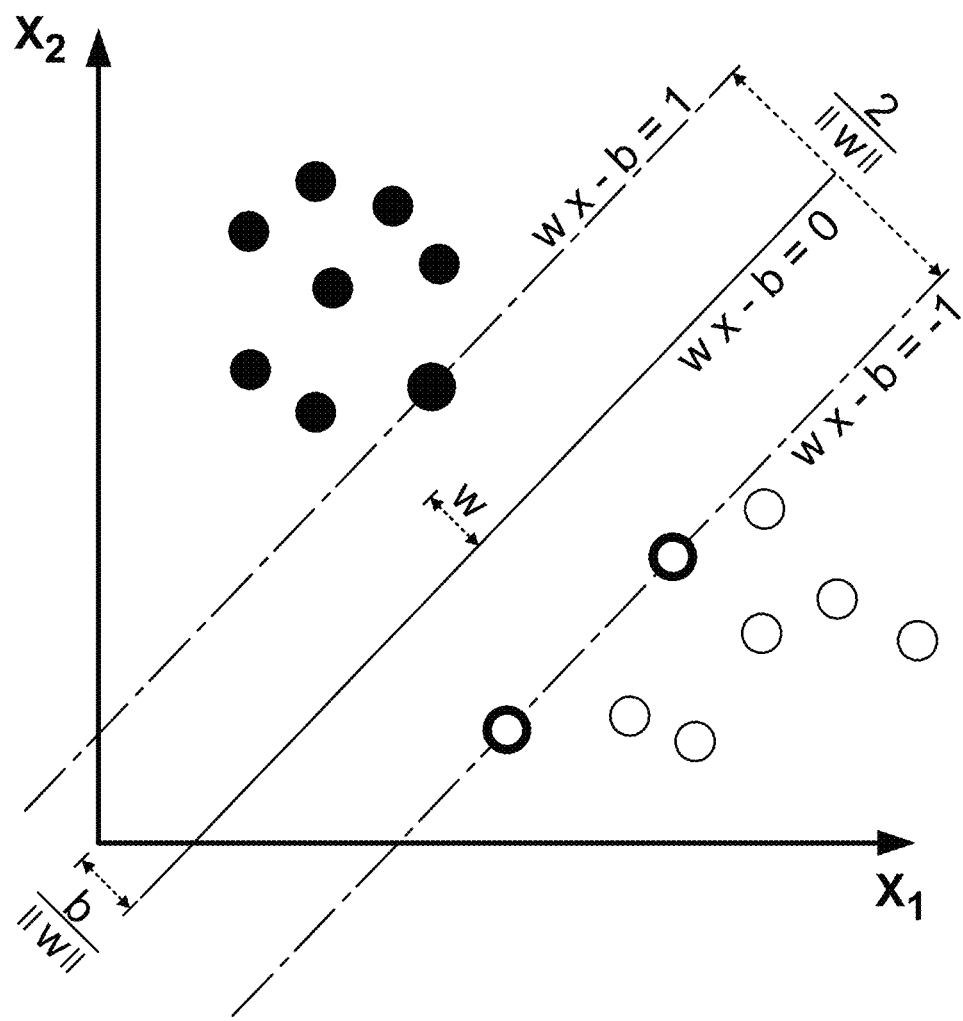
FIG. 13 is a diagram illustrating how a set of reference data points is classified into two classes by a binary SVM.

FIG. 13 is a diagram illustrating how a set of reference data points is classified into two classes by a binary SVM.

Since a SVM is a binary classifier and there are K (e.g., 45 or greater) classes of ancestries to be classified, the classification can be decomposed into a set of binary problems (e.g., should the sequences be classified as African or Native American, African or Ashkenazi, Native American or Ashkenazi, etc.). One approach is the "one vs. one" technique where a total of $\binom{K}{2}$ classifiers are trained and combined to form a single ancestry classifier. Specifically, there is one classifier configured to determine the likelihood that a sequence is African or Native American, another to determine African or Ashkenazi, another to determine Native American or Ashkenazi, etc. During the training process, reference data of DNA sequences and their corresponding ancestries is fed to the SVM for machine learning. When an ancestry prediction for a DNA sequence segment is to be made, each trained SVM makes a determination about which one of the ancestry pair the DNA sequence segment more likely corresponds to, and the results are combined to determine which ancestry is most likely. Specifically, the ancestry that wins the highest number of determinations is chosen as the predicted ancestry. Another approach is the "one vs. all" technique where K classifiers are trained.

Several refinements can be made to improve the SVM. For example, the number of unadmixed reference individuals can vary greatly per ancestral origin. If 700 samples are from Western Europe but only 200 samples are from South Asia, the imbalance in the number of samples can cause the Western European-South Asian SVM to "favor" the larger class. Thus, the larger class is penalized to compensate for the imbalance according to the following:

$$\begin{cases} \min_{w,\xi,b} \frac{1}{2}\|w\|^2 + \sum_G C_G \sum_i \xi_i \\ y_i(w*x_i - b) \geq 1 - \xi_i \,\forall\, i \\ \xi_i \geq 0 \,\forall\, i \end{cases}$$

$$C_G \propto \frac{1}{|G|}$$

where w is the normal vector to the hyperplane, CG is a penalty term for class G, the $\xi$ are slack variables, $x_i$ represents the features of the data point i to be classified, and $y_i$ is the class of data point i.

Another refinement is to encode strings of SNPs according to the presence or absence of features. One approach is to encode one feature at each SNP according to the presence or absence of the minor allele. Another approach is to take substrings of length 2 which have 4 features per position and which can be encoded based on their presence or absence as 00, 01, 10, and 11. A more general approach is to use a window of length L, and encode $(L-k+1)\cdot 2^k$ features of length k according to the presence or absence of the features.

The general approach is not always feasible for practical implementation, given that there are $$\sum_{k=1}^{100}(L-k+1)\times 2^k$$

features in a window of length L. With L=100, this number is approximately $10^{30}$, too large for most memory systems. Thus, in some embodiments, a modified kernel is used. In some embodiments, a specialized string kernel is used that computes the similarity between any two given windows as the total number of substrings they share. This approach takes into account that even very similar windows contain sites that have mutated, resulting in common subsequences along with deleted, inserted, or replaced symbols. Therefore, the specialized string kernel is a more relevant way of comparing the similarity between two 100 SNP windows, and achieves much higher accuracy than the standard linear kernel.

Another refinement is to use supervised learning. Supervised learning refers to the task of training (or learning) a classifier using a pre-labeled data, also referred to as the training set. Specifically, an SVM classifier is trained (or learned) using a training set of customers whose ancestry was known (e.g., self-reported ancestries). Parameters of the SVM classifier are adjusted during the process. The trained classifier is then used to predict a label (ancestry) for any new unlabeled data.

In some implementations, the classification process ignores SNPs near chromosome centromeres. In some implementations, groups of SNPs are ignored based on proximity to centromeres. Such groups may be defined by proximity to the centromere, on a chromosome-by-chromosome basis. In some implementations, windows (segments) are constructed such that no window spans a centromere.

While local classification has been described as being implemented using an SVM classifier, the disclosed embodiments are not so limited. As examples, random forests, gradient-boosting techniques, and neural networks such as recurrent neural networks may be used as local classifiers in place of (or in addition to) SVM classifiers. Replacements of the SVM classifier also include methods that classify ancestry in a window by identifying a genealogically-related copy of all or part of the window in an individual whose ancestry is known. This can be done through methods that identify identical-by-descent DNA segments, for example the methods described in PCT Patent Application No. PCT/US2020/042628, filed Jul. 17, 2020, previously incorporated herein by reference in its entirety. The ancestry of the related copy can then be used to classify the ancestry in the window.

Example of Local Classification

A task of the local classifier is to assign each marker along each haplotype to one of K reference populations. The local classifier starts by splitting each haplotype into S windows of M biallelic markers. Each window is treated independently and is assumed to have a single ancestral origin. Thus, for each haplotype, the local classifier returns a vector c[1:S], where vector element ci, i∈{1 . . . K} is the hard-clustering value assigned to window i. In some cases, the local classifier is implemented using a discriminative classifier such as string-kernel support vector machines.

An SVM is a non-probabilistic binary linear classifier. That is, it learns a linear decision boundary that can be used to discriminate between two classes. SVMs can be extended to problems that are not linearly separable using the soft-margin technique.

Consider a set of training data $\{(x_i, y_i)\}1:N$, where $x_i$ is a feature vector in $R^d$ and $y_i$, i∈{0, 1} is a class label. The SVM learns the decision boundary by solving the following quadratic programming optimization problem (eq. 1):

$$\min_{w\in R^d, \xi\in R^N, b\in R} \frac{1}{2}\|w\|^2 + C\sum_{i=1}^{N}\xi_i \qquad \text{(eq. 1)}$$

$$\text{subject to } \begin{cases} y_i(w^T x_i - b) \geq 1 - \xi_i \,\forall\, i \\ \xi_i \geq 0 \end{cases}$$

C is a tuning parameter that, in practice, we generally set to 1.

To encode feature vectors, each feature vector $x_i$ may represent the encoding of a haplotype window of M biallelic markers from a prephased haplotype. One natural encoding is to use one feature per marker, with each feature encoding the presence/absence of the minor allele. However, this encoding may fail to capture the spatial relationship of consecutive markers within the window (i.e., the linkage pattern), a distinguishing feature of haplotypes. Instead, some implementations use every possible k-mer (k∈{1 . . . M}) as features. For a haplotype segment of M biallelic markers, there are $$d = \sum_{k=1}^{M}(M-k+1)2^k$$

possible k-mers. When M=100, d is on the order of 10^10, so it may not be feasible to directly construct feature vectors with this many dimensions. A subsequent section introduces a string kernel that enables working with high-dimensional feature set.

A feature of SVMs is that solving (eq. 1) is equivalent to solving the dual quadratic programming problem (eq. 2):

$$\max_{\alpha \in R^N} \sum_{i=1}^{N}\alpha_i - \frac{1}{2}\sum_{i,j=1}^{N}\alpha_i\alpha_j y_i y_j x_i^T x_j \quad \text{(eq. 2)}$$

$$\text{subject to } \begin{cases} 0 \le \alpha_i \le C \\ \sum_{i=1}^{N}\alpha_i y_i = 0 \end{cases} \forall i$$

The dual representation of the SVM optimization problem depends only on the inner product $x_i^T x_j$, allowing for the introduction of kernels. Kernels provide a way to map observations to a high-dimensional feature space, thereby offering an enormous computational advantage, as they can be evaluated without explicitly calculating feature vectors. Denoting $\chi$ the input space and $\varphi$: $\chi \to \{0,1\}^d$ the mapping such that for any segment x of length M, $\varphi(x)$ is the vector whose elements denote the presence or absence of each of the d possible k-mers in x, we define a string kernel as, $\forall i, j \in \{1, \ldots, N\}$, $$K(x_i, x_j) = \phi(x_i)^T\phi(x_j) = \sum_{k=1}^{M}\sum_{l=1}^{M-k+1}\mathbf{1}\{u_{kli} = u_{klj}\} \quad \text{(eq. 3)}$$

where $u_{kli}$ is the k-mer starting at position 1 in haplotype window i. The kernel is a special case of the weighted degree kernel. Standard dynamic programming techniques can be used to evaluate $K(x_i, x_j)$ in O(M) operations without explicitly enumerating the d features for each mapped input vector. Thus, the string kernel enables the procedure to extract a large amount of information from each haplotype window without explicitly computing feature vectors.

SVMs are binary classifiers, but ancestry composition is concerned with deciding not between two but between many more (e.g., 45) possible populations. To assign a single hard-clustering value k∈{1, . . . , K} to a haplotype window, an example method trained 2 classifiers, one for each pair of populations. It then assigned the haplotype to a single population using a straightforward majority vote across all pairs.

Training Data

One example involved training a local classifier on ~14,400 unrelated individuals, each with unadmixed ancestry from one of K=45 reference populations. This reference panel included ~11,800 research-consented 23andMe customers, ~600 individuals from non-customer 23andMe datasets, and 2000 individuals from publicly available datasets, including the 1000 Genomes Project (The 1000 Genomes Project Consortium, 2015) and the Human Genome Diversity Panel.

To ensure that all the reference individuals were no closer than distantly related, the training used the method described in U.S. Pat. No. 8,463,554, issued Jun. 11, 2013 (incorporated herein by reference in its entirety) to estimate identity-by-descent (IBD) sharing between each pair of individuals and removed individuals from the sample until no pair shared more than an 100 cM. The training then conducted principal components analysis (PCA) and uniform manifold approximation and projection to identify population structure, which, when paired with survey data and analyzed jointly with the well-curated external reference panels, enabled definition of 45 reference populations and allowed outliers to be flagged for removal. IBD estimation may also be done by methods described in PCT Patent Application No. PCT/US2020/042628, filed Jul. 17, 2020, previously incorporated herein by reference in its entirety.

For most reference populations, the research-consented 23andMe customers reported in survey responses that their four grandparents were born in a single country. For regions with large multiethnic countries (e.g., South Asia), it was required that an individual's four grandparents either spoke a single regional language or were born in one state. Free-text responses on grandparental national, ethnic, religious, or other identities enabled construction of reference panels for populations not defined by specific geographic regions (e.g., Ashkenazi Jews).

Window Size

An assumption of the local classifier is that the haplotype segment within each window derives from a single population. Thus, the window-size parameter influences the timing of the admixture that can be addressed. For example, if a classifier sought only to infer "local" admixture in first-generation admixed individuals, then windows could potentially span entire chromosomes. More generally, if a simple admixture model is assumed in which the most recent ancestor of an individual who was fully from a reference population lived T generations ago, then the expected length of a segment of single ancestry is 100/(2T) cM.

Phasing switch errors also limit the size of segments we can consider. If a switch error occurs within a haplotype window, the assumption that the haplotype segment within the window has a single ancestry may no longer be valid. Thus, it is necessary to choose a window size small enough to ensure that most windows are free of switch errors. On the other hand, longer windows contain more information, which increases the power of the SKSVM to separate reference populations.

Certain embodiments herein employ a window size of 300 markers. This corresponds to ~0.6 cM per window and, on a genotyping platform measuring ~540,000 markers, divides the genome into ~1800 windows. This window size was found to provide a good balance between retaining ancestry-related information within windows and precluding recombination events and phasing errors within them. In other embodiments, the window size may be at least about 100 markers, at least about 200 markers, at least about 300 markers, at least about 400 markers, or at least about 500 markers.

Error Correction

Figure 14:
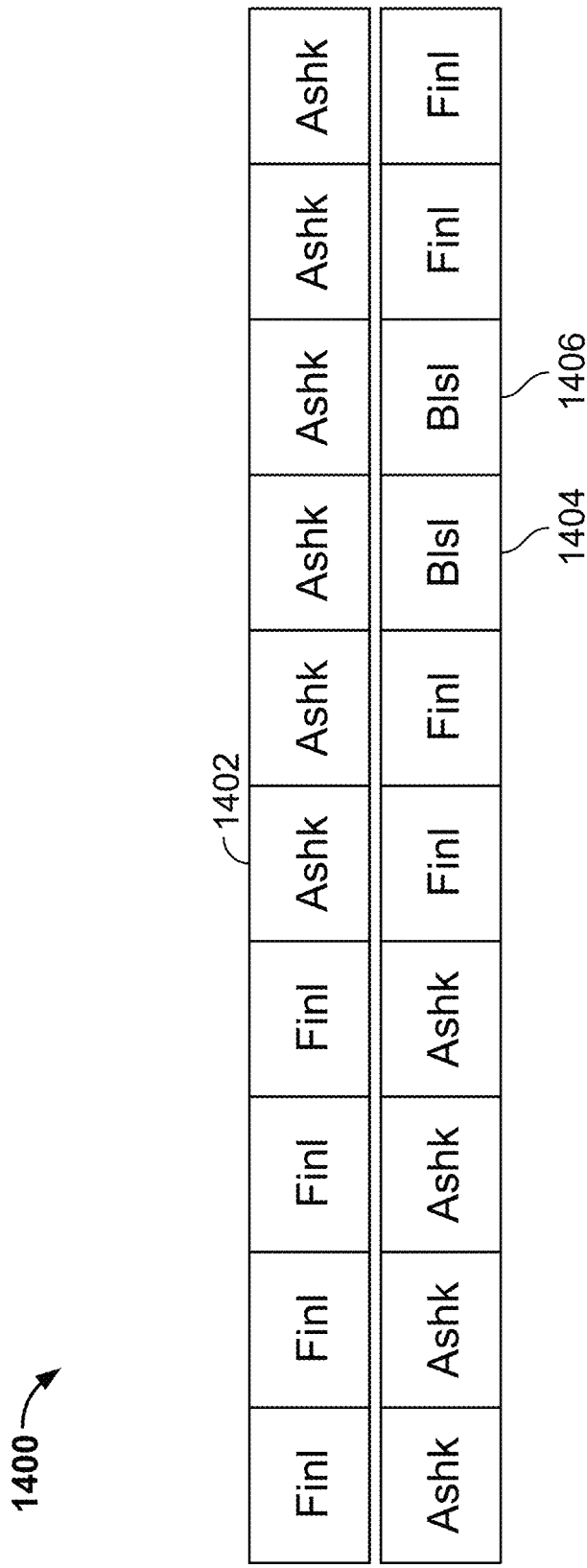
FIG. 14 is a diagram illustrating possible errors in an example classification result.

The results of the local classifier can contain errors. FIG. 14 is a diagram illustrating possible errors in an example classification result. In this example, a portion of an individual's DNA sequence is phased and locally classified. The classification result 1400 is shown, in which the top portion corresponds to the haplotype inherited from one parent and the bottom portion corresponds to the haplotype inherited from the other parent. Each segment of the individual's DNA is labeled according to the local classifier output as Finland, Ashkenazi, or British Isles. Two types of possible errors are illustrated. Starting at location 1402, the label switched from Finland to Ashkenazi for the first half of the chromosome and from Ashkenazi to Finland for the second half. This switch can be caused by a double transition in ancestry or a single phasing error. At locations 1404 and 1406, there are two predictions for segments that correspond to British Isles ancestry. These repeated predictions can be evidence of ancestry changes, or be caused by correlated local classifier (e.g., SVM) prediction errors. Thus, error correction is implemented in some embodiments. In addition, because the output of the SVM tends to be noisy, the error correction process also reconciles these ancestry estimates and produces cleaner classifications (i.e., smooths out the noise). In some embodiments, confidence scores for the ancestry assignments are also computed.

Figure 15:
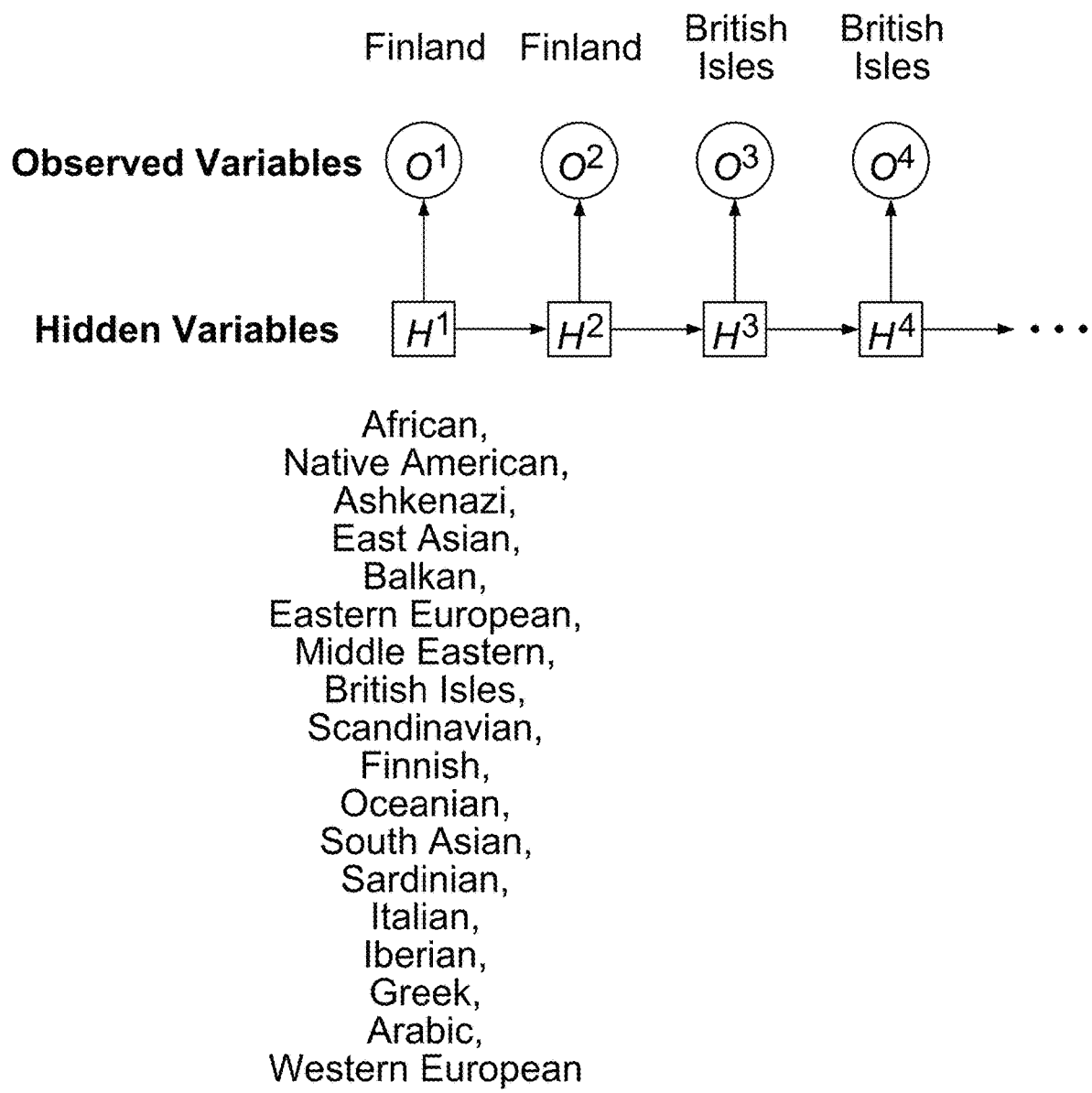
FIG. 15 is a graph illustrating embodiments of Hidden Markov Models used to model phasing errors.

In some embodiments, error correction or "smoothing" is implemented using a Hidden Markov Model (HMM), which is a statistical model in which the input data is being modeled as a Markov process with unobserved (hidden) states. In an HMM, the observed signal (the input data) is being generated by a hidden process in a sequential manner. A standard HMI assumes that an observation, given the hidden state that generated it, is independent of all previous observations. The hidden state at any given position only depends on the hidden state at the previous position. In some embodiments, the input (observed data) to the HMM includes the predicted ancestries of DNA sequence segments (e.g., the ancestries as predicted by the local classifier for segments that are 100 SNPs in length). The hidden state corresponds to the true ancestries of the segments. The output of the HMM forms a set of smoothed ancestry origins for the segments. FIG. 15 is a graph illustrating embodiments of Hidden Markov Models used to correct model phasing errors. In the example shown, the observed variables $O^1$, $O^2$, $O^3$, and $O^4$ correspond to Finland, Finland, British Isles, and British Isles, respectively. The possible values for each hidden state H correspond to the set of ancestries. Given the observed variables and the probabilities associated with the model, the most likely sequence of hidden states can be obtained.

Figure 16:
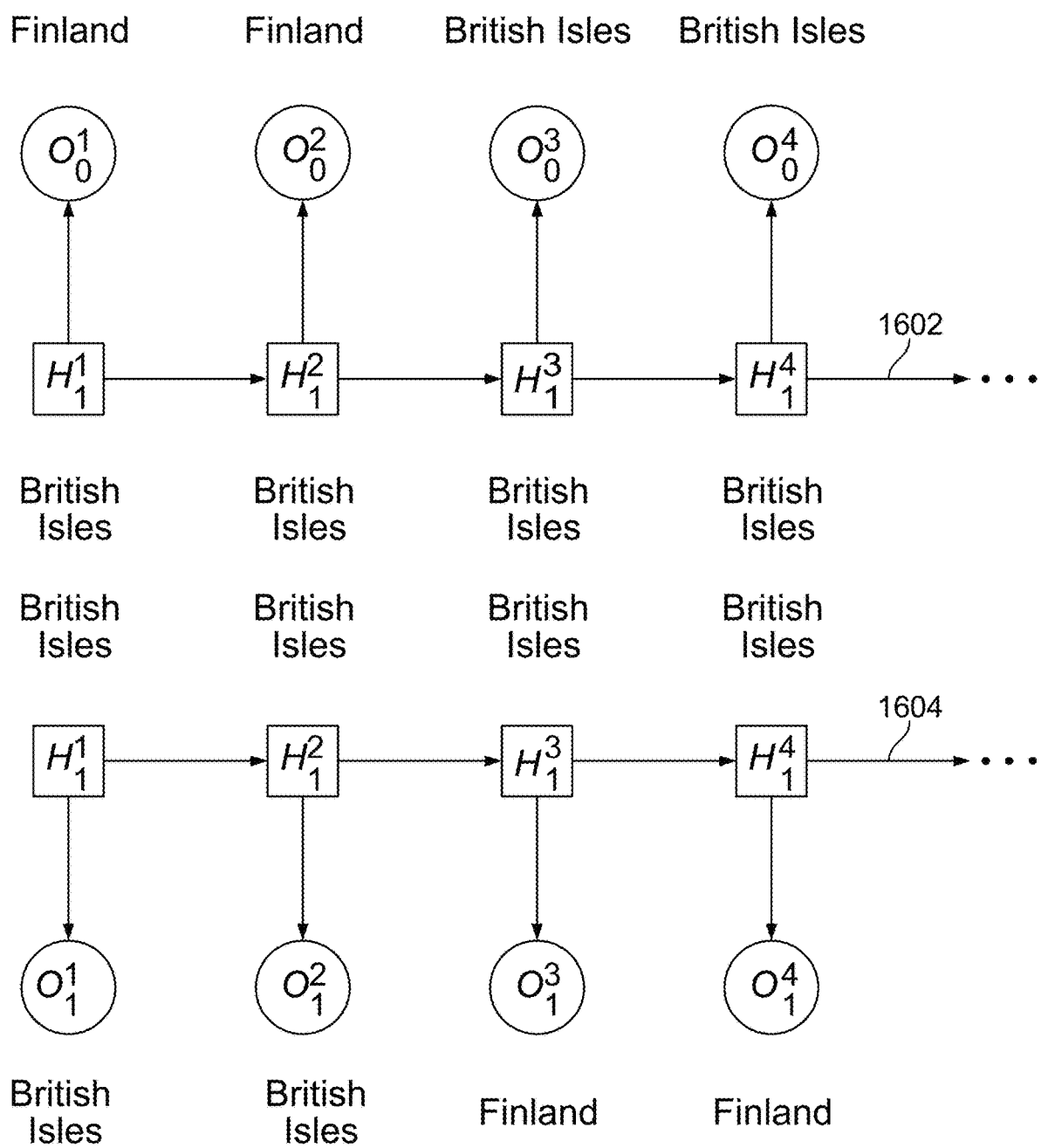
FIG. 16 shows two example graphs corresponding to basic HMIs used to model phasing errors of two example haplotypes of a chromosome.

FIG. 16 shows two example graphs corresponding to basic HMIs used to model phasing errors of two example haplotypes of a chromosome. In this example, graph 1602 illustrates an HMM corresponding to one haplotype and graph 1604 illustrates an HMI corresponding to another haplotype. The most likely sequences of the H variables have been solved and the H variables are labeled.

Figure 17:
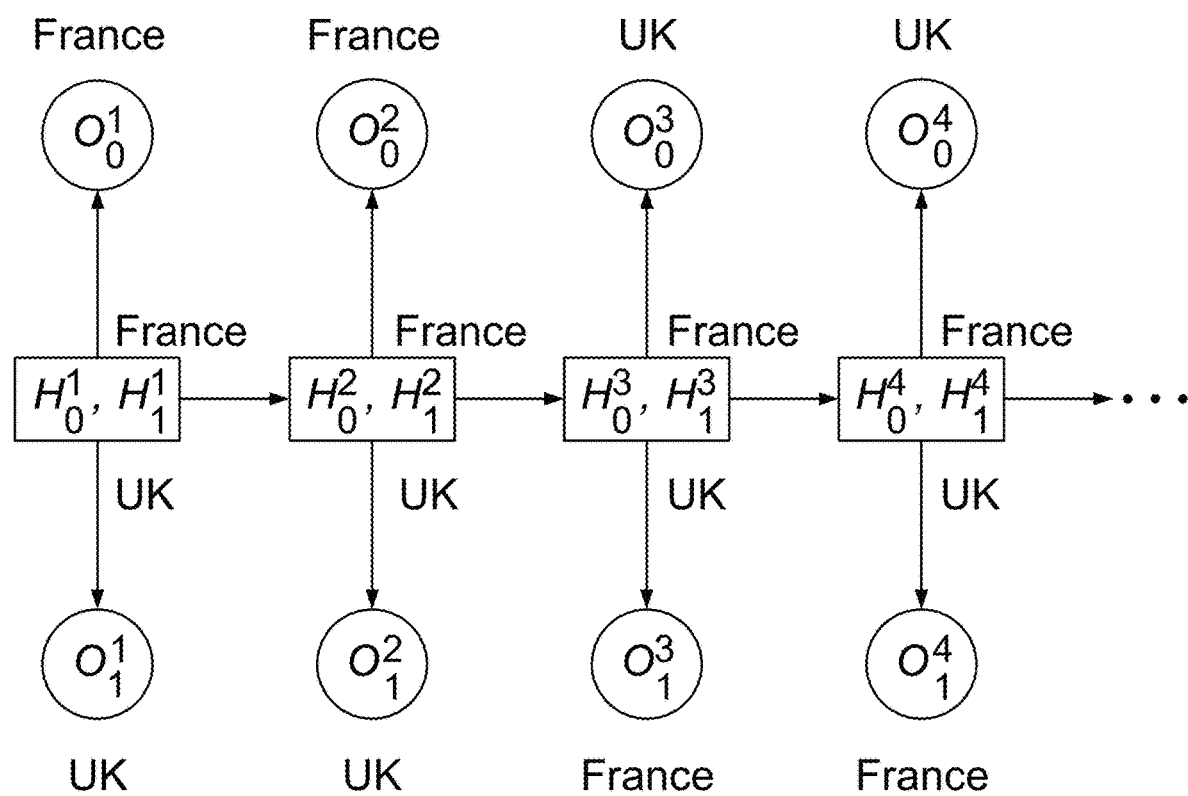
FIG. 17 is an example model of the interdependencies between observed states.

The basic model averages out the output of the learning machine and generates a smoother and less noisy output but does not correct many of the errors in the output. For example, in FIG. 16, two HMIs model two haplotypes separately and independently. In practice, however, the switching errors in two haplotypes are not independent but instead occur together. Thus, in some embodiments, the basic HMI is improved by treating the true ancestries associated with two haplotypes at a given location as a single hidden state. FIG. 17 shows an example graph in which one HMM jointly models both haplotypes to account for potential phasing errors. This model is referred to as a Pair Hidden Markov Model (PHMM). In this case, the pair of true ancestries of both haplotypes at a given location is treated as the hidden state at the location. The PHMM accounts for the phasing errors (e.g., error at location 1402 of FIG. 14) that are present in the output of the local classifier.

Figure 18:
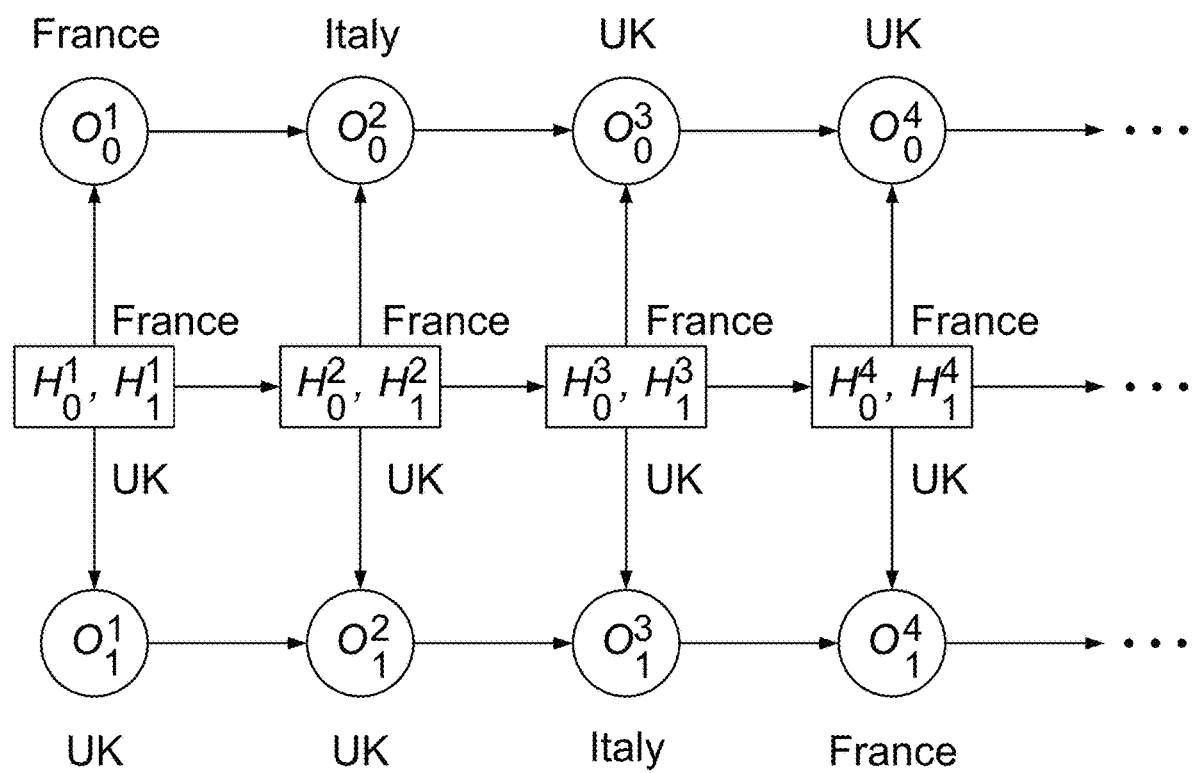
FIG. 18 is an example graph of an Autoregressive Pair Hidden Markov Model (APHMM).

Also, in FIG. 16, the basic HMMs assume that the observed data are computed independently (in other words, the Os are uncorrelated). In practice, the classification errors are correlated. For example, since long stretches of DNA can be inherited from one generation to the next, the true ancestries of adjacent DNA segments can be correlated. Thus, in some embodiments, the model of FIG. 17 is further improved to model the interdependencies between observed states. The improved model is another type of PHMM, referred to as an Autoregressive Pair Hidden Markov Model (APHMM). FIG. 18 shows an example graph of an Autoregressive Pair Hidden Markov Model (APHMM). In this example, a given observed state $O^i$ depends both on its corresponding underlying hidden state H i and on the previous observed state $O^{i-1}$.

The graph defines a probabilistic model as follows:

$$Pr(H^1, H^2, H^3, \ldots, O^1, O^2, O^3, \ldots) = Pr(H^1)Pr(O^1|H^1)$$
$$Pr(H^2|H^1)Pr(O^2|H^2, O^1)Pr(H^3|H^2)$$
$$Pr(O^3|H^3, O^2) \ldots$$

where probabilities $P(O^j|H^j, O^{j-1})$ are referred to as the emission parameters, and probabilities $Pr(H^i|H^{i-1})$ are referred to as the transition parameters.

The model outputs probabilities associated with ancestry assignments of the most probable sequence. Training is required to estimate the emission parameters and the transition parameters. In some embodiments, an expectation maximization method is used to estimate the parameters.

The emission parameters characterize how well the local classifier predicts the ancestry. Specifically, given the underlying true state of a segment, what is the probability that the local classifier will output the true state. FIG. 19 is an example data table displaying the emission parameters. The data table can be generated based on empirical data of the local classifier's output and reference data of unadmixed individuals. For example, suppose there are 1000 individuals in the reference population who have identified themselves as unadmixed Ashkenazis. The local classifier output, however, labels 1% of these individuals' segments as African, 3% as Native American, 40% as Ashkenazi, etc. Thus, P (O=African|H=Ashkenazi) is 1%, P (O=Native American|H=Ashkenazi) is 3%, P (O=Ashkenazi|H=Ashkenazi) is 40%, etc. These values are used to fill the corresponding entries in the table. The values for emission parameters are found along the diagonal of the table.

The transition parameters correspond to the probability of a particular hidden state of the model given the previous hidden state. They represent the statistical likelihood of observing certain sequences of true ancestries in the population, and therefore need to be determined based on admixed data. However, in real data, a given individual's true ancestries are unknown. Therefore, it is not possible to obtain fully transitioned and accurately labeled genomes from actual admixed individuals. Thus, to determine the transition parameters, an iterative approach is used. Initially, the transition parameters are arbitrarily chosen to establish an initial model. The initial model is used to perform error correction. Based on the error corrected results, the model is updated by applying an expectation maximization method. The process can be repeated until a final convergent model is achieved.

A further mathematical explanation of techniques for generating emission and transition parameters is provided below. In some portions of this disclosure, the hidden and observed states are referred to with x, y, respectively, rather than as H, O, respectively. Examples of forward and backward recursions can also be found in Rabiner et al "A Tutorial on Hidden Markov Model and Selected Applications in Speech Recognition" 1989, which is incorporated herein by reference in its entirety.

In some embodiments, smoothing models, such as HMMs as described herein, are trained using ancestry classification data from at least about 100 individuals, or at least about 1000 individuals, or at least about 10,000 individuals. In some cases, multiple smoothing models are trained and deployed for smoothing ancestry classification results of individuals. As an example, one model is trained or optimized using ancestry classification results from individuals of a first ancestry, a second model is trained or optimized using ancestry classification results from individuals of a second ancestry, and so on if necessary. The different ancestries (the first ancestry, the second ancestry, and so on) may be based on broad or narrow categories such as, for example, Northern European versus Scandinavian or British Isles. In some implementations, the posterior probabilities (i.e., smoother module outputs) are computed as ensemble averages across outputs from the multiple smoothing models. In some implementations, the ensemble averages are weighted based on which models are deemed to most closely correspond to the ancestry classifications of the individual under consideration. This may be based on a likelihood analysis, with parameters of models having a greater likelihood of corresponding to the individual under consideration given greater weights in the ensemble. In some embodiments, a separate ensemble of HMMs is applied to ancestry classifications from each chromosome. In some embodiments, a single HMM is applied to ancestry classifications from all chromosomes. As examples, the number of error correction models from which the ensemble parameters are derived is at least 2, or at least 5, or about 5 to 20.

Once the emission parameters and the transition parameters are established, the model is fully specified. Thus, the most likely sequence of hidden variables can be determined based on the observed states using conventional HMM techniques. For example, a probabilistic scoring scheme is used to determine the most likely sequence in some embodiments. All the possibilities associated with the hidden states are listed, and a set of scoring rules are specified to reward or penalize certain events by adding or subtracting a score associated with a sequence. For example, a change in adjacent haplotypes is likely an error; therefore, whenever two adjacent haplotypes are different, the score is reduced according to the rules. A mismatched observed state/hidden state pair also indicates likely error; therefore, whenever there is a mismatch of predicted ancestry and the underlying ancestry, the score is reduced. The most likely sequence of hidden states can be determined by computing scores associated with all possible combinations of observed states and hidden states, and selecting the sequence that leads to the highest score. In some embodiments, more efficient techniques for selecting the most likely sequence such as dynamic programming are employed to break the problem down into subproblems and reduce the amount of computation required. For example, the problem can be reduced to recursively determine the best ancestry assignment for everything to the left or the right of a particular position.

As described above, training is required to obtain parameters for the PHMM (or APHMM). In some embodiments, an ensemble technique is used where the reference population is grouped into distinct subsets to serve as different types of training data resulting in different types of models. For example, different types of reference individuals that tend to have similar ancestries are identified and grouped into subsets. Such subsets can be formed from admixed individuals (e.g., Latinos, Eurasians, etc.) as well as unadmixed individuals (e.g., East Asians, Northern Europeans, etc.). Data from a subset is used to determine the parameters of the model for that subset. The resulting model is a model specific to the reference group (e.g., a Latino-specific model, a Eurasian-specific model, an East Asian specific-model, a Northern European-specific model, etc.). In some embodiments, the error correction process applies its input to all available models, and the results are weighted based on confidence measures and then combined according to a Bayesian model averaging technique.

Figure 20A:
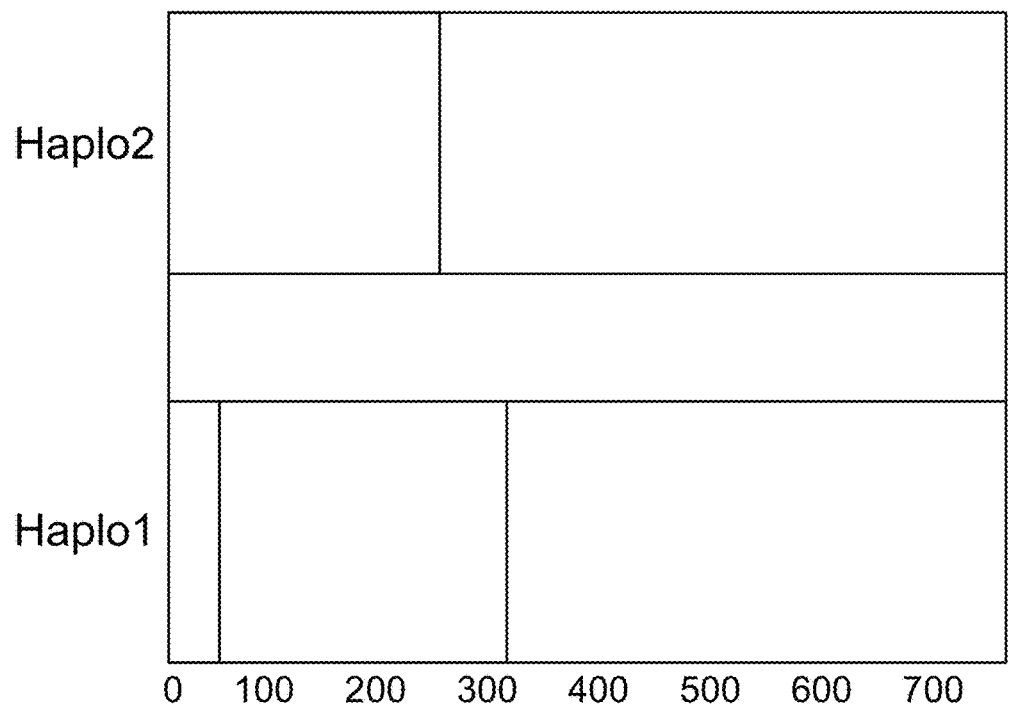
FIGS. 20A-20D are example ancestry assignment plots illustrating different results that are obtained using different techniques.
Figure 20B:
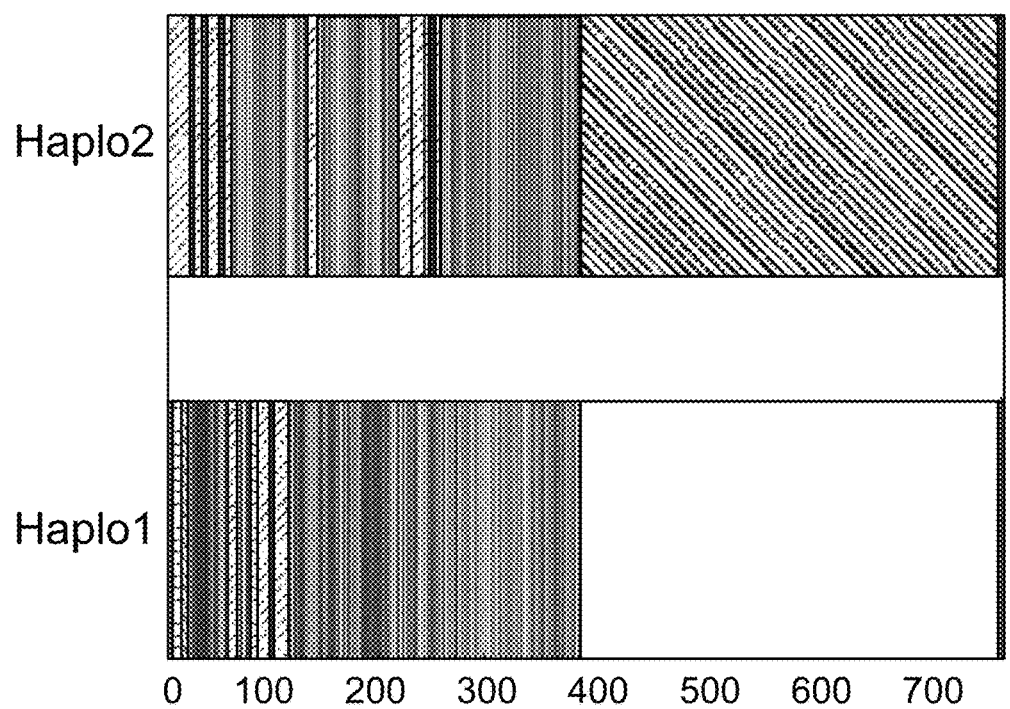
Figure 20C:
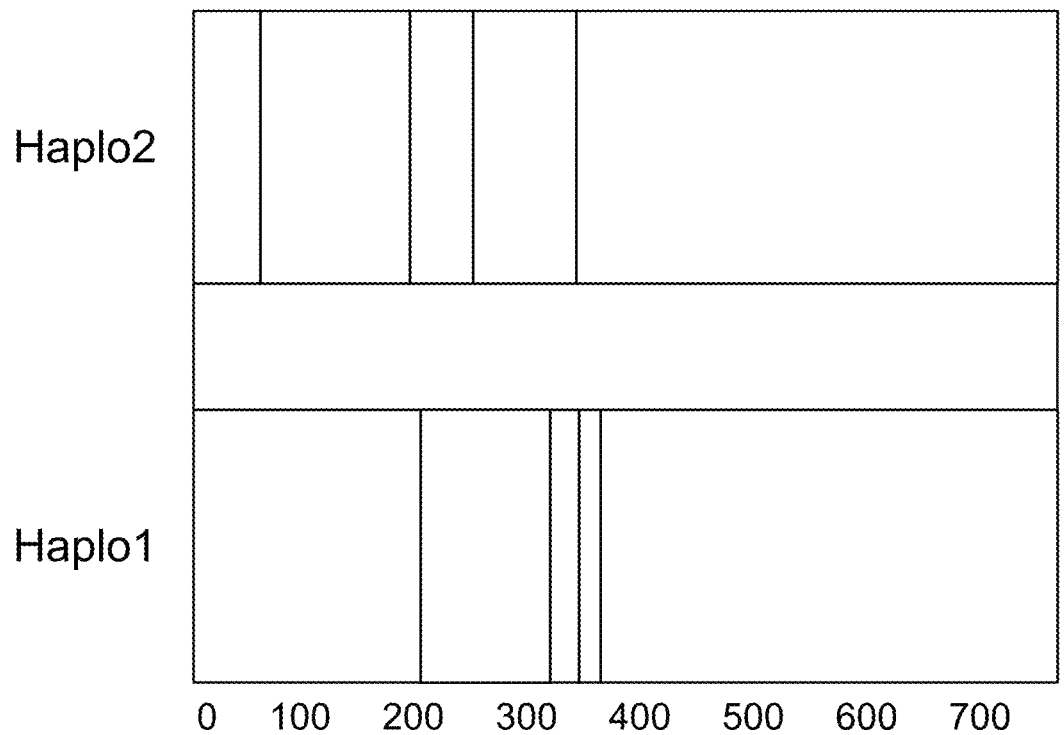
Figure 20D:
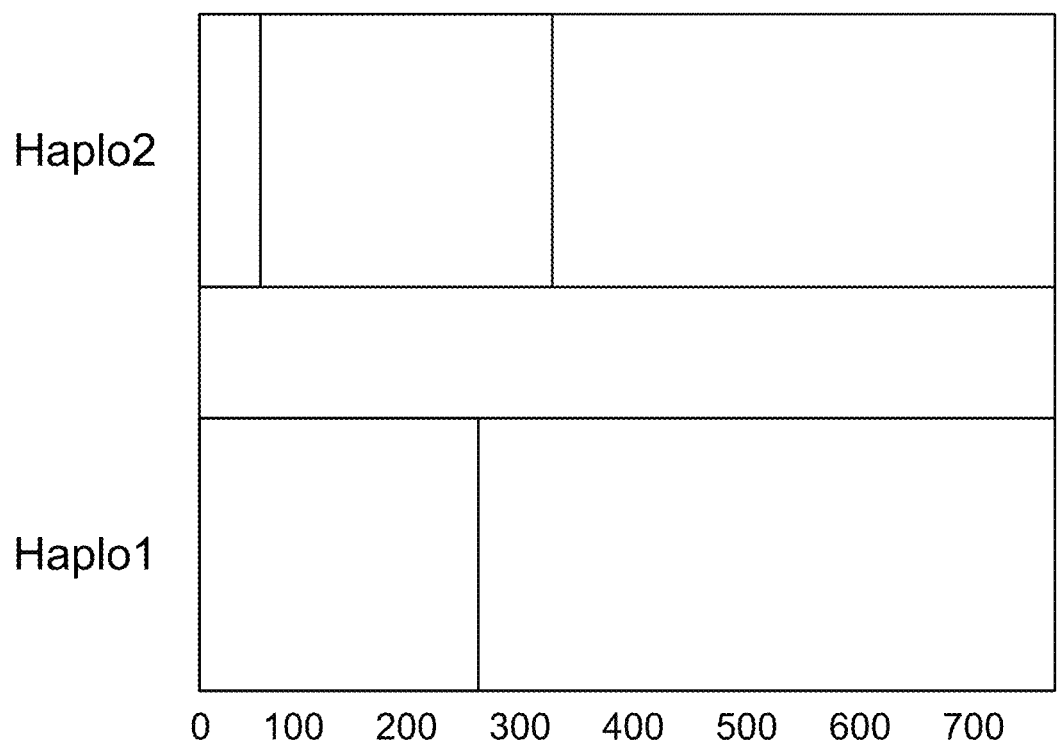

FIGS. 20A-20D are ancestry assignment plots illustrating different results that are obtained using different techniques. FIG. 20A is an example plot of ancestry assignments of two simulated haplotypes of a chromosome of a simulated individual. Each pattern in the haplotype represents a corresponding ancestry origin. This plot shows the true ancestries of the haplotypes. This data is input into different types of ancestry assignment modules and the outputs are compared. First, the data is input into a local classifier without error correction to generate an output that corresponds to FIG. 20B. As can be seen, the output is very noisy, where an underlying region that actually only corresponds to a single ancestry is given many ancestry assignments by the local classifier. The local classifier output is input into a basic HMM (e.g., the HMM of FIG. 16) that performs an averaging and corrects for the noise in the local classifier output, one haplotype at a time, to generate an output that corresponds to FIG. 20C. The HMM corrects some of the noise in the local classifier output but does not correct phasing errors or correlated classifier errors, and therefore the result does not perfectly resemble the true ancestry assignments of the two haplotypes. The local classifier output is also input into an HMM that corrects for noise, phasing errors and correlated classifier errors (e.g., the PHMM of FIG. 18 or the APHMM of FIG. 19) to generate an output that corresponds to FIG. 20D. The output perfectly matches the true ancestries of the underlying haplotypes (although the order of the haplotypes is reversed in the output).

FIG. 21 is a table comparing the predictive accuracies of ancestry assignments with and without error correction. The "before" columns show the recall and the precision associated with unadmixed or admixed individuals using a basic HMM. The "after" columns show the recall and the precision associated with unadmixed or admixed individuals using APHMM. As used herein, recall refers to what proportion of a particular ancestry is correctly predicted, and precision refers to what proportion of a particular ancestry prediction is correct. For example, if 20% of the underlying reference data corresponds to African ancestry, and the assignment technique predicts that a given haplotype segment corresponds to African ancestry 10% of the time, then recall refers to the portion of the 20% of the African ancestry that is correctly predicted, and precision refers to the portion of the 10% of the African ancestry predictions that in fact corresponds to true African ancestry. As can be seen, recall and prediction of both unadmixed individuals and admixed individuals are improved post-error correction.

As mentioned, in some implementations, smoothing is performed using a single module (e.g., a single HMM) that operates on and smooths the ancestry classification results from multiple classifiers. In such implementations, the smoother module may be configured to smooth ancestry classifications for multiple different chromosomes of the individual. In other implementations, smoothing is performed using separate modules for each of multiple different chromosomes of the individual. In other words, a first error correction module is dedicated to correcting ancestry classifications for a first chromosome, a second error correction module is dedicated to correcting ancestry classifications for a second chromosome, and so on.

Considering a general ancestry composition data flow, a pipeline process may begin with a data analysis system receiving or creating blocks of allele strings for contiguous polymorphism sites on a given chromosome. As mentioned, these blocks or windows may be phased. Computational processing throughout the data analysis pipeline may be performed on a window-by-window basis, with each window originating in an associated chromosome. In a data analysis pipeline, an ancestry classifier (e.g., a group of SVMs) receives a window and generates an initial predicted ancestry classification for the window. The resulting ancestry classification is sometimes referred to as a "hard call." The hard calls generated in this manner may be provided to one or more smoothing modules configured to address noisiness of the hard calls as well as potentially phasing errors and/or other errors in allele calls of the windows. The smoothing module(s) may be implemented as HMM(s), PHMMs, and/or APHMMs, such as described above.

In some embodiments, the data analysis pipeline performs recalibration using a recalibration module that receives smoothed ancestry classifications output by smoother modules. In some embodiments, a recalibration module is not included or is optionally turned off. In some embodiments that employ recalibration, recalibration is performed as described elsewhere herein.

As indicated, some pipelined ancestry composition systems employ a separate and unique smoothing module for each chromosome, and these chromosome-specific smoothing modules may be pretrained with data from many individuals (e.g., at least about 100 individuals or at least about 1000 individuals).

In some embodiments, a single smoother module is employed to process ancestry classifications (hard calls) from all chromosomes, not just from a single chromosome for which a smoother module is dedicated. In some embodiments that employ a single smoother for multiple chromosomes, at least some of the smoother's HMM parameters are generated and/or optimized using data from a single individual, who may be the individual under consideration (i.e., the individual for whom an ancestry composition analysis is being performed). The training data may include ancestry classifications (hard calls) from the individual under consideration.

When using a single smoother module—regardless of how it is trained—an ancestry composition system may output posterior ancestry classification predictions for each chromosome, such as on a window-by-window basis. So, while a single smoother module is employed, it receives ancestry classifications for particular windows of particular chromosomes and outputs smoothed ancestry classifications for the same windows of the same chromosomes. It performs this operation for multiple different chromosomes of the individual under consideration.

In embodiments employing a smoother module optimized with data from a single individual, such as the individual for whom ancestry composition analysis is being performed, the smoother module may be designed for use with that individual. In other words, unique smoother modules may be generated for each of multiple different individuals. In some cases, a unique smoother module generated for use with an individual under consideration may be optimized using ancestry classifications from some or all of that individual's chromosomes, rather than from just a single chromosome.

In certain embodiments, the process of training a smoother module using ancestry classifications (hard calls) from an individual under consideration starts with a pretrained HMM (e.g., one that was trained using data from one or more other individuals). Then, during training of the individual's HMM smoother, certain parameters of the pretrained HMM are modified by a process that employs ancestry classifications of the individual under consideration as training or optimization data. The pretrained HMM starting smoother may be generated using ancestry classifications from multiple individuals, and those individuals may not include the individual under consideration.

In some embodiments, the pretrained HMM smoother used as a starting point for individual-specific training is selected from a group of pretrained HMMs that comprises HMIs trained or optimized for a diverse group of types of individuals. For example, one starting HMM smoother may be trained using data from individuals of Latino descent, another starting HMM smoother may be trained using data from individuals of British Isles descent, yet another starting HMM smoother may be trained using data from individuals of Southeast Asian descent, and so on. Thus, while a group of available starting HMM smoothers may be produced in any of a number of different fashions, in some cases, the HMM smoothers are pretrained to perform well with a particular type of individual such as individuals of a particular ethnic ancestry. In some embodiments, the number of such pretrained starting HMMs to select from is at least 1, at least 2, or at least 5, or 5 to 30.

One of the available pretrained models may be selected based on one or more criteria indicating that the selected model will provide a useful starting point to further optimize the model for the individual under consideration. One approach to selecting such a model is to consider the distributions of hard calls among the training panels for the various pre-trained model HMMs and determine which most closely represents the distribution of hard calls for the individual under consideration. The distribution of hard calls may be determined on the basis of, for example, the hard calls over the various windows of each chromosome in the individual. In some embodiments, other criteria are employed. Thus, the choice of one of these HMM smoothers as a starting point for further training may be made by comparing classifier hard calls from the individual under consideration with the hard calls of each candidate pretrained HMM training panel for similarities in the distribution of hard calls over the genomes.

Choosing a starting HMM smoother in this manner may mean that the HMM parameters to be optimized likely have starting values that are relatively close (compared to the parameter values of the other pretrained smoother HMMs) to the final optimized values. This may allow training to proceed more efficiently.

Various methods may be employed to select a starting HMM smoother. In some embodiments, the method is a Naive Bayes bag-of-words model. In some embodiments, the method is a multinomial regression. Thus, as examples, a Naive Bayes bag-of-words model and/or a multinomial regression model may serve the purpose of predicting or choosing a best pretrained model to use as a starting point to further optimize the model for the individual under consideration. The difference is only in the mathematical formulation (i.e., how that best pretrained model is selected by the model. The Naive Bayes bag-of-words model (aka multinomial Naive Bayes, but not to be confused with multinomial regression) is parameterized by N (the number of pretrained HMM models, e.g., 11) categorical distributions of K (the number of ancestries, e.g., 45) features. For a particular K-vector of hard call counts from an individual under consideration for ancestry composition, the Naive Bayes bag-of-words model chooses the pretrained model (one of N) with the categorical distribution with the highest likelihood of that K-vector. On the other hand, multinomial regression is trained to transform, in this case, K-vectors of hard call counts into categorical distributions of size N. The chosen pretrained model (again, one of N) would be the pretrained model with the greatest probability in the output from the multinomial regression model.

Regardless of how a starting HMM smoother is chosen or produced, one or more of its parameters may be optimized by considering ancestry classification hard calls from the user under consideration. In certain embodiments, transition parameters of the starting HMM smoother are optimized using the individual's ancestry classification hard calls. In some such embodiments, the emission parameters of the starting HMM are not optimized, rather they remain unmodified in the fully trained and optimized smoother. In some embodiments, transition parameters of the starting HMM smoother are optimized using hard calls from across multiple chromosomes of that individual, e.g., from at least two chromosomes, or from at least five chromosomes, or from all chromosomes. In some cases, the ancestry composition system is configured such that for each individual to be analyzed, the system optimizes smoother transition parameters based on that individual's genome-wide SVM hard calls and eventually calculates posterior probabilities with the optimized (i.e., individualized) smoother.

An HMM smoother optimized using ancestry classification data from the individual under consideration may be applied to correct hard calls from classifiers for that individual's chromosomes as described elsewhere herein. For example, a probabilistic scoring scheme and/or dynamic programming may be employed.

Figure 22A:
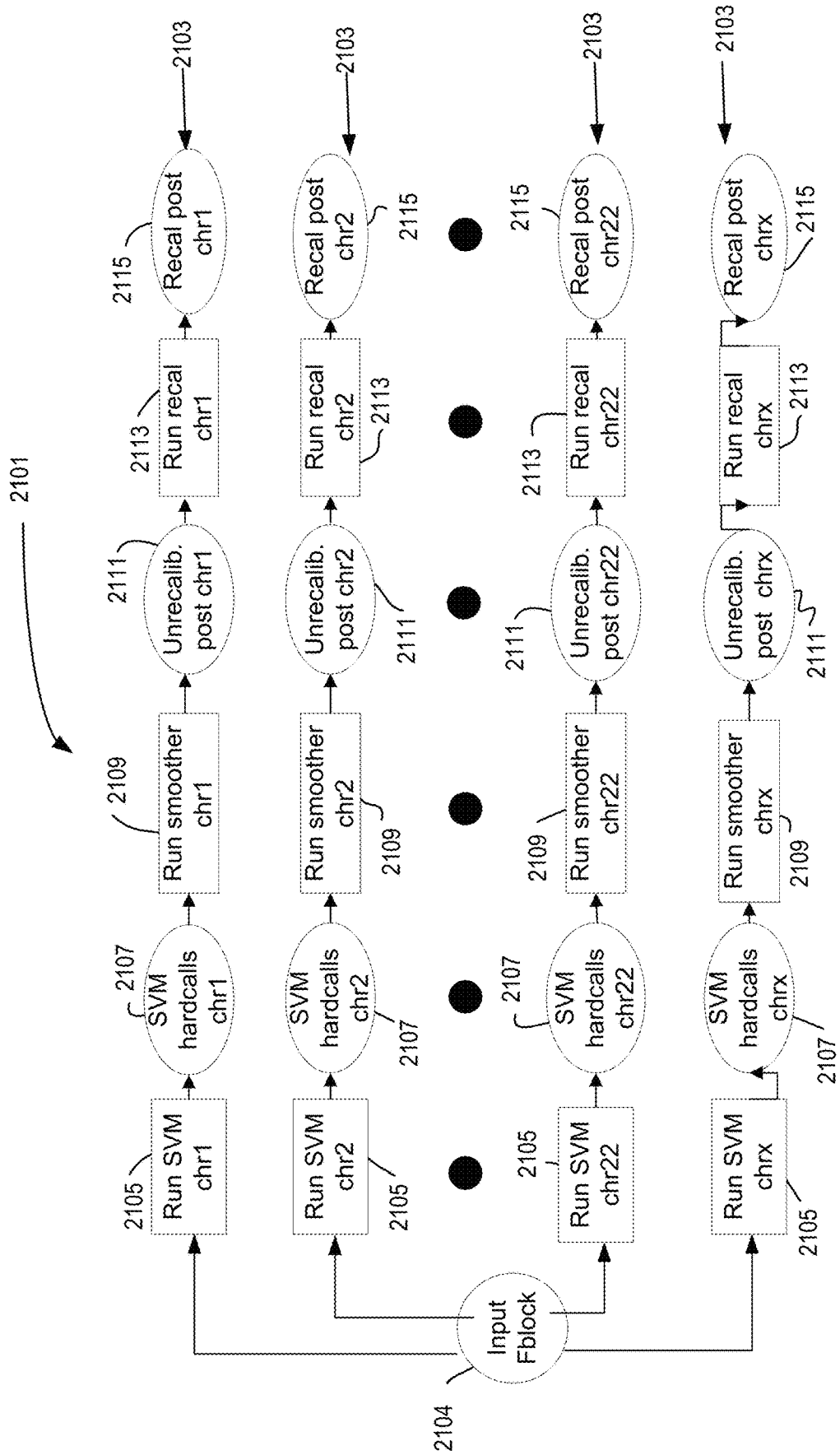
FIGS. 22A and 22B are flow diagrams illustrating ancestry composition pipelines that employ separate smoother modules for each chromosome (FIG. 22A) and a single smoother module for all chromosomes (FIG. 22B).
Figure 22B:
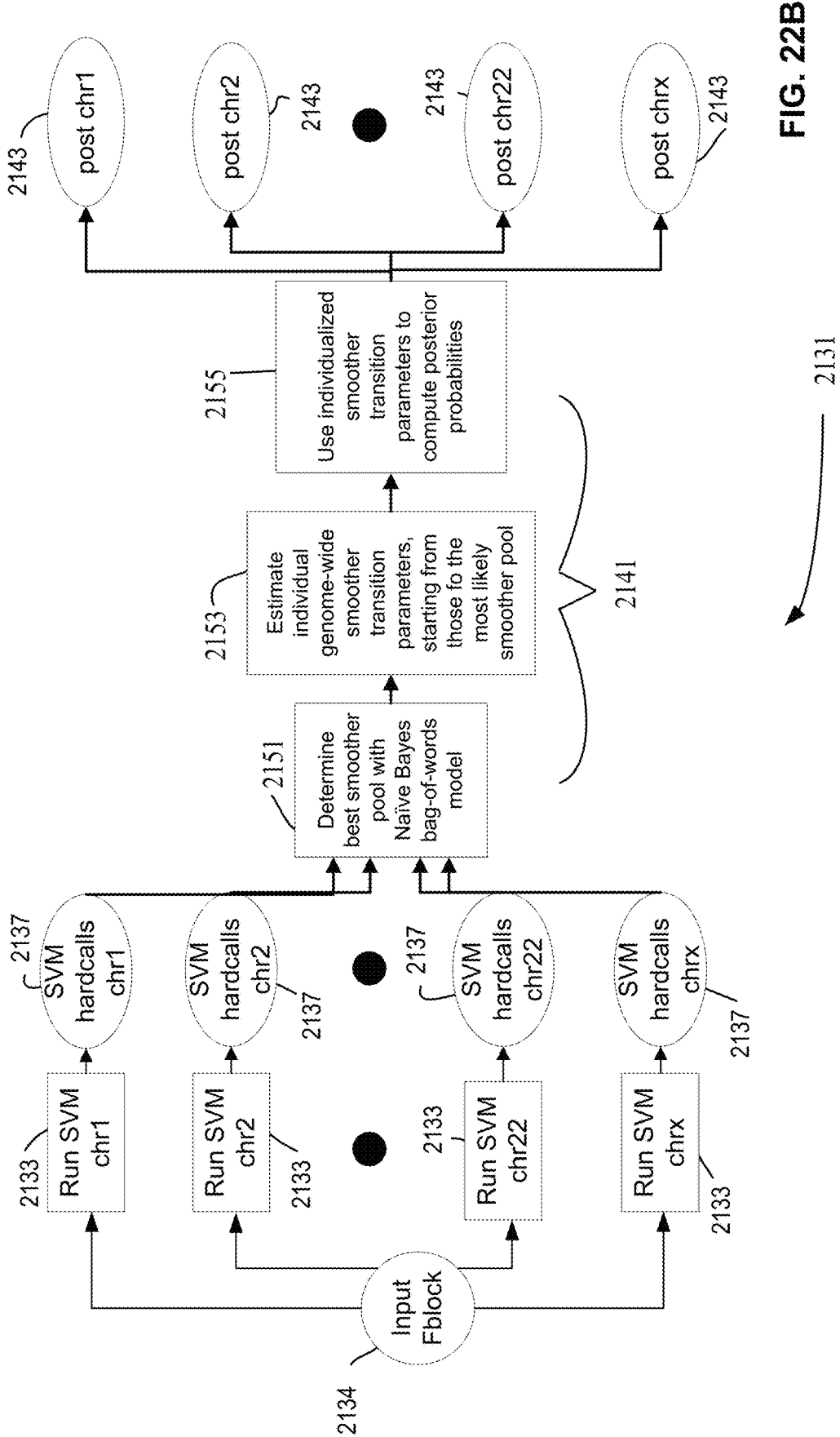

FIGS. 22A and 22B schematically depict example data analysis flows for two approaches to ancestry composition determination for an individual under consideration. In the first example, which is depicted in FIG. 22A, an ancestry composition data pipeline 2101 is configured to separately consider the ancestry composition of each chromosome through the entire pipeline. In other words, the data analysis has multiple fully parallel subpipelines, with a separate subpipeline 2103 for each chromosome under consideration. Each subpipeline may be configured to receive phased sequence segments or blocks ("fblocks") 2104 for its respective chromosome. Each subpipeline is configured to process the phased data for an associated chromosome by an ancestry classifier 2105 and a smoother module 2109 in pipelined fashion. In the example of data pipeline 2101, each ancestry classifier includes a group of SVMs that are configured to output ancestry hard calls (predicted ancestries of DNA sequence segments) 2107 for its associated chromosome. Also, in the example of pipeline 2101, each smoother is depicted as a module 2109 that is configured to receive the predicted ancestries 2107 and output posterior predicted ancestries 2111. Additionally, each subpipeline 2103 has an optional recalibration module 2113 located downstream from the smother modules 2109. The recalibration modules 2113 are configured to output recalibrated posterior predicted ancestries 2115, which may serve as ancestry composition calls for the sequence segments of each chromosome under consideration. The individual ancestry classifiers, smoother modules, and recalibration modules may be implemented as described elsewhere herein. Note that SVMs are just one example of ancestry classifiers. As mentioned, other classifiers such as random forests and recurrent neural networks may be employed.

By comparison, a data processing pipeline 2131 for ancestry composition as depicted in FIG. 22B is configured to perform smoothing of predicted ancestries using a single smoother system 2141 for all chromosomes under consideration. However, pipeline 2131 also includes separate ancestry classifiers 2133, each dedicated to a different one of the chromosomes under consideration. Each classifier 2133 may include a group of SVMs configured to output ancestry hard calls (predicted ancestries of DNA sequence segments) 2137 for its associated chromosome. In certain embodiments, the classifiers 2133 are implemented as described above herein.

Pipeline 2131 is configured to receive phased sequence segments or blocks 2134 for an individual under consideration and route such segments, based on the chromosomes from which they originate, to the respective classifiers 2133. Data processing pipeline 2131 is further configured to provide the predicted ancestries 2137 for each chromosome to the smoother system 2141, which is configured to output posterior predicted ancestries 2143 on a chromosome-by-chromosome basis. Stated another way, in operation, (a) a first classifier 2133 outputs predicted ancestries for sequence segments of a first chromosome, and smoother system 2141 outputs posterior predicted ancestry calls 2143 for the first chromosome; (b) a second classifier 2133 outputs predicted ancestries for sequence segments of a second chromosome, and smoother system 2141 outputs posterior predicted ancestry calls 2143 for the second chromosome, and so on, with sequence segment data for each chromosome under consideration being processed by its own dedicated classifier 2133 and a common smoother 2141. Optionally, pipeline 2131 is configured to provide ancestry composition determinations without performing recalibration. In certain embodiments, pipeline 2131 is implemented with one or more recalibration modules, which are optionally designed as described elsewhere herein. In the depicted embodiment, pipeline 2131 does not employ recalibration modules.

As depicted, smoother system 2141 may be logically divided into three modules. A first module 2151 is configured to select a pretrained HMM smoother from among a group of pretrained HMM's as a starting point for optimization of parameters to yield a final HMM that will be used to correct the calls for an individual under consideration. In some implementations, module 2151 is configured to select based on similarities in distributions of hard calls in the individual under consideration and the selected pretrained HMM. A second module 2153 is configured to train a smoother using ancestry classifications for the individual under consideration. In some implementations, second module 2153 is configured to use ancestry classifications from some or all of the chromosomes of the individual under consideration. Module 2153 may be configured to optimize certain parameters of the pretrained HMM smoother selected by module 2151. In some embodiments, module 2153 optimizes transition parameters of the selected pretrained HMM smoother. A third module 2155 is configured to use a HMM smoother trained by module 2153 to evaluate and, in some cases, correct ancestry classification hard calls 2137. Module 2155 may operate in a manner described elsewhere herein. For example, module 2155 may use a probabilistic scoring scheme and/or dynamic programming. Module 2155 is configured to output posterior predicted ancestries 2143 on a window-by-window basis, with each ancestry 2143 applied to the chromosome from which the alleles of the window were obtained.

A difference between the embodiments of FIGS. 22A and 22B is that the embodiment of FIG. 22B involves training parameters genome-wide. For example, in the expectation count of an EM algorithm used to train HMIs, the embodiment sums expected counts across a single individual's chromosomes. In the embodiment of FIG. 22A, the training algorithm sums expected counts across many individuals at the same chromosome.

HMM Parameters

HMIs generally require three sets of parameters: initial state distributions, hidden-state transition probabilities, and emission distributions. In certain embodiments, the individual-level training described herein only applies to the hidden-state transition parameters. In such embodiments, emission parameters may be pre-trained on large samples of other individuals, such as large samples of unadmixed individuals. In other words, the model selected as a starting point has a set of emission parameters and transition parameters, and only the transition parameters are adjusted during training. In such embodiments, the emission parameters remain fixed.

Certain embodiments employ initial state distributions (prior belief about the hidden states without observations) that make the hidden-state process stationary across the genome, such that implicitly the same prior beliefs about ancestry apply at each location across the chromosome. This assumes that the relative percentage of ancestry composition from various groups remains fixed when generating the initial state distribution.

A mathematical explanation of examples of techniques for generating emission and transition parameters is below. In this example, y represents the hidden states, x represents the observed states, s represents the hidden switch indicators, K represents the number of available actual ancestry classifications (available hidden states), N represents the number of available observed ancestry classifications (available observed states), and S is the number of windows, each window including a number M of polymorphism site positions in a sequence.

As indicated, HMM transition parameters represent the transitioning between hidden states within a chromosome or across the genome and the hidden states are pairs of unobserved ancestries on the two homologous chromosomes. In certain embodiments, three sets of parameter values, each representing probabilities, are optimized when training a HMM for smoothing ancestry classifications.

A first of these parameters is a probability of transitioning into a particular ancestry at a given recombination site in a sequence. In an HMM, this probability may be represented by a vector mu ($\mu$). Each element in the vector is a probability value (a value between 0 and 1). In some examples, is a 45-element vector, with each element representing the probability of transitioning into one of 45 different ancestries. Note that a "transition" in this framework may transition into the same ancestry as the current ancestry. Note also that $\mu$ is not dependent on the current ancestry state.

A second of these parameters is theta ($\theta$), which represents the probability of a recombination event having occurred. In certain embodiments, $\theta$ is a scalar. In certain embodiments, $\theta$ varies as a function of position on a chromosome or the current ancestry state (e.g., there are 45 values of $\theta$).

Considering $\mu$ and $\theta$, the probability of transitioning from one hidden state to another may be viewed as determining whether there is a recombination, and, if so, what hidden state (ancestry) results from that transition.

A third of these parameters is sigma ($\sigma$), which represents a likelihood of a phase switch error. In certain embodiments, $\sigma$ is a single probability across all ancestries. In some cases, $\sigma$ is a function of chromosome position, and this function may be unique for particular individuals.

The process of optimizing these parameters ($\mu$, $\theta$, and $\sigma$) may employ an expectation-maximization or EM algorithm. In certain embodiments, the EM algorithm may use the forward and backward algorithms to calculate expected counts of different parameterized events, like the number of recombination events (for $\theta$), phased switches (for $\sigma$), or transitions into different ancestries at recombination events (for $\mu$). Some optimization techniques leverage symmetry in hidden-state transitions to reduce the complexity of the forward and backward algorithms from $O(SK^4)$ complexity to $O(SK^2)$ complexity, where S is the number of windows on a chromosome and K is the number of ancestries.

A directed probabilistic model may consist of:

S hidden states, $y_{1:S}=(y_1, y_2, \ldots, y_S)$, where $y_t=(y_t^0, y_t^1) \in \{1, \ldots, K\}^2$ represents the true population labels of haplotypes 0 and 1 within window t;

S observed states $x_{1:S}=(x_1, x_2, \ldots, x_S)$, where $x_t=(x_t^0, x_t^1) \in \{1, \ldots, N\}^2$ represents the observed population labels for the t-th pair of haplotype windows (i.e., the output from the local classifier); and S−1 hidden switch indicators, $s_{2:S}=(s_1, s_2, \ldots, s_S)$, where $s_t \in \{0,1\}$ denotes whether a phasing switch error has occurred between windows t−1 and t.

Figure 22C:
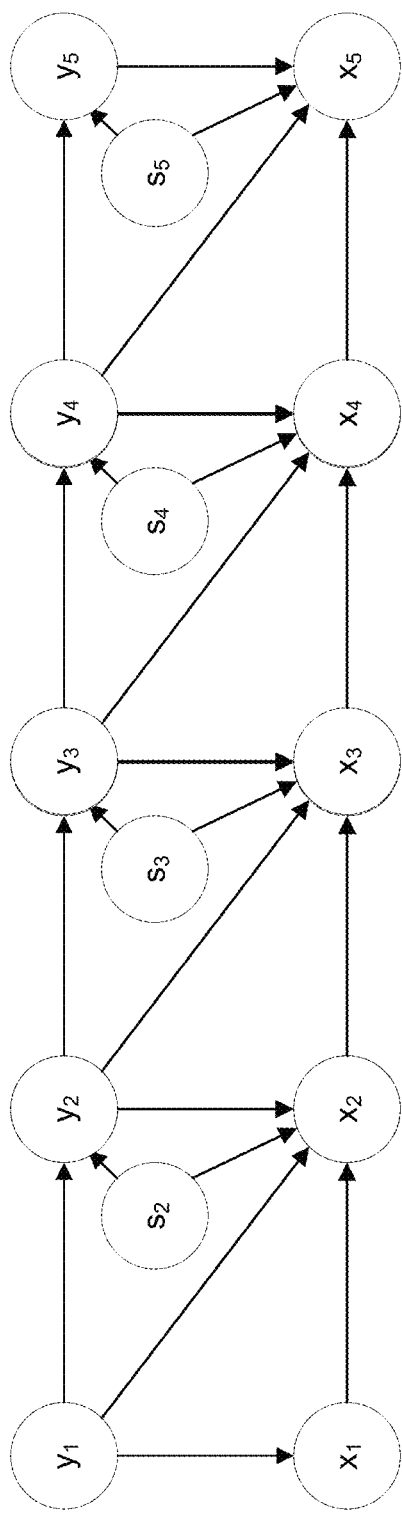
FIG. 22C presents a graphical model of a smoothing process using a hidden Markov Model.

FIG. 22C shows a graphical model of a smoothing model for a sequence of length S=5. In some embodiments the model may assume that phasing switch errors occur only at the boundaries between windows.

The joint probability of $y_{1:S}$, $x_{1:S}$, and $S_{2:S}$ may be modeled as:

$$P(y_{1:S}, x_{1:S}, s_{2:S}) = \\ P(y_1)P(x_1 \mid y_1) \prod_{t=2}^{S} P(s_t)P(y_t \mid y_{t-1}, s_t)P(x_t \mid x_{t-1}, y_{t-1}, y_t, s_t)$$

This model may be parameterized with $2(K^2+K)+1$ parameters:

$\{\mu_y\}_{1:K}$, the prior distribution of hidden states following a recombination event;

$\{\mu_{x|y}\}_{1:K^2}$, the prior distribution of emissions, conditional on hidden states;

$\sigma$, the prior probability that a phasing switch error occurs between two consecutive windows;

$\{\theta_y\}_{1:K}$, the prior probabilities of recombination between two consecutive windows, when the first has hidden state y; and $\{\varepsilon_{y,x}\}_{1:K^2}$, the prior probabilities of observed-state label resets between two consecutive windows, when the first has observed state x and both have hidden state y.

Each component of the joint probability expression may be expressed in terms of these parameters:

Initial hidden-state distribution. The population assignments for each of the two haplotypes is sampled independently from the stationary distribution of hidden states, $\pi$:

$$P(y_1) = \prod_{h \in \{0,1\}} \pi_{y_1^h}$$

where $$\pi_i = \frac{\mu_i/\theta_i}{\sum_{j=1}^{K} \mu_j/\theta_j}$$

In one version of an HMM described herein, the prior probability of recombination was a scalar, $\theta$, constant across hidden states. When this was the case, the stationary distribution of hidden states, $\pi$, was equal to the prior distribution of hidden states, $\mu$.

Initial emission distribution. The initial emissions for each haplotype are sampled independently from the prior distribution for emissions:

$$P(x_1 \mid y_1) = \prod_{h \in 0,1} \rho_{x_1^h \mid y_1^h}$$

Switch error model. We assume that switch errors occur with constant probability a between each pair of states:

$$P(s_t) = \sigma^{(s_t)}(1-\sigma)^{(1-s_t)}$$

Transition probability model. For each haplotype, a recombination occurs from hidden state y with probability $\theta_y$, and for each recombination, a new hidden population label is drawn from the prior distribution for hidden states. Thus, $$P(y_t \mid y_{t-1}, s_t) = \prod_{h \in \{0,1\}} P(y_t^h \mid y_{t-1}^{h \oplus s_t})$$
$$= \prod_{h \in \{0,1\}} f(y_{t-1}^{h \oplus s_t}, y_t^h)$$

where $$f(y', y) = \theta_{y'}\mu_y + (1 - \theta_{y'})1\{y' = y\}.$$

Emission probability model. In order to accommodate correlated errors in local ancestry classifications, the APHMM's emission model is autoregressive: given no change in hidden state, the observed states are correlated. This autoregressivity increases posterior decoding accuracy without any apparent performance decline.

As with the transition probability model, each haplotype is treated independently in the emission probability model. Consider two consecutive hidden states, $y_{t-1}$ and $y_t$. If they are unequal (i.e., a true ancestry switch has occurred), then an observed-state label reset necessarily occurs, and the emission at window t, $x_t$, is drawn from the prior distribution for emissions, $\{\mu_{x|y_t}\}$. If a true ancestry switch has not occurred (i.e., $y_{t-1}=y_t=y$), an observed-state label reset occurs with probability $\varepsilon_{y,xt-1}$:

$$P(x_t \mid x_{t-1}, y_{t-1}, y_t, s_t) = \prod_{h \in \{0,1\}} g(x_{t-1}^{h \oplus s_t}, x_t^h, y_{t-1}^{h \oplus s_t}, y_t^h)$$

where $$g(x', x, y', y) = \begin{cases} \mu_{x|y} & \text{if } y' \neq y \\ \varepsilon_{y,x'}\mu_{x|y} + (1 - \varepsilon_{y,x'})1\{x = x'\} & \text{if } y' = y \end{cases}$$

These model parameters may be estimated using the expectation-maximization (EM) algorithm. Posterior probabilities for each window may be estimated using the forward and backward algorithms for hidden Markov models. Using dynamic programming techniques, the complexity of the posterior decoding step is $O(SK^2)$, where S is the number of windows to decode and K is the number of populations.

Forward Algorithm

The goal of the forward algorithm is to compute:

$$Z_\alpha = \sum_{y_{1:L},s_{2:L}} P(y_1)P(x_1 \mid y_1)\prod_{l=2}^{S} P(s_l)P(y_l \mid y_{l-1}, s_l)P(x_l \mid x_{l-1}, y_l, y_{l-1}, s_l).$$

The forward dynamic programming matrix may be defined as:

$$\alpha_t(y_t) =$$

$$\sum_{y_{1:t-1},s_{2:t}} P(y_1)(x_1 \mid y_1)\left(\prod_{l=2}^{t} P(s_l)P(y_l \mid y_{l-1}, s_l)P(x_l \mid x_{l-1}, y_l, y_{l-1}, s_l)\right)$$

such that $$Z\alpha = \sum_{y_L} \alpha_L(y_L).$$

This matrix can be computed recursively as:

$$\alpha_t(y_t) = \sum_{y_{t-1},s_t} P(s_t)P(y_t \mid y_{t-1}, s_t)P(x_t \mid x_{t-1}, y_t, y_{t-1}, s_t)\alpha_{t-1}(y_{t-1})$$

where the base case is $$\alpha_1(y_1) = P(y_1)P(x_1|y_1).$$

Coded as shown above, the recurrences would take $O(LK^4)$ time to evaluate since $\alpha_t(y_t)$ is computed for S possible choices of t and $K^2$ possible choices of $y_t$ (with each evaluation involving a summation over $K^2$ possible choices of $y_{t-1}$). However, the running time may be reduced to $O(SK^2)$ by taking advantage of the structure of the transition probability distribution. In particular, consider the recurrence:

$$\alpha_t(y_t) = \sum_{y_{t-1}, s_t} P(s_t) P(y_t \mid y_{t-1}, s_t) P(x_t \mid x_{t-1}, y_t, y_{t-1}, s_t) \alpha_{t-1}(y_{t-1})$$

$$\alpha_t(y_t) = \sum_{s_t} P(s_t) \sum_{y_{t-1}} P(y_t \mid y_{t-1}, s_t) P(x_t \mid x_{t-1}, y_t, y_{t-1}, s_t) \alpha_{t-1}(y_{t-1})$$

Here, the inner summation can be written as:

$$\sum_{y_{t-1}} P(y_t \mid y_{t-1}, s_t) P(x_t \mid x_{t-1}, y_t, y_{t-1}, s_t) \alpha_{t-1}(y_{t-1}) =$$

$$\sum_{y_{t-1}} \left( \prod_{h \in \{0,1\}} f\left(y_t^h, y_t^h = y_{t-1}^{h \otimes s_t}\right) \right) \left( \prod_{h \in \{0,1\}} g\left(x_t^h, x_{t-1}^{h \otimes s_t}, y_t^h, y_t^h = y_{t-1}^{h \otimes s_t}\right) \right) \alpha_{t-1}(y_{t-1}) =$$

$$\sum_{z^0 \in \{0,1\}} \sum_{z^1 \in \{0,1\}} \sum_{\substack{y_{t-1}: \\ 1\{y_t^0 = y_{t-1}^{h \otimes s_t}\} = z^0 \\ 1\{y_t^1 = y_{t-1}^{h \otimes s_t}\} = z^1}} \left( \prod_{h \in \{0,1\}} f\left(y_t^h, z^h\right) \right)$$

$$\left( \prod_{h \in \{0,1\}} g\left(x_t^h, x_{t-1}^{h \otimes s_t}, y_t^h, z^h\right) \right) \alpha_{t-1}(y_{t-1}) =$$

$$\sum_{z^0 \in \{0,1\}} \sum_{z^1 \in \{0,1\}} \left( \prod_{h \in \{0,1\}} f\left(y_t^h, z^h\right) \right) \left( \prod_{h \in \{0,1\}} g\left(x_t^h, x_{t-1}^{h \otimes s_t}, y_t^h, z^h\right) \right) \alpha_t^*(y_t, s_t, z)$$

where $$\alpha_t^*(y_t, s_t, z) = \sum_{\substack{y_{t-1}: \\ 1\{y_t^0 = y_{t-1}^{h \otimes s_t}\} = z^0 \\ 1\{y_t^1 = y_{t-1}^{h \otimes s_t}\} = z^1}} \alpha_{t-1}(y_{t-1})$$

To compute $\alpha^*$ efficiently, precompute the following:

$$A_t^{1,0}(i) = \sum_j \alpha_{t-1}(i, j)$$

$$A_t^{0,1}(j) = \sum_i \alpha_{t-1}(i, j)$$

$$A_t^{0,0} = \sum_{i,j} \alpha_{t-1}(i, j)$$

It follows that $$\alpha_t^*(y_t, s_t, z) = \begin{cases} \alpha_{t-1}\left(\left(y_t^0, y_t^1\right)\right) & \text{if } s_t = 0 \text{ and } z^0 = 1 \text{ and } z^1 = 1 \\ A_t^{1,0}\left(y_t^0\right) - \alpha_{t-1}\left(\left(y_t^0, y_t^1\right)\right) & \text{if } s_t = 0 \text{ and } z^0 = 1 \text{ and } z^1 = 0 \\ A_t^{0,1}\left(y_t^1\right) - \alpha_{t-1}\left(\left(y_t^0, y_t^1\right)\right) & \text{if } s_t = 0 \text{ and } z^0 = 0 \text{ and } z^1 = 1 \\ A_t^{0,0} - A_t^{1,0}\left(y_t^0\right) - A_t^{0,1}\left(y_t^1\right) + \alpha_{t-1}\left(\left(y_t^0, y_t^1\right)\right) & \text{if } s_t = 0 \text{ and } z^0 = 0 \text{ and } z^1 = 0 \\ \alpha_{t-1}\left(\left(y_t^0, y_t^1\right)\right) & \text{if } s_t = 1 \text{ and } z^0 = 1 \text{ and } z^1 = 1 \\ A_t^{0,1}\left(y_t^0\right) - \alpha_{t-1}\left(\left(y_t^0, y_t^1\right)\right) & \text{if } s_t = 1 \text{ and } z^0 = 1 \text{ and } z^1 = 0 \\ A_t^{1,0}\left(y_t^1\right) - \alpha_{t-1}\left(\left(y_t^0, y_t^1\right)\right) & \text{if } s_t = 1 \text{ and } z^0 = 0 \text{ and } z^1 = 1 \\ A_t^{0,0} - A_t^{0,1}\left(y_t^0\right) - A_t^{1,0}\left(y_t^1\right) + \alpha_{t-1}\left(\left(y_t^1, y_t^0\right)\right) & \text{if } s_t = 1 \text{ and } z^0 = 0 \text{ and } z^1 = 0 \end{cases}$$

For each level t, precomputation of the $A^{*,*t}$ matrices takes $O(K^2)$ time. Once the precomputation is complete, then each value of $\alpha_t(y_t)$ can be computed in $O(1)$ time.

Backward Algorithm

The goal of the backward algorithm is to compute:

$$Z_\beta = \sum_{y_{1:L}, s_{2:L}} P(y_1) P(x_1 \mid y_1) \prod_{l=2}^{L} P(s_l) P(y_l \mid y_{l-1}, s_l) P(x_l \mid x_{l-1}, y_l, y_{l-1}, s_l).$$

The backward dynamic programming matrix may be defined as:

$$\beta_t(y_t) = \sum_{y_{t+1:L}, s_{t+1:L}} \left( \prod_{l=t+1}^{L} P(s_l) P(y_l \mid y_{l-1}, s_l) P(x_l \mid x_{l-1}, y_l, y_{l-1}, s_l) \right)$$

such that $$Z_\beta = \sum_{y_1} P(y_1) P(x_1 \mid y_1) \beta_1(y_1).$$

This matrix can be computed recursively as:

$$\beta_t(y_t) = \sum_{y_{t+1}, s_{t+1}} P(s_{t+1}) P(y_{t+1} \mid y_t, s_{t+1}) P(x_{t+1} \mid x_t, y_{t+1}, y_t, s_{t+1}) \beta_{t+1}(y_{t+1})$$

where the base case is $\beta_t(y_t) = 1$

The running time may be improved by taking advantage of the transition probability distribution. Consider the recurrence:

$$\beta_t(y_t) = \sum_{y_{t+1}, s_{t+1}} P(s_{t+1}) P(y_{t+1} \mid y_t, s_{t+1}) P(x_{t+1} \mid x_t, y_{t+1}, y_t, s_{t+1}) \beta_{t+1}(y_{t+1})$$

$$\beta_t(y_t) = \sum_{s_{t+1}} P(s_{t+1}) \sum_{y_{t+1}, s_{t+1}} P(y_{t+1} \mid y_t, s_{t+1}) P(x_{t+1} \mid x_t, y_{t+1}, y_t, s_{t+1}) \beta_{t+1}(y_{t+1})$$

Here, the inner summation can be written as:

$$\sum_{y_{t+1}} P(y_{t+1}|y_t, s_{t+1}) P(x_{t+1}|x_t, y_{t+1}, y_t, s_{t+1}) \beta_{t+1}(y_{t+1})$$

$$= \sum_{y_{t+1}} \left( \prod_{h \in \{0,1\}} f\left(y_{t+1}^h, y_{t+1}^h = y_t^{h \oplus s_{t+1}}\right) \right)$$

$$\left( \prod_{h \in \{0,1\}} g\left(x_{t+1}^h, x_t^{h \oplus s_{t+1}}, y_{t+1}^h, y_{t+1}^h = y_t^{h \oplus s_{t+1}}\right) \right) \beta_{t+1}(y_{t+1})$$

$$= \sum_{z^0 \in \{0,1\}} \sum_{z^1 \in \{0,1\}} \sum_{\substack{y_{t-1}: \\ 1\{y_{t+1}^0 = y_t^{h \oplus s_{t+1}}\}=z^0 \\ 1\{y_{t+1}^1 = y_t^{h \oplus s_{t+1}}\}=z^1}} \left( \prod_{h \in \{0,1\}} f(y_{t+1}^h, z^h) \right)$$

$$\left( \prod_{h \in \{0,1\}} g\left(x_{t+1}^h, x_t^{h \oplus s_{t+1}}, y_{t+1}^h, z^h\right) \right) \beta_{t+1}(y_{t+1})$$

$$= \sum_{z^0 \in \{0,1\}} \sum_{z^1 \in \{0,1\}} \beta_t^*(y_t, s_{t+1}, z)$$

where $$\beta_t^*(y_t, s_{t+1}, z) = \sum_{\substack{y_{t+1}: \\ 1\{y_{t+1}^0 = y_t^{h \oplus s_{t+1}}\}=z^0 \\ 1\{y_{t+1}^1 = y_t^{h \oplus s_{t+1}}\}=z^1}} \tilde{\beta}_{t+1}(y_{t+1}, s_{t+1}, z)$$

$$\tilde{\beta}_{t+1}(y_{t+1}, s_{t+1}, z) = \left( \prod_{h \in \{0,1\}} f(y_{t+1}^h, z^h) \right) \left( \prod_{h \in \{0,1\}} g\left(x_{t+1}^h, x_t^{h \oplus s_{t+1}}, y_{t+1}^h, z^h\right) \right) \beta_{t+1}(y_{t+1})$$

To compute $\beta^*$ efficiently, we precompute the following:

$$B_t^{s,1,1}(i, j) = \tilde{\beta}_{t+1}((i, j), s, (1, 1))$$

$$B_t^{s,1,0}(i) = \sum_j \tilde{\beta}_{t+1}((i, j), s, (1, 0))$$

$$B_{t,a}^{s,1,0}(i, j) = \tilde{\beta}_{t+1}((i, j), s, (1, 0))$$

$$B_t^{s,0,1}(j) = \sum_i \tilde{\beta}_{t+1}((i, j), s, (0, 1))$$

$$B_{t,a}^{s,0,1}(i, j) = \tilde{\beta}_{t+1}((i, j), s, (0, 1))$$

$$B_t^{s,0,0} = \sum_{i,j} \tilde{\beta}_{t+1}((i, j), s, (0, 0))$$

$$B_{t,a}^{s,0,0}(i) = \sum_j \tilde{\beta}_{t+1}((i, j), s, (0, 0))$$

$$B_{t,b}^{s,0,0}(j) = \sum_i \tilde{\beta}_{t+1}((i, j), s, (0, 0))$$

$$B_{t,c}^{s,0,0}(i, j) = \tilde{\beta}_{t+1}((i, j), s, (0, 0))$$

It follows that $$\beta^*(y_t, s_{t+1}, z) = \begin{cases} B_t^{0,1,1}\left((y_t^0, y_t^1)\right) & \text{if } s_{t+1} = 0 \text{ and } z^0 = 1 \text{ and } z^1 = 1 \\ B_t^{0,1,0}(y_t^0) - B_{t,a}^{0,1,0}\left((y_t^0, y_t^1)\right) & \text{if } s_{t+1} = 0 \text{ and } z^0 = 1 \text{ and } z^1 = 0 \\ B_t^{0,0,1}(y_t^1) - B_{t,a}^{0,0,1}\left((y_t^0, y_t^1)\right) & \text{if } s_{t+1} = 0 \text{ and } z^0 = 0 \text{ and } z^1 = 1 \\ B_t^{0,0,0} - B_{t,a}^{0,0,0}(y_t^0) - B_{t,b}^{0,0,0}(y_t^1) + B_{t,c}^{0,0,0}\left((y_t^0, y_t^1)\right) & \text{if } s_{t+1} = 0 \text{ and } z^0 = 0 \text{ and } z^1 = 0 \\ B_t^{1,1,1}\left((y_t^0, y_t^1)\right) & \text{if } s_{t+1} = 1 \text{ and } z^0 = 1 \text{ and } z^1 = 1 \\ B_t^{1,0,1}(y_t^0) - B_{t,a}^{1,0,1}\left((y_t^1, y_t^0)\right) & \text{if } s_{t+1} = 1 \text{ and } z^0 = 1 \text{ and } z^1 = 0 \\ B_t^{1,1,0}(y_t^1) - B_{t,a}^{1,1,0}\left((y_t^1, y_t^0)\right) & \text{if } s_{t+1} = 1 \text{ and } z^0 = 0 \text{ and } z^1 = 1 \\ B_t^{1,0,0} - B_{t,a}^{1,0,0}(y_t^1) - B_{t,b}^{1,0,0}(y_t^0) + B_{t,c}^{1,0,0}\left((y_t^1, y_t^0)\right) & \text{if } s_{t+1} = 1 \text{ and } z^0 = 0 \text{ and } z^1 = 0 \end{cases}$$

For each level t, precomputation of the $\beta_t^{\cdot,\cdot,\cdot}$ matrices takes $O(K^2)$ time. Once the precomputation is complete, then each value of $\beta_t(y_t)$ can be computed in $O(1)$ time.

Parameter Estimation

When training with only unadmixed individuals, it may be difficult to estimate $\mu_1, \ldots, \mu_K$ or $\theta_1, \ldots \theta_K$ (since there is no admixture and no recombination between populations). For the same reason, it is difficult to estimate the switch error rate (though that may be estimated based on known switch error rates for the phasing algorithm). Described herein are techniques for estimating $\mu_{x|y}$ and $\epsilon_{y,x}$. One way to perform this estimation is via the EM algorithm. However, here an alternative approach may be used that does not require iterative estimation. Recall that:

$$P(x_t^h | x_{t-1}^{h \oplus s_t}, y_t^h, y_{t-1}^{h \oplus s_t}) =$$

$$\begin{cases} \mu_{x_t^h | y_t^h} & \text{if } y_t^h \neq y_{t-1}^{h \oplus s_t} \\ \epsilon_{y_t^h, x_{t-1}^{h \oplus s_t}} \mu_{x_t^h | y_t^h} + \left(1 - \epsilon_{y_t^h, x_{t-1}^{h \oplus s_t}}\right) \mathbb{1}\{x_t^h = x_{t-1}^{h \oplus s_t}\} & \text{if } y_t^h = y_{t-1}^{h \oplus s_t} \end{cases}$$

The following assumptions may reduce the above equation:

Since all individuals are unadmixed, suppose that $y_t = y_{t-1} = y$

Assume that there is no switch error; (In case there is switch error, the Viterbi algorithm may be used to identify switch errors and "fix" the corresponding haplotypes.)

the previous equation reduces to (and for any specific choices of $x_t^h = j$ and $x_t^{h-1} = i$):

$$P(j|i,y) = \epsilon_{y,i} \mu_{j|y} + (1 - \epsilon_{y,i}) \mathbb{1}\{j=i\}$$

The cases in which $j=i$ may be somewhat hard to disentangle. For cases in which $j \neq i$, observe that $$P(j|i, y, j \neq i) = \frac{\mu_{j|y}}{\sum_{j':j' \neq i} \mu_{j'|y}}$$

The left side can be estimated directly based on counts from the data; the empirical estimate is denoted $\hat{P}(j|i,y,j \neq i)$. Rearranging the above equation gets the following linear equation:

$$\sum_{j:j \neq i} \hat{P}(j|i, y, j \neq i) \mu_{j'|y} - \mu_{j|y} = 0$$

By noting (2) for all combinations of i and j for which $i \neq j$, then a system of $$\binom{N}{2}$$

linear equations in N unknowns is obtained. The variable $\mu_{N|y}$ may be eliminated based on the linear constraint $\mu_{1|y} + \ldots + \mu_{N|y} = 1$ and then solve the remaining system of linear equations via least squares. Consider that:

$$\sum_{j:j \neq i} P(j|i) = \sum_{j:j \neq i} \mu_j$$

Again the probabilities on the left side can be empirically estimated, each $\epsilon_i$ may be estimated as $$\epsilon_i = \frac{\sum_{j:j \neq i} P(j|i)}{\sum_{j:j \neq i} \mu_j}$$

In some implementations, HMM recombination rate parameters are explicitly related to genealogical time. With this approach, inferred recombination rates are bounded above and below at different values depending on the total fraction of the genome that a particular ancestry is expected to comprise. In another implementation, recombination can be related to genealogical time by jointly estimating the recombination rates in/out of ancestries and the time that the individual may have had an ancestor from each population (like an ancestry timeline) based off the ancestry tract lengths. This approach may improve accuracy, trace ancestry, and/or anomalous chromosomes. Trace ancestry can be defined as 0.1% < ancestry composition proportions < 1%. Anomalous chromosomes are chromosomes that are greater than 95% of an ancestry assignment that is present at less than 5% in the rest of the genome.

While the above description has used an HMM as an example technique for smoothing and error correction of local classification calls, other techniques could be used. Examples of such other techniques include conditional random fields, recurrent neural networks, and convolutional neural networks. In some cases, approaches that use neural networks require an additional step of simulating training data for training the neural network parameters.

Posterior Aggregation for Hierarchical Classification

Intracontinental local ancestry inference is a challenging problem, and it may not always be possible to confidently determine whether a segment derives from, for example, Scandinavia or the British Isles, either because of lack of power or because the corresponding haplotypes occur at similar frequencies within the two populations. In some cases, it is possible to confidently determine that a segment derives from a specific broader region (e.g., Northern Europe). In certain embodiments, a procedure employs a defined multi-level population hierarchy (e.g., a four-level population hierarchy) that groups populations within continents and regions (See for example FIG. 24A). The K leaves (i.e., terminal nodes) of a hierarchy correspond to the K reference populations, and the highest level of hierarchy may have a single root node representing the union of all populations. Broadly, the levels beneath the root may correspond to continent-scale, regional-scale, and sub-regional-scale distinctions. Leaf nodes may occur at any of these levels; for example, Melanesia may, as illustrated in FIG. 24A, be placed in a first level of the hierarchy, e.g., at the continent scale, and is not further subdivided.

For a given window or segment, the procedure may sum the posterior probabilities from the leaves to the root of the tree, so that each node is assigned a probability equal to the sum of its children's probabilities, with the probability at the root always equal to one. The procedure may assign each window to the lowest node (i.e., the node closest to the leaves) at which the posterior probability exceeds a specified precision level, t∈[0.5, 1). In the worst case, no node other than the root has a posterior probability exceeding t. In this case, the procedure does not classify the window. If assignment probabilities are well calibrated, this procedure may ensure that the precision of the assignment is at least t. Therefore, t may be referred to as the nominal precision threshold.

Examples

Using an individualized HMM smoother, as described here, has been found to reduce the amount of broad geographic ancestry assignments as well as anomalous chromosome results. In one example, model evaluation employed simulating 1000 individuals for each of nine population categories: African American, Ashkenazi Jewish, East Asian, Latino, Middle-Eastern, North European, Other, South Asian, and South European. Ancestry composition was determined for these individuals using two different techniques as described above: one employing a training algorithm based across many individuals at the same chromosome as described in relation to FIG. 22A (hereinafter "population-based APHMM"), and the other technique employing a training algorithm across the genome for a single individual as described in relation to FIG. 22B (hereinafter "individual-based APHMM"). The tables below and FIGS. 23A-E present various analysis of these results. The table below presents the difference in Precision and Recall between these techniques. Precision describes how often the predicted ancestry composition is correct, and recall describes how often the correct ancestry composition is predicted. Positive numbers indicate an improvement in precision or recall, respectively, from the population-based APHMM to the individual-based APHMM. Generally, precision and recall increased across all ancestries.

| Population | Change in Precision between Population-based APHMM and Individual-based APHMM | Change in Recall between Population-based APHMM and Individual-based APHMM2 |
|---|---|---|
| Root | 0 | 0 |
| Subsahara | 0.2 | 0.8 |
| West Africa | −1.3 | 5.1 |
| Senegambia Guinea | 6.9 | 5 |
| SW West Africa | 2 | 5.3 |
| Nigeria | −2.2 | 11.8 |
| North East Africa | −9.1 | 6.7 |
| Sudan | −4.2 | 16.2 |
| Ethiopia Eritrea | −7 | 9.8 |
| Somalia | −5.8 | 6.7 |
| Congo South East Africa | 2.5 | 2.8 |
| Congo | −0.9 | 9.9 |
| South East Africa | 6.7 | 6.6 |
| San Pygmy | 10.7 | 5.3 |
| East Asia and Americas | 0.6 | 0.6 |
| Japan Korea | 0.5 | 5 |
| Japan | 6 | 8.3 |
| Korea | 5 | 15.5 |
| China Sea | 0.6 | 1.6 |
| China | 0.8 | 6.4 |
| Dai | 5.9 | 9.9 |
| Vietnam | 4.6 | 20.1 |
| Philippines | 1.7 | 6.9 |
| Sea Other | 22.5 | 13.9 |
| North Asia | 12.2 | 19.7 |
| Mong Manch | 12.4 | 21.9 |
| Siberia | 6.7 | 14.4 |
| Americas | 0.8 | 5.1 |
| Melanesia | −2.3 | 10.6 |
| South Asia | 0.7 | 1.1 |
| North South Asia | 5.4 | 9.7 |
| Central Asia | 17.7 | 9.6 |
| North In South Pk | 4.2 | 22.5 |
| Bengal Ne India | 16.1 | 16.9 |
| Gujarat Patel | 0.3 | 8.6 |
| Southern Brahmin | 13.5 | 21.8 |
| South South Asia | 8.9 | 17.5 |
| South Sa Other | 8.7 | 23.6 |
| Kerala | 8.2 | 18.7 |
| Wana | 2.1 | 3.6 |
| North West Asia | 4.6 | 11.6 |
| Cyprus | 11.8 | 19.1 |
| Turkey | 20.2 | 7.9 |
| Cauc Assyria Iran | 2.2 | 27.7 |
| Arabia Levant Egypt | 7.2 | 10.3 |
| Arabia | 9.1 | 13.8 |
| Levant | 9.2 | 19.2 |
| Egypt Other | 11.2 | 18 |
| Copt | 8.9 | 27 |
| Maghreb | −0.6 | 10.4 |
| Europe | 0.4 | 2.1 |
| Nw Europe | 3.6 | 7.1 |
| Britain Ireland | 4.1 | 15.2 |
| Central West Europe | 11.9 | 13.2 |
| Scandinavia | 8.7 | 11.5 |
| Finland | −5.9 | 10.9 |
| South Europe | 5 | 12.9 |
| Iberia | 7.3 | 28.1 |
| Sardinia | 5.4 | 22.4 |
| Italy | 5.1 | 23.1 |
| Balkans | 7.5 | 16.6 |
| East Europe | 12.5 | 12.1 |
| Ashkenazi | 0.2 | 0.2 |

The following table presents additional metrics between the population-based APHMM and the individual-based APHMM. Accuracy describes how often the most probable predicted ancestry for a window is the correct ancestry. Unassigned Ancestry indicates a percentage of windows where no continent has a greater than 50% posterior probability. Broad Ancestry indicates a percentage of windows where no reference population had a greater than 50% posterior probability. Decreases to unassigned ancestry and broad ancestry are desirable. Anomalous chromosomes are chromosomes where more than 95% of the chromosome has ancestries that are present at less than 5% of the rest of the genome. True instances of this phenomenon are exceedingly rare and thus a lower number is desirable. The table presents the percentage of individuals having an anomalous chromosome. As may be seen in reference to the following tables, Accuracy, Broad Ancestry, Unassigned Ancestry, and Anomalous Chromosomes generally improved across most populations.

|  | Accuracy % | | Broad Ancestry % | |
| --- | --- | --- | --- | --- |
| Population | Population-based APHMM | Individual-based APHMM | Population-based APHMM | Individual-based APHMM |
| African American | 55 | 61 | 32 | 16 |
| Ashkenazi | 99 | 98 | 1 | 0 |
| East Asian | 84 | 88 | 5 | 1 |
| Latino | 62 | 70 | 32 | 14 |
| Middle-Eastern | 58 | 75 | 10 | 3 |
| North European | 56 | 63 | 17 | 6 |
| Other | 56 | 72 | 28 | 11 |
| South Asian | 63 | 77 | 19 | 2 |
| South European | 66 | 80 | 19 | 2 |

|  | Unassigned Ancestry % | | % Individuals with Anomalous Chromosomes | |
| --- | --- | --- | --- | --- |
| Population | Population-based APHMM | Individual-based APHMM | Population-based APHMM | Individual-based APHMM |
| African American | 2 | 0 | 6 | 2 |
| Ashkenazi | 0 | 0 | 1 | 2 |
| East Asian | 0 | 0 | 71 | 20 |
| Latino | 6 | 1 | 19 | 5 |
| Middle-Eastern | 1 | 0 | 90 | 46 |
| North European | 0 | 0 | 50 | 19 |
| Other | 2 | 0 | 56 | 17 |
| South Asian | 1 | 0 | 82 | 40 |
| South European | 1 | 0 | 83 | 43 |

Figure 23A:
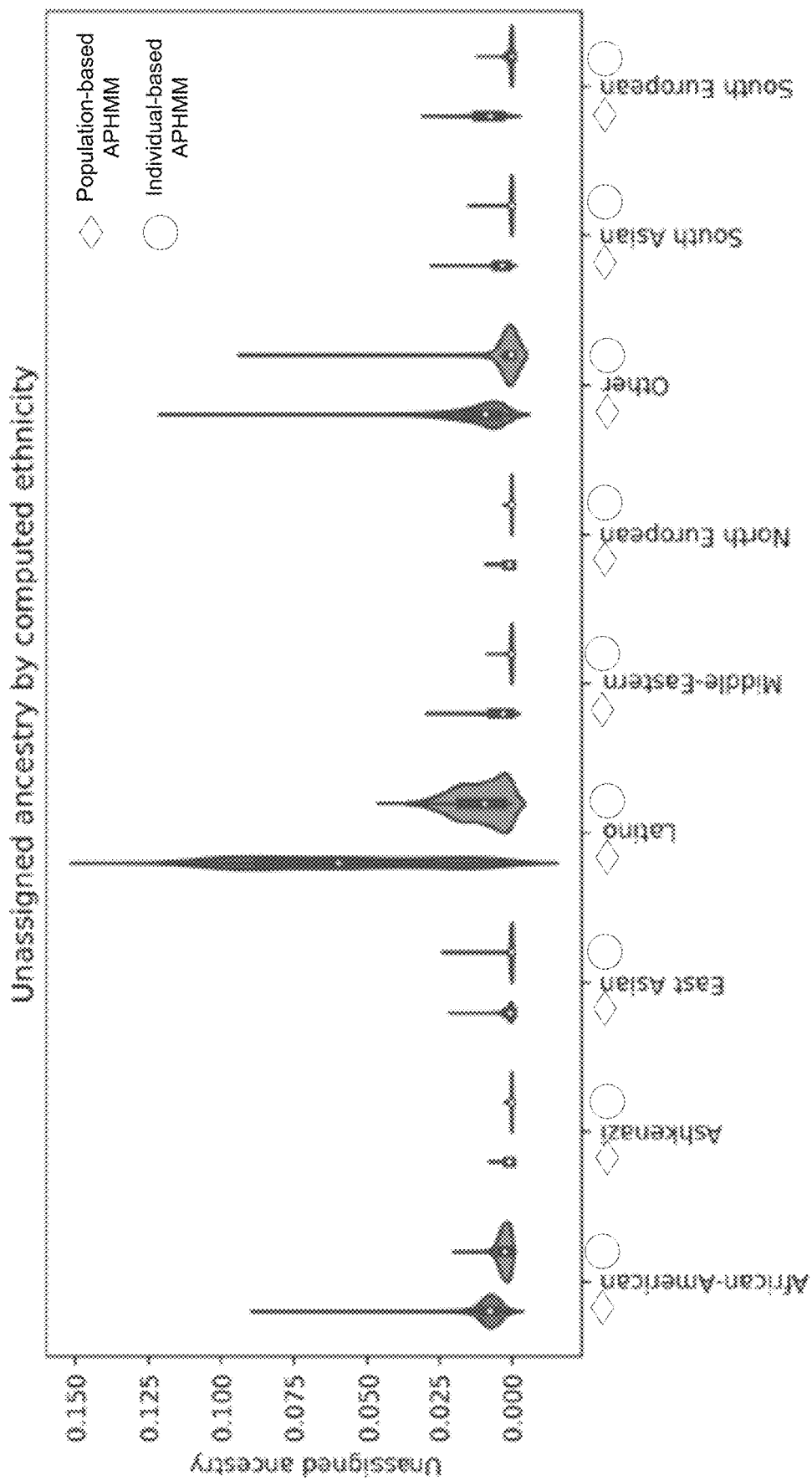
FIGS. 23A-E illustrate plots comparing performance of smoothing using a separate module for each chromosome and a single smoother module for all chromosomes.
Figure 23B:
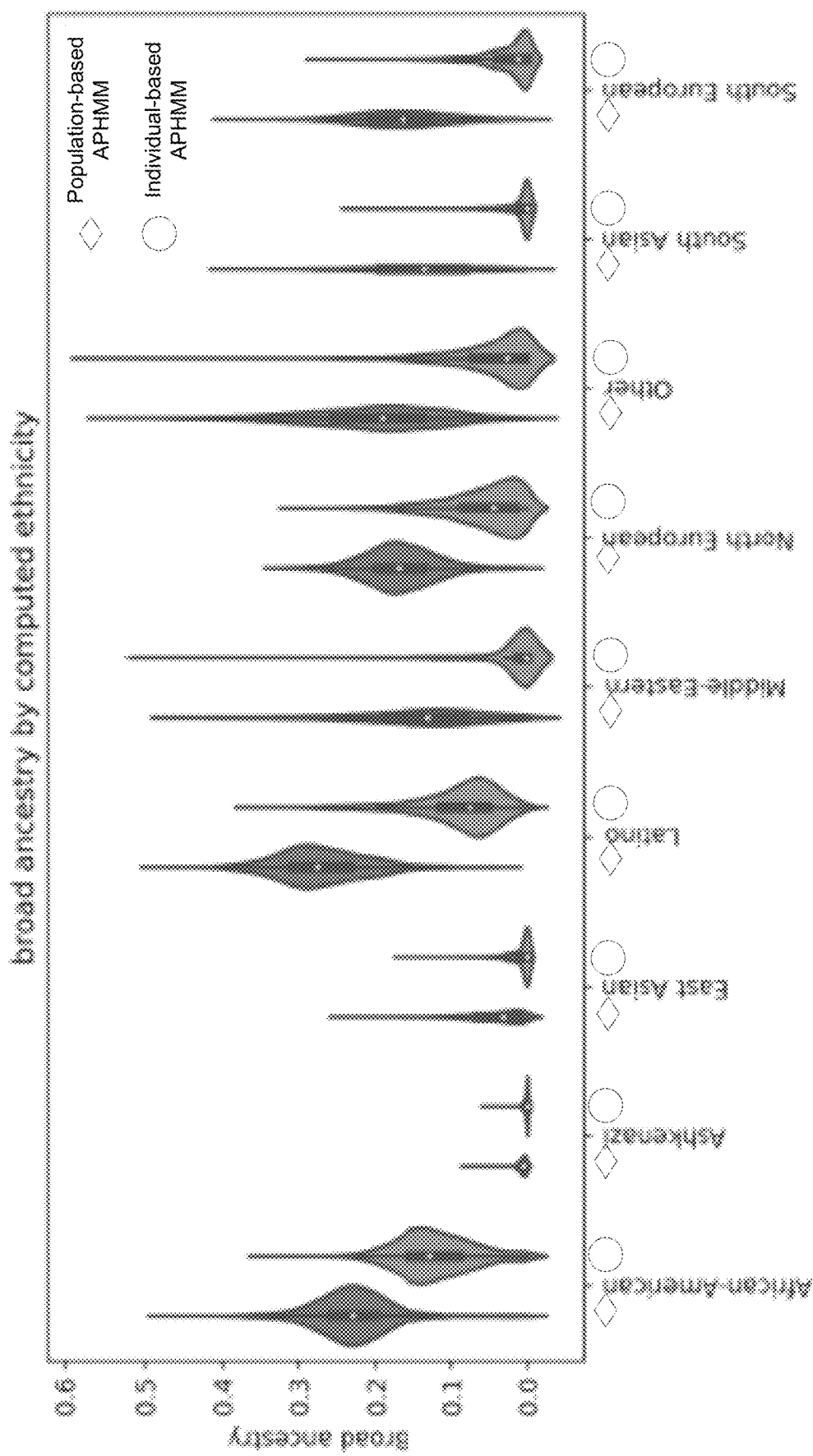
Figure 23C:
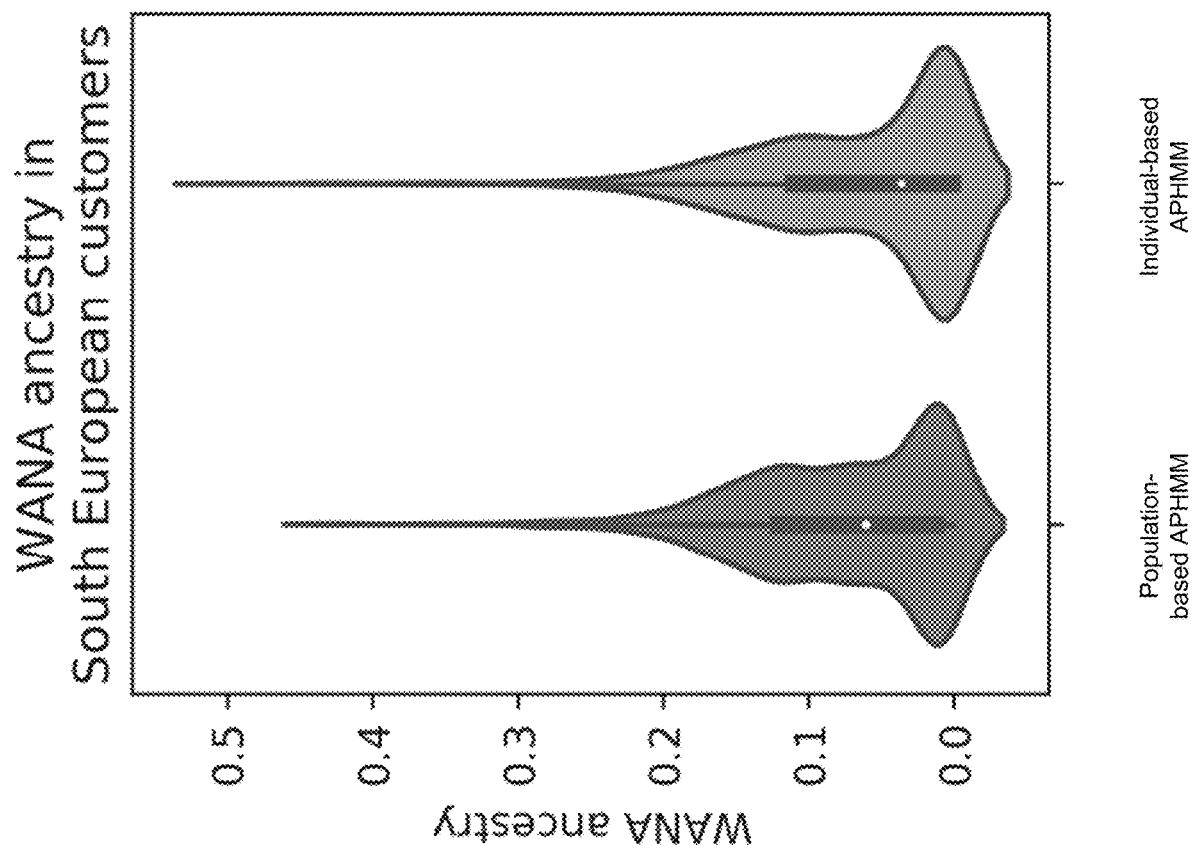

FIGS. 23A-E present additional analysis of the performance of the models above on classifying individuals. FIG. 23A illustrates unassigned ancestry for both the population-based and individual-based APHMM for different populations. Unassigned ancestry decreased using the individual-based APHMM method. FIG. 23B presents broad ancestry for both the population-based and individual-based APHMM for different populations. Broad ancestry refers to determining an ancestry that is not defined at the leaf level on a population hierarchy (see FIG. 24A). Broad ancestry decreased using the individual-based APHMM method. FIG. 23C presents West Asian North African (WANA) ancestry for south European individuals. A decrease in WANA ancestry for this geographic ancestry generally indicates an improved accuracy of the method. WANA decreased using the individual-based APHMM method.

Figure 23D:
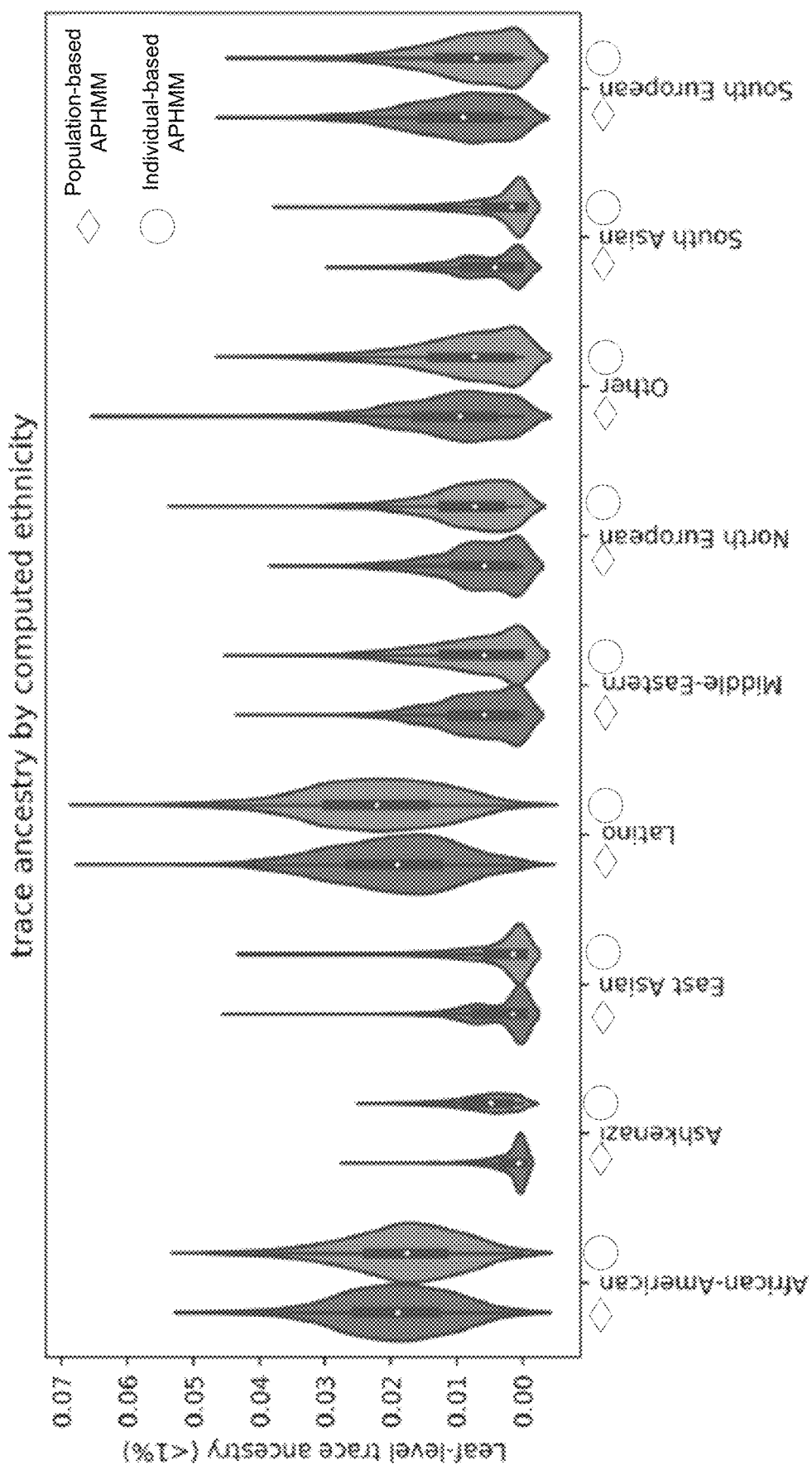
Figure 23E:
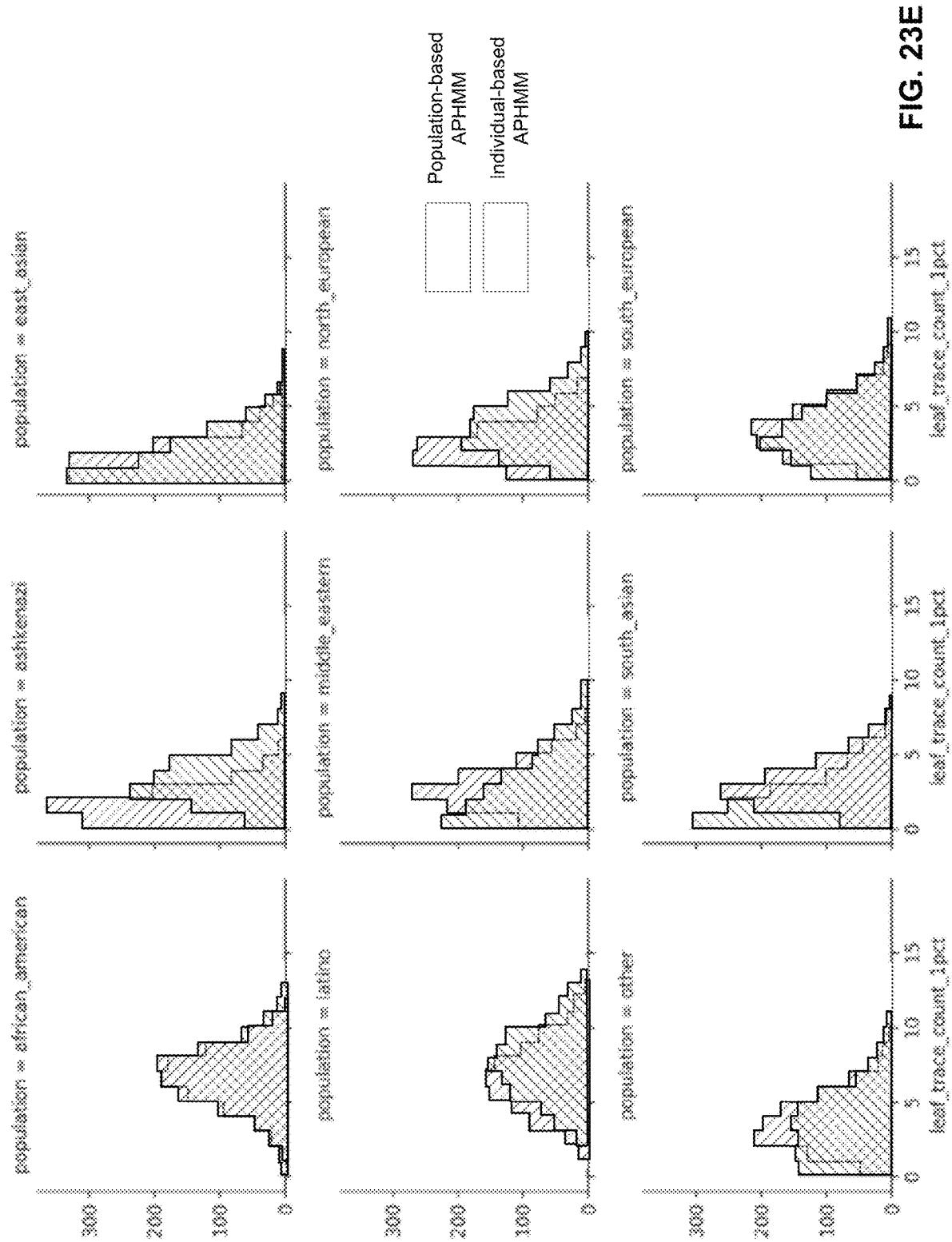

FIGS. 23D and 23E present graphs of trace ancestry for both the population-based and individual-based APHMM for different populations. Trace ancestry can be defined as an ancestry having a proportion of the total ancestry between 0.1% and 1% or less than 1%. This is generally unlikely, and thus reducing trace ancestry may improve ancestry composition results. As may be seen, for some population categories a single smoother module method, such as an individual-based APHMM, has improved trace ancestry results compared to a multiple smoother module method, such as a population-based APHMM. In particular, South Asian and South European populations had reduced trace ancestries using a single smoother module method.

In another example, model estimation and evaluation employed a stratified five-fold cross-validation approach, maintaining similar representation among the K=45 reference populations within each fold. For each fold, the procedure estimated local-classifier parameters using a training set composed of the ~80% of individuals assigned to the other folds. As each individual in the training panel for a given fold was in the hold-out validation panel for another fold, the procedure could classify each window of each chromosome copy using models trained with the individual held out, yielding hard-clustering vectors, $(c_1, c_2)$, for each chromosome of each individual in the cross-validation fold's training set. To estimate smoother emission parameters, including the autoregression transition matrix E, the procedure used a modified supervised EM algorithm applied to these hard-clustering vectors.

In one implementation of ancestry composition, a model estimation procedure estimated APHMM transition parameters using an unsupervised EM training procedure that relied on the natural admixture found in a broader set of 23andMe customers. Specifically, the procedure estimated transition parameters for samples of ~1000 unrelated 23andMe customers from each of the following population groups: African-American, Ashkenazi Jewish, East Asian, European, Latino, Middle-Eastern, and South Asian. These groups are termed "smoother training pools". For each individual to whom the ancestry composition prediction was applied, the procedure combined the predictions of each smoother training pool's model using Bayesian model averaging.

In another implementation of ancestry composition, a procedure inferred distinct, individualized APHMM transition parameter values for each individual to whom an ancestry composition prediction was applied. Individualized APHMM transition parameters were inferred using the same EM algorithm that was used to infer transition parameters for each smoother training pool, except that information was aggregated only across the 46 hard-clustering vectors for each individual. To encourage convergence to sensible transition parameter values, the procedure initialized transition parameter optimization from the pretrained transition parameter sets of the smoother training pools. To determine which smoother training pool will be used to provide the initial values for transition parameter optimization, the procedure used a multinomial Naive Bayes classifier trained on the hard-clustering assignments of all individuals in all smoother training pools. For each query individual to whom the ancestry composition was applied, the transition parameter values were initialized with those of the smoother training pool chosen by the Naive Bayes classifier when applied to the query individual's hard-clustering vectors. It was found that this individualized transition-parameter optimization affords the error-correction module a great degree of flexibility and ultimately reduces bias and increases accuracy.

In this example, an ancestry composition's classification performance was evaluated using precision and recall measures computed via the five-fold stratified cross-validation experiment. The evaluation estimated (a) precision for population k as the proportion of windows predicted to derive from population k that actually do derive from population k, and (b) estimated recall for population k as the proportion of windows truly deriving from population k that were predicted to derive from population k.

FIG. 24B shows accuracy results at continental, regional, and sub-regional scales, as described with respect to FIG. 24A. At each level of the population hierarchy, the evaluation estimated precision and recall for two precision thresholds: $t \in \{0.5, 0.8\}$. Note that increasing the threshold increases precision at the expense of recall.

At the continental scale (i.e., for all non-leaf populations that are children of the root node), precision exceeds 97% and recall exceeds 92% when t=0.5. When t=0.8, precision is greater than 99% for all continents except Europe, which achieves a precision of 98.3%, and recall drops slightly, with a minimum of 89.4% for West Asia and North Africa.

At the regional scale (i.e., considering the twelve non-continent non-leaf populations), precision and recall are uniformly less than or equal to the continent-scale parent populations, by definition. With nominal precision threshold t=0.5, precision remains fairly high, with a median of 95.2% and exceeding 90% for all but North Asia and Northwest Asia. Recall for t=0.5 is also relatively good at this scale, with a median of 94.5%. It exceeds 90% for eight of twelve regions and exceeds 80% for all. At nominal precision threshold t=0.8, precision has median 97.5% and is greater than 90% for all regions except North Asia and Northwest Asia. Recall decreases slightly but still remains above 85% for most populations.

At the leaf level, many populations continue to have good precision and recall metrics. Seven of 45 leaf populations (namely, Ethiopia & Eritrea, Congo, Japan, Korea, China, Gujarati Patel, and Ashkenazi) achieved precision and recall above 95% for both nominal precision thresholds, and 17 of 45 leaf populations achieved precision and recall above 90% for both precision thresholds. At nominal precision threshold t=0.5, the median precision is 96.1% for all leaf-level populations, with 35/45 leaf-level populations having precision at least 90% and 41/45 populations having precision at least 80%. Recall at t=0.5 has median 91.1%, with 26/45 leaf-level populations exceeding 90% and 38/45 populations exceeding 80%. As at the continental and regional scales, precision increases slightly and recall decreases slightly with nominal precision threshold t=0.8 compared to t=0.5.

In another example, FIGS. 24C-G present tables showing ancestry composition for computed ethnicities of individuals for different populations using a multi-module (e.g., population-based APHMM) and a change in ancestry composition between the computed ethnicities from a multi-module process and computed ethnicities from a single-module process (e.g., individual-based APHMM). By using a single-module process as described herein, various ancestry composition determinations were improved to reduce broad and/or anomalous ancestries. For example, Southern European ancestry compositions changed to have greater specificity from the sub-regional level of South Europe to the leaf level of Italy and Iberia. Similar examples of greater specificity between regional or sub-regional levels to leaf levels are illustrated for most of the populations except for Ashkenazi Jewish, which is highly specific using either method. The hierarchy between different levels may be understood with reference to FIG. 24A, discussed above.

Recalibration

Figure 25A:
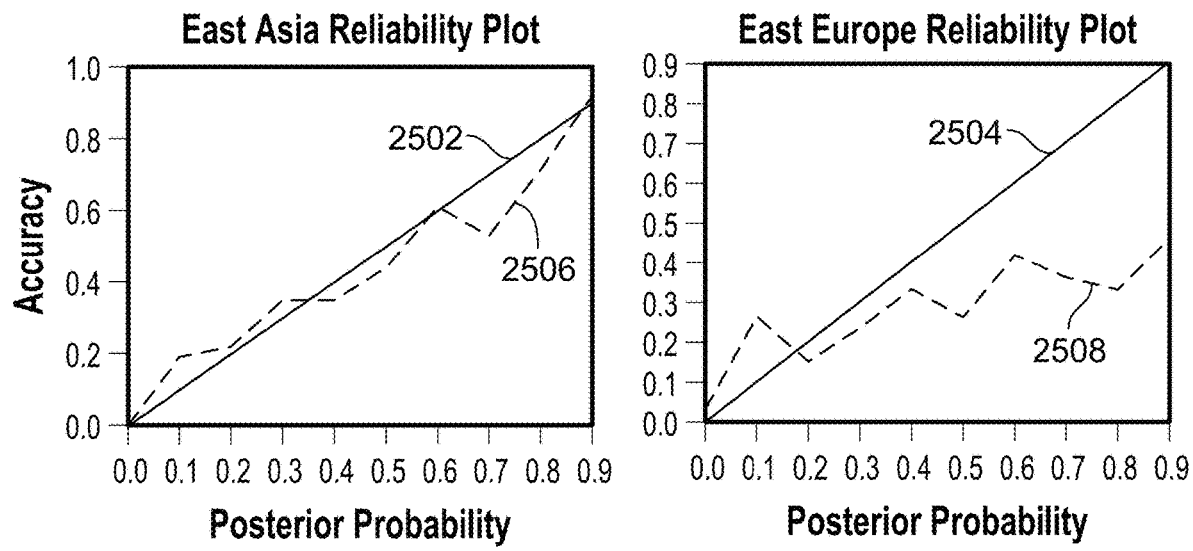
FIG. 25A illustrates example reliability plots for East Asian population and East European population before recalibration.

The error correction module outputs the most probable sequence of ancestry assignments for a pair of haplotypes, and posterior probabilities associated with the corresponding assignments. The posterior probabilities are recalibrated to establish confidence measures associated with the ancestry assignments. A well calibrated prediction with a probability of P should be correct P of the times. How well the posterior probability of the output is calibrated can be determined based on reference data of actual unadmixed individuals and/or simulated admixed individuals. For example, if it is known that in the reference data, 10% of the haplotype segments correspond to East European ancestry, but the output predicts with 80% posterior probability that 20% of all the haplotype segments correspond to East European ancestry, then the posterior probability is overly confident. By tallying the percentage of the reference data that corresponds to a specific ancestry, and applying the reference data to the predictive engine to obtain the posterior probability, a reliability plot of accuracy vs. posterior probability can be determined for each reference population corresponding to a specific ancestry. FIG. 25A illustrates example reliability plots for East Asian population and East European population before recalibration. In the example plots shown, lines 2502 and 2504 indicate the ideal accuracy-posterior probabilities correspondence, and lines 2506 and 2508 indicate the actual accuracy-posterior probabilities correspondence. Other reliability plots can be similarly determined.

In some embodiments, Platt's recalibration technique is used to recalibrate the posterior probabilities. Logistics regression is applied to posterior probabilities. A feature matrix X (e.g., $2^{nd}$ degree polynomials) is defined, and a fit is determined based on the following:

$$Pr(y=1|X) = \frac{1}{1 + \exp(X\theta)}$$

K-class recalibration is then performed (K being the number of ancestries). In some embodiments, K logistic curves are fit and renormalized. In some embodiments, K logistic curves are fit and multinomial logistic regression (i.e., softmax) is performed according to the following:

$$Pr(y=i|X) = \frac{\exp(X\theta_i)}{1 + \sum_{k=1}^{K-1} \exp(X\theta_i)} \forall i \leq K$$

Figure 25B:
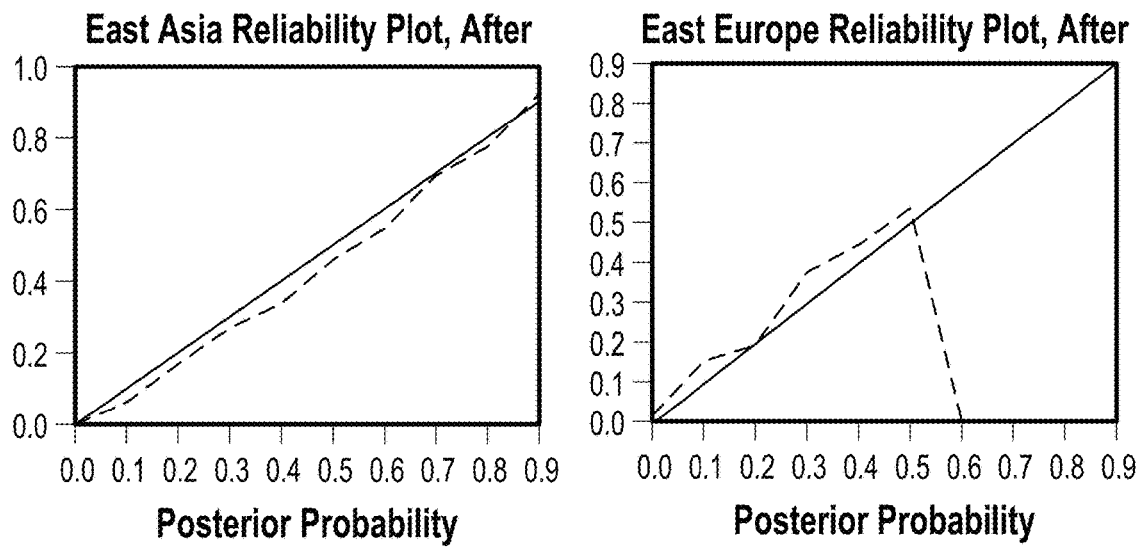
FIG. 25B illustrates example reliability plots for East Asian population and East European population after recalibration.

FIG. 25B illustrates example reliability plots for East Asian population and East European population after recalibration. It is worth noting in the original East European plot of FIG. 25A, when the posterior probability exceeds 60%, the accuracy is very poor. Thus, in the calibrated result for East European population shown in FIG. 25B, accuracy is clipped at 60%.

In some embodiments, an isotonic regression technique (e.g., the Zadrozny and Elkan method) is used to recalibrate the posterior probabilities, where recalibrated probabilities are estimated as percentages of well classified training examples falling in each bin.

Given the input of $(y_i, p_i)=1$, n, the input is sorted in increasing order of $p_i$. $\phi_i$ that monotonically increases with $p_i$ but close to $y_i$ are found. In some embodiments, a pool-adjacent-violators (PAV) algorithm is used to solve:

$$\min_{\phi_1,\ldots,\phi_n} \sum_{i=1}^{n} (y_i - \phi_i)^2$$

$$\phi_1 \leq \phi_2 \leq \ldots \leq \phi_n$$

where $y_i$ is the label predicted for individual i, $p_i$ is the uncalibrated probability associated with the prediction and $\phi_1$ is the recalibrated probability.

In some embodiments, modified isotonic regression techniques are used. For example, $p_i$ can be bracketed into bins, and weights proportional to the bin sizes are introduced to reduce computational cost. As another example, regularization terms can be introduced to ensure smoothness of the output curves as follows:

$$\min_{\phi_1,\ldots,\phi_n} \sum_{i=1}^{n} \omega_i(y_i - \phi_i)^2 + C \sum_{i=1}^{n-1} (\phi_i - \phi_{i+1})^2$$

$$\phi_1 \leq \phi_2 \leq \ldots \leq \phi_n$$

In some embodiments, separate calibration regimes are used for individuals with different amounts of effective switch error. Specifically, separate calibration curves are fitted for unadmixed individuals (who have a low rate of effective switching error) or admixed individuals (who have a high rate of effective switching error).

Label Clustering

Figure 26A:
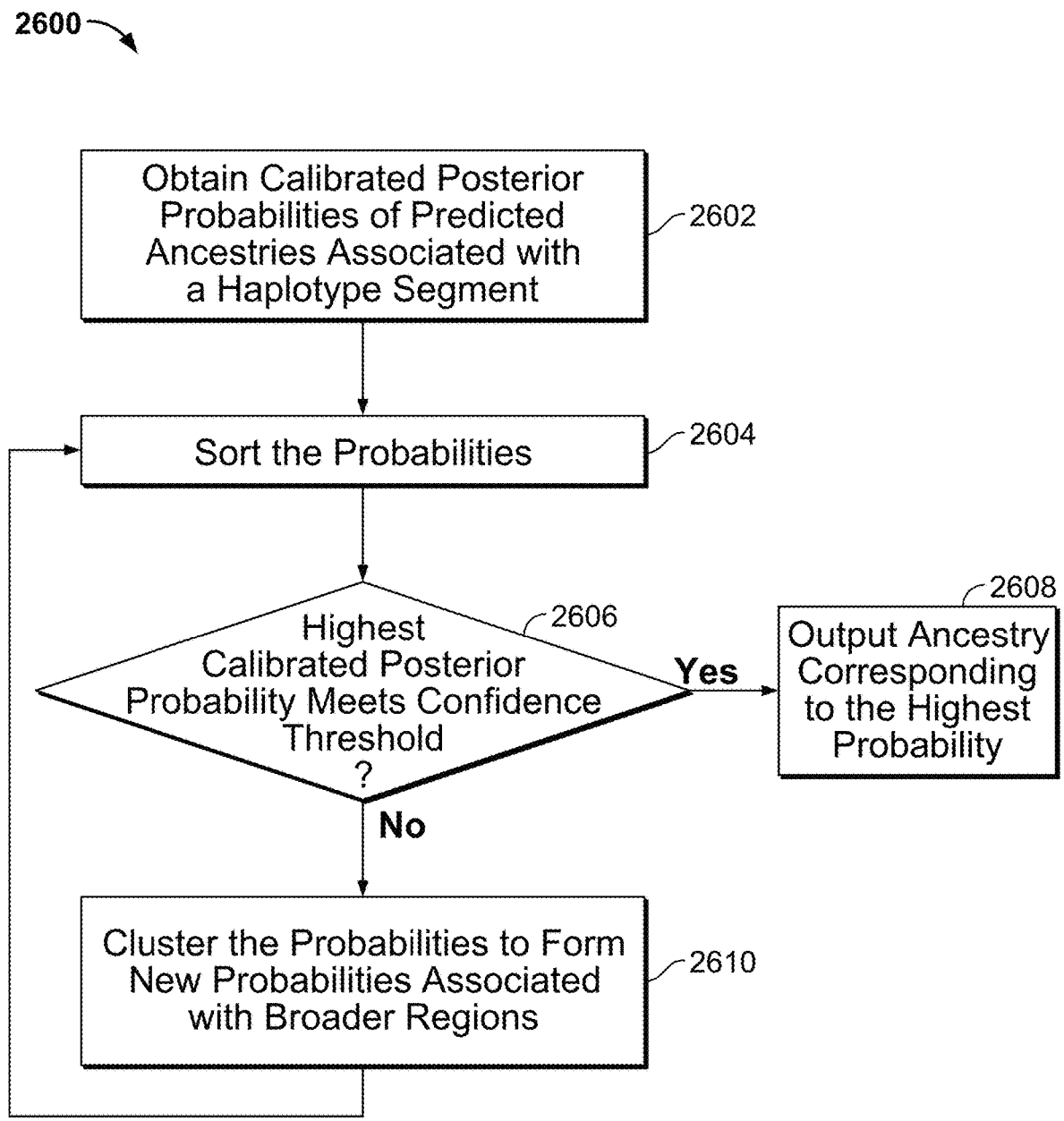
FIG. 26A is a flowchart illustrating an embodiment of a label clustering process.

In some embodiments, the recalibrated results are required to meet a threshold level of confidence before they are presented to the user. If the threshold level is unmet, the assignments are clustered and repeated as necessary until a total confidence level meets the threshold level. FIG. 26A is a flowchart illustrating an embodiment of a label clustering process. Process 2600 can be performed on a platform such as 200 or a system such as 300. At 2602, calibrated posterior probabilities of predicted ancestries associated with a haplotype segment are obtained (for example, as output of the calibration module). At 2304, the calibrated posterior probabilities are sorted according to their values. At 2606, it is determined whether the calibrated posterior probability with the highest value meets the threshold. If so, the ancestry associated with the highest calibrated posterior probability is deemed to be the ancestry of the haplotype segment and is output (e.g., presented to the user) at 2608. If, however, the threshold is not met, then, at 2610, the probabilities are clustered (e.g., summed) to form one or more new probabilities associated with broader geographical regions, and the new probabilities are clustered again at 2604. 2604-2610 are repeated until the threshold is met and a predicted ancestry of sufficiently high confidence is presented to the user.

Figure 26B:
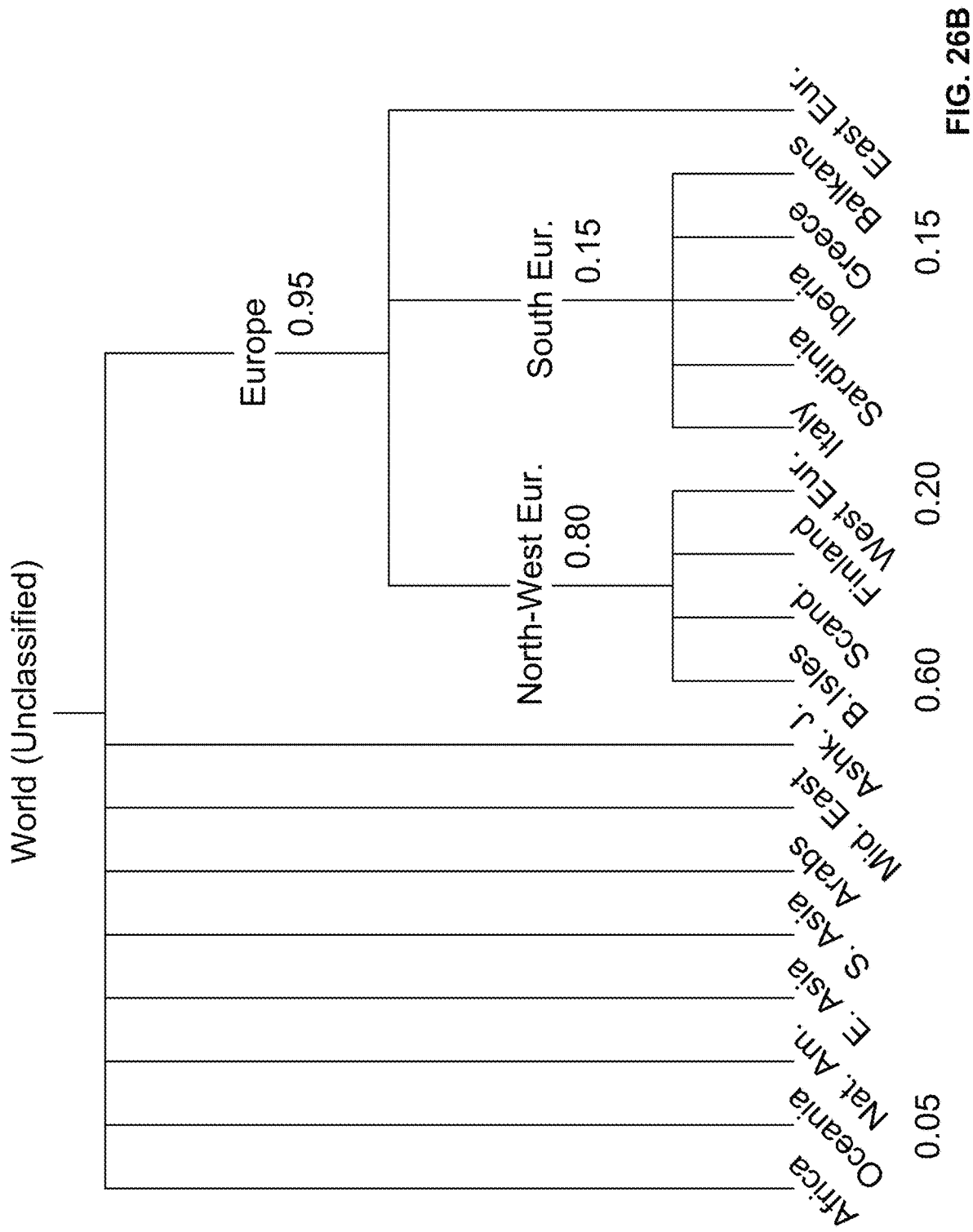
FIG. 26B is an example illustrating process 2600 of FIG. 26A.

FIG. 26B is an example diagram illustrating process 2600 of FIG. 26A. In this example, geographical locations associated with different ancestries are organized into a hierarchical tree. The root node of the tree is the world (a segment that is labeled the world means that the segment is unclassified). The next level corresponds to the continents. The next level under the continents corresponds to subcontinents. The next level corresponds to individual countries or specific geographical regions within each subcontinent. Other representations are possible. The calibrated posterior probabilities of predicted ancestries associated with the haplotype segment are as follows: 5% probability of being Oceania, 60% probability of being British Isles, 20% probability of being West Europe, 15% probability of being Greece. Depending on the value set for the threshold, different predicted ancestries can be presented. For example, if the probability is set at 60%, the ancestry of British Isles is deemed to be associated with the segment and is presented to the user. If the threshold is set at 70%, then none of the current ancestry labels meets the threshold level. Thus, the probabilities associated with specific countries or regions are clustered into subcontinents and the probabilities are summed. As shown, the probabilities associated with the British Isles and West Europe are clustered to form a probability indicating that the segment is 80% likely to be North-West European in its origin. The segment would therefore be labeled as North-West European. If, however, the threshold is set at 90%, then even at this level, no probability associated with a single node of the hierarchical tree meets the threshold. Thus, the probabilities are clustered again, combining the probabilities of North-West Europe and South Europe to form a probability that the segment is 95% likely to be from Europe. Europe is then presented as the predicted ancestry associated with the segment. As shown, if a segment cannot meet the threshold at the continental level, it is deemed to be world/generic.

The output of the label cluster outputs the predicted ancestry for each haplotype segment. In some embodiments, the information is stored in a database and/or sent to an application to be displayed.

Display of Ancestry Composition Information

In some embodiments, once the ancestries associated with the individual's chromosomes are determined, the results can be presented via various user interfaces upon user requests. The user interfaces can also present ancestry information obtained using other techniques so long as the data being presented includes requisite information such as the specific ancestries and proportions of the individual's genotype data that corresponds to the specific ancestries.

Figure 27:
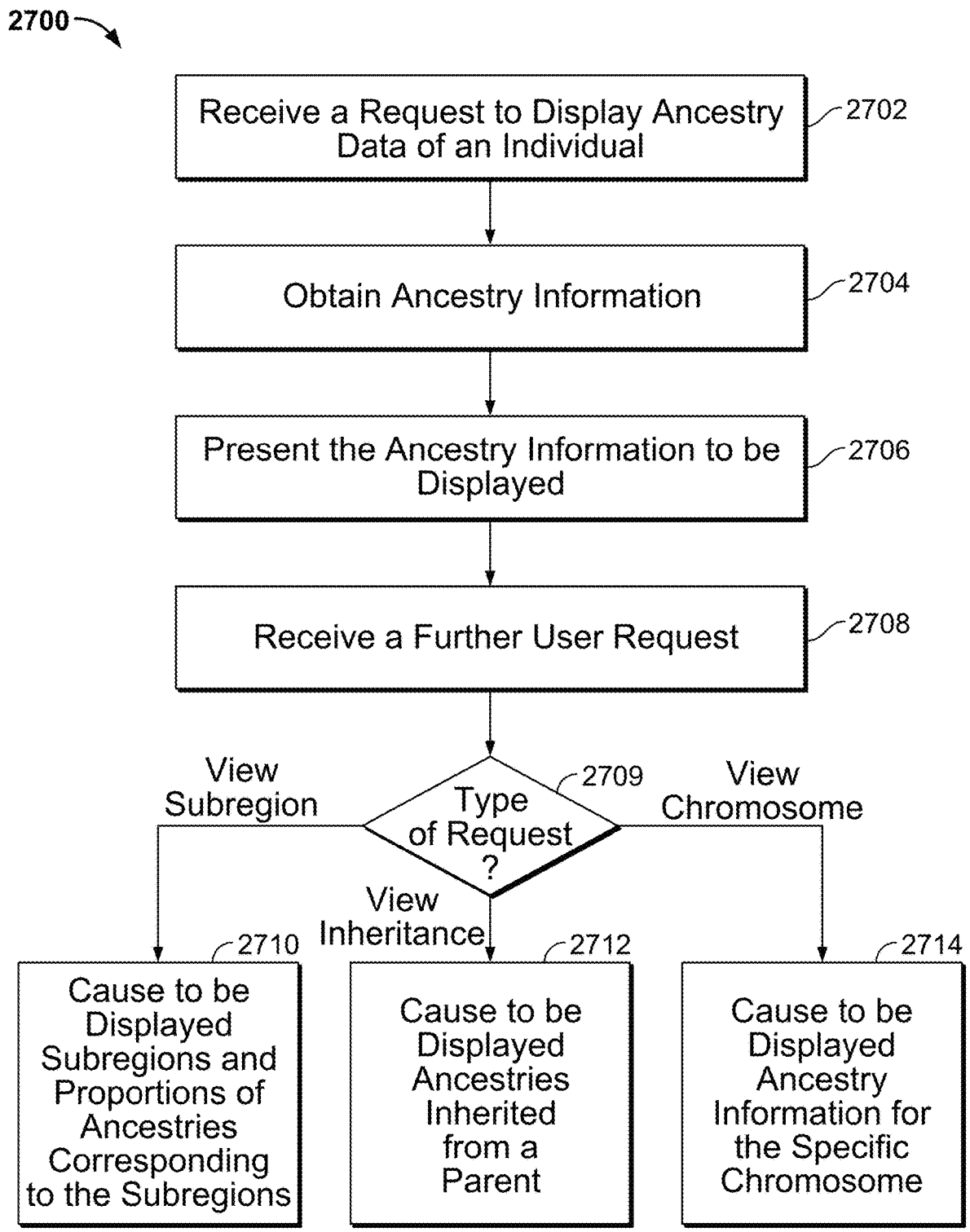
FIG. 27 is a flowchart illustrating an embodiment of a process for displaying ancestry information.

FIG. 27 is a flowchart illustrating an embodiment of a process for displaying ancestry information. Process 2700 can be performed on a platform such as 200 or a device such as 100.

At 2702, a request to display ancestry composition of an individual is received. In some embodiments, the request is received from an application that allows users to interact with their genetic information and/or ancestry data. Referring to FIG. 2 as an example, a user can make a request to display ancestry information via an application (e.g., a standalone application or a browser-based application) installed on client device 202. The application provides user interfaces (e.g., buttons, selection boxes, or other appropriate user interface widgets) as well as associated logic to interact with ancestry prediction system 206 and/or process data. The user can be the individual or another person with permission to view the individual's ancestry information.

Returning to FIG. 27, at 2704, upon receiving the request and in response, ancestry composition information of the individual is obtained. The ancestry composition information includes information pertaining to proportions of the individual's genotype data deemed to correspond to specific ancestries. In some embodiments, the ancestry composition information includes hierarchical information of different geographical regions (e.g., 40% of the individual's genome corresponds to European ancestry, of which 80% corresponds to North-Western European ancestry and 20% corresponds to Southern European ancestry; of the North-Western European ancestry, 30% corresponds to Finish ancestry and 70% corresponds to Scandinavian ancestry; of the Southern European ancestry, 50% corresponds to Italian ancestry and 50% corresponds to Greek ancestry, etc.). In some embodiments, the ancestry composition information is obtained directly from a source such as a database or the output of a pipelined ancestry prediction process. In some embodiments, raw data obtained from a source is further processed to obtain ancestry composition information. For example, if the raw data only includes predicted ancestry composition information per haplotype segment, then the segments and their ancestries are tallied to determine the proportions of the individual's genes that are deemed to correspond to the specific ancestries (e.g., 1000 out of 5000 segments are deemed to correspond to Italian ancestry and therefore 20% of the individual's genes are deemed to correspond to Italian ancestry).

At 2706, the ancestry composition information is presented to be displayed via a user interface.

In some embodiments, the ancestry composition information is initially displayed according to geographical regions and proportions of ancestries deemed to correspond to those geographical regions. Subsequently, the user can request different data to be displayed via user interfaces provided by the application. A further user request is optionally received at 2708. At 2709, the type of request is determined. In response to the further user request and depending on the type of request, different information is displayed. As shown, if the user request is a request to display subregions of a specific ancestry, subregions and proportions of the individual's ancestries corresponding to the subregions are displayed (or caused to be displayed on a display device by processors) at 2710 in response. If the user request is a request to display ancestries inherited from one or more parents, such information is displayed (or caused to be displayed) at 2712 if available. If the user request is a request to display ancestry composition information for a specific chromosome, the proportions of ancestries associated with the specific chromosome is displayed (or caused to be displayed) at 2714. Other types of requests/displays are possible.

Figure 28:
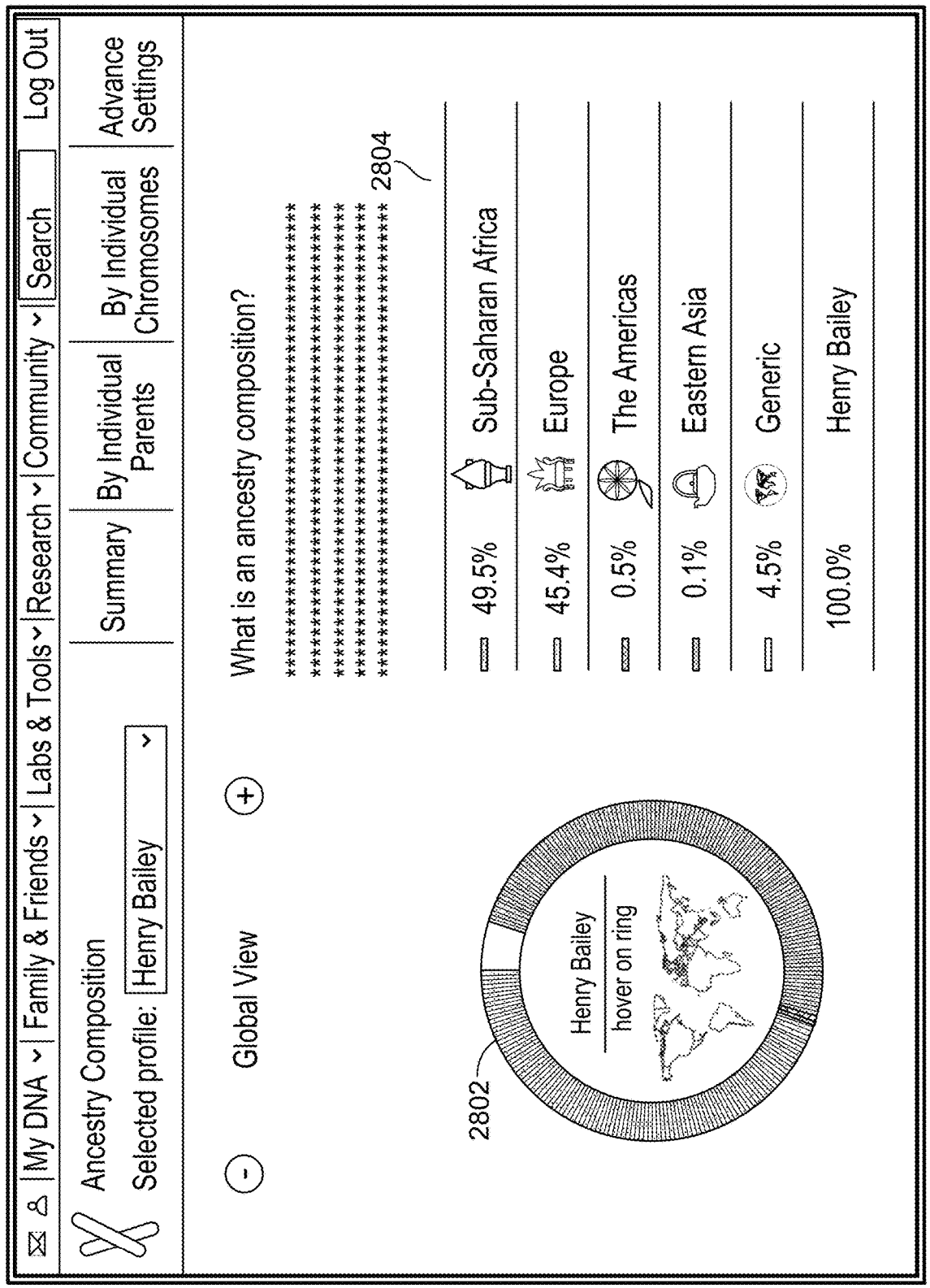
FIG. 28 is a diagram illustrating an embodiment of a regional view of ancestry composition information for an individual.

FIG. 28 is a diagram illustrating an embodiment of a regional view of ancestry composition information for an individual. In this example, proportions of the individual's autosomal chromosome segments that correspond to specific continents are displayed. The information is presented to the user using two different views: a circle view 2802 displaying the proportions as sections on a circle, where different visual formats (e.g., colors and/or patterns) represent different ancestral continents; and a list view 2804 displaying the proportions and corresponding continent names. Other views are possible (e.g., a map view displaying the regions associated with the ancestries).

Figure 29:
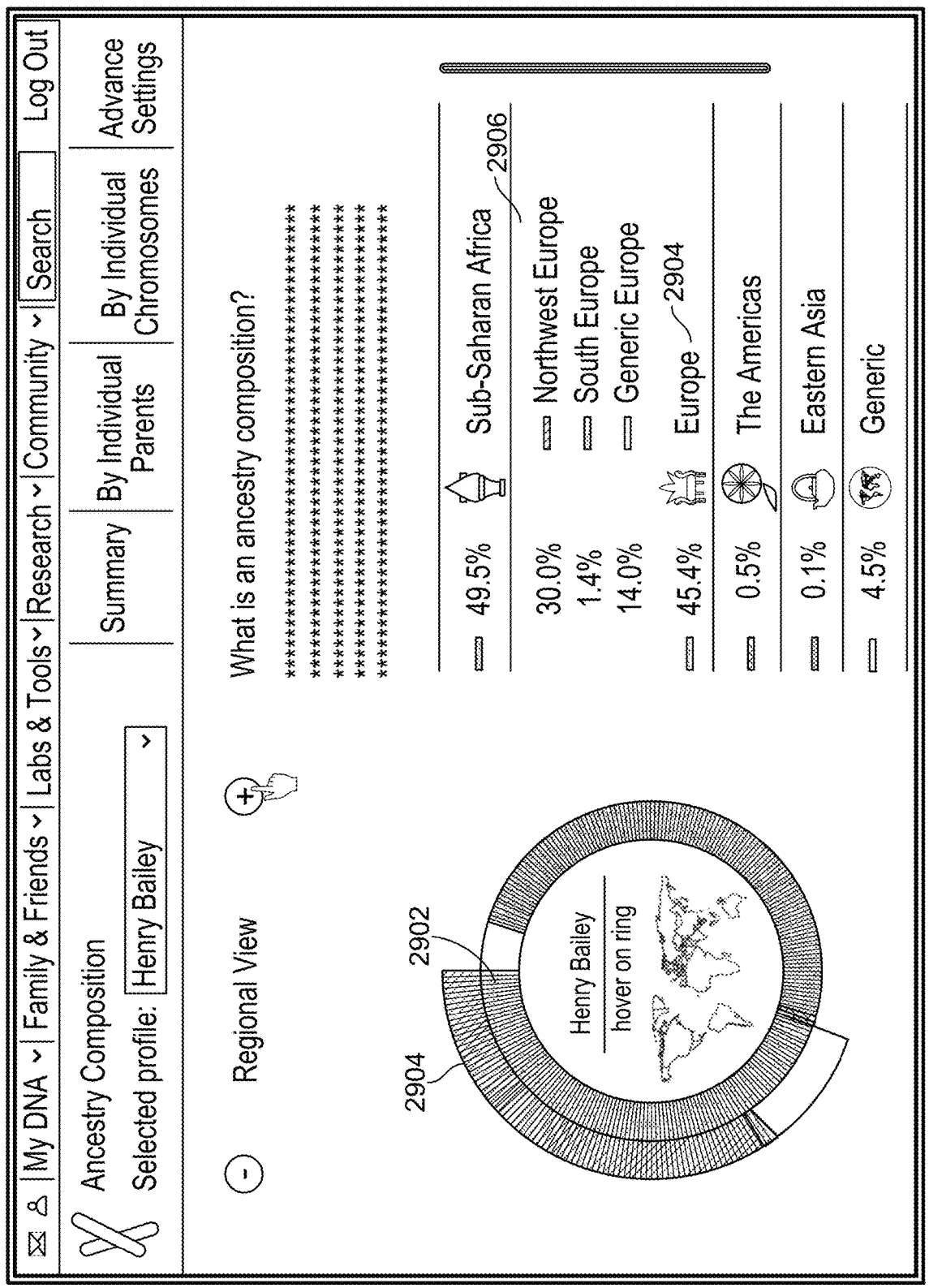
FIG. 29 is a diagram illustrating an embodiment of an expanded view of ancestry composition information for an individual.

The user is provided with the ability to expand the regions and view more detailed information pertaining to subregions. FIG. 29 is a diagram illustrating an embodiment of an expanded view of ancestry composition information for an individual. In this example, the user can request to expand the circle view by moving a cursor or other pointing mechanism over a section of the circle view (e.g., European section 2902), or by clicking on an entry in the list view (e.g., European entry 2904). In response, the application expands the section and/or the entry in the list to show subregions of ancestries for the individual. In some embodiments, the subregions are determined according to the hierarchical information of the ancestry composition information. In the example shown, a new section 2904 is created to include three subregions of Europe (Northwest Europe, South Europe, and Generic Europe) from which the individual's ancestries can be traced as well as proportions of the individual's DNA attributed to these subregions, and additional entries 2906 are created to list the subregions and the proportions.

Figure 30:
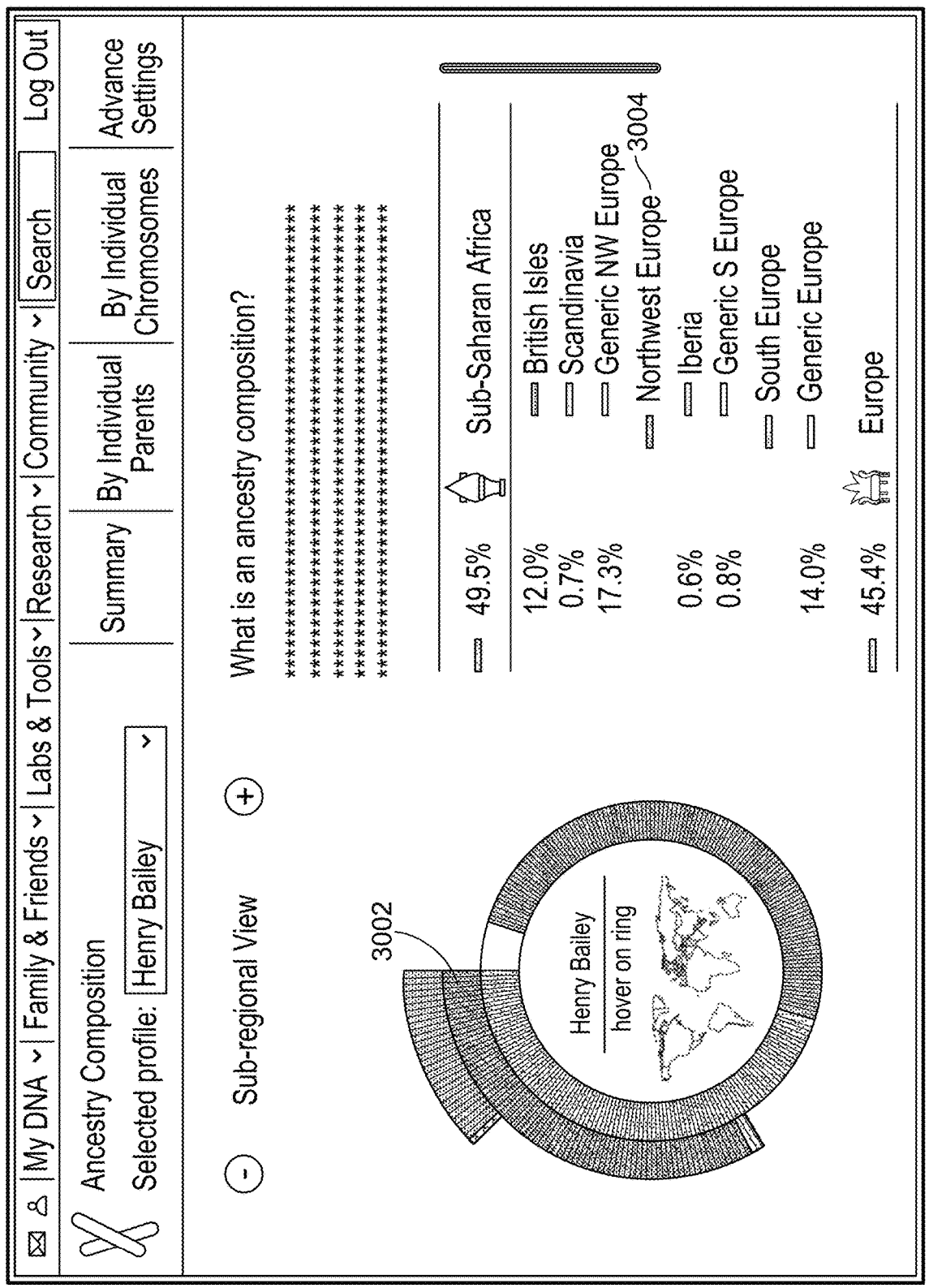
FIG. 30 is a diagram illustrating an embodiment of a further expanded view of ancestry composition information for an individual.

The subregions can be further expanded. FIG. 30 is a diagram illustrating an embodiment of a further expanded view of ancestry composition information for an individual. In this example, the user can request to expand the circle view by moving the cursor or other pointing mechanism over a subregion section (e.g., Northwest Europe section 3002), or by clicking on an entry in the list view (e.g., Northwest Europe entry 3004). In response, the application expands the subregion section and/or the entry to show more detailed composition. In this example, the Northwest European ancestry is shown to include ancestries from British Isles, Scandinavia, and generic Northwest Europe. The process can be repeated as long as more granular data is available.

Figure 31:
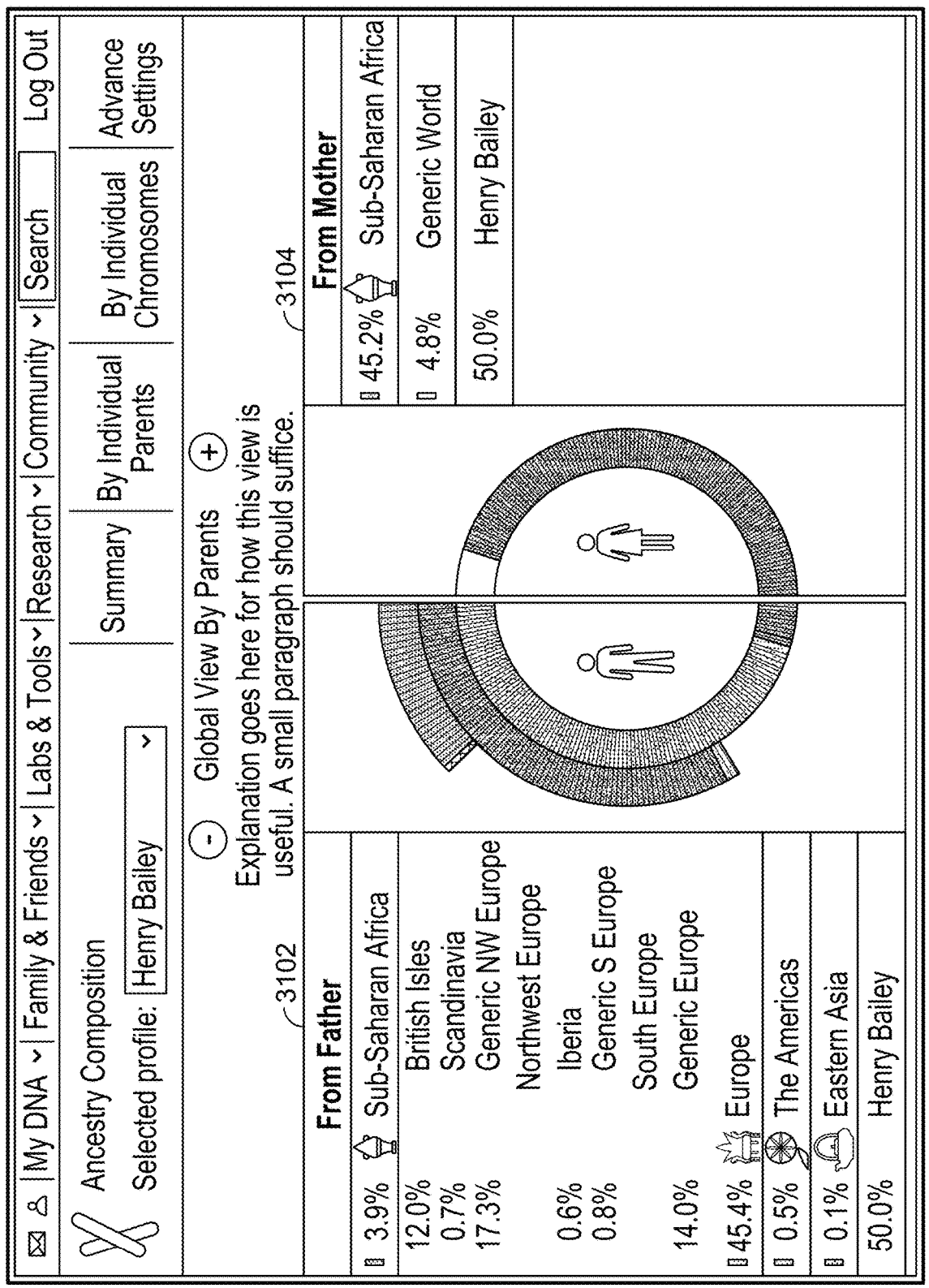
FIG. 31 is a diagram illustrating an embodiment of an inheritance view.

In some embodiments, the ancestry composition information that is obtained includes inheritance information, including proportions of the individual's ancestries that are deemed to be inherited from either the father or the mother. In other words, the inheritance information pertains to how much of the individual's DNA corresponding to a specific ancestry is inherited from each parent. For example, the trio-based phasing result can indicate that for chromosome 1, haplotype 0, segments 1-20 correspond to Scandinavian ancestry and are inherited from the mother, segments 21-45 correspond to Italian ancestry and are inherited from the mother also, segments 46-73 correspond to Greek ancestry and are inherited from the father, and so on. The segments from either the mother or the father and the corresponding ancestries of the segments are tallied, and proportions of the ancestries attributed to each parent are computed. The inheritance information computation can be done following trio-based phasing, at the time the request to display inheritance from parents is made, or at some other appropriate time. Ancestry composition information of how much of the individual's DNA corresponding to a specific ancestry is inherited from each parent is displayed. FIG. 31 is a diagram illustrating an embodiment of an inheritance view. In this example, the view is divided into two areas shown side-by-side. Area 3102 shows ancestries inherited from the father and area 3104 shows ancestries inherited from the mother. A continent-level view of ancestry composition attributed to each parent is shown initially. For example, 49.1% of the individual's DNA is deemed to correspond to sub-Saharan African ancestry, of which 3.9% is inherited from the father and 45.2% is inherited from the mother. The user is provided with the options to selectively view subregions in similar manners as described in connection with FIGS. 28-30.

Figure 32:
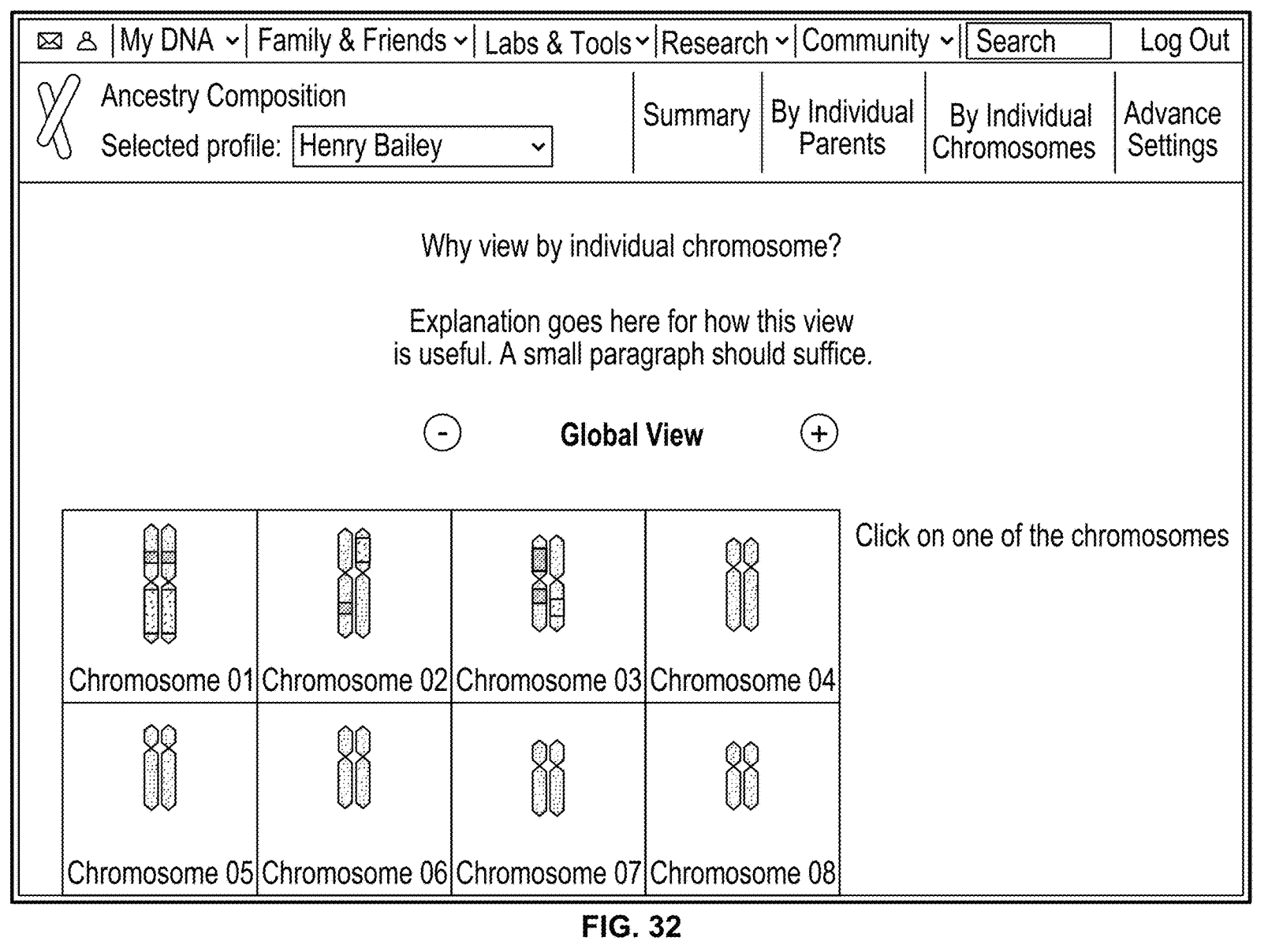
Figure 33:
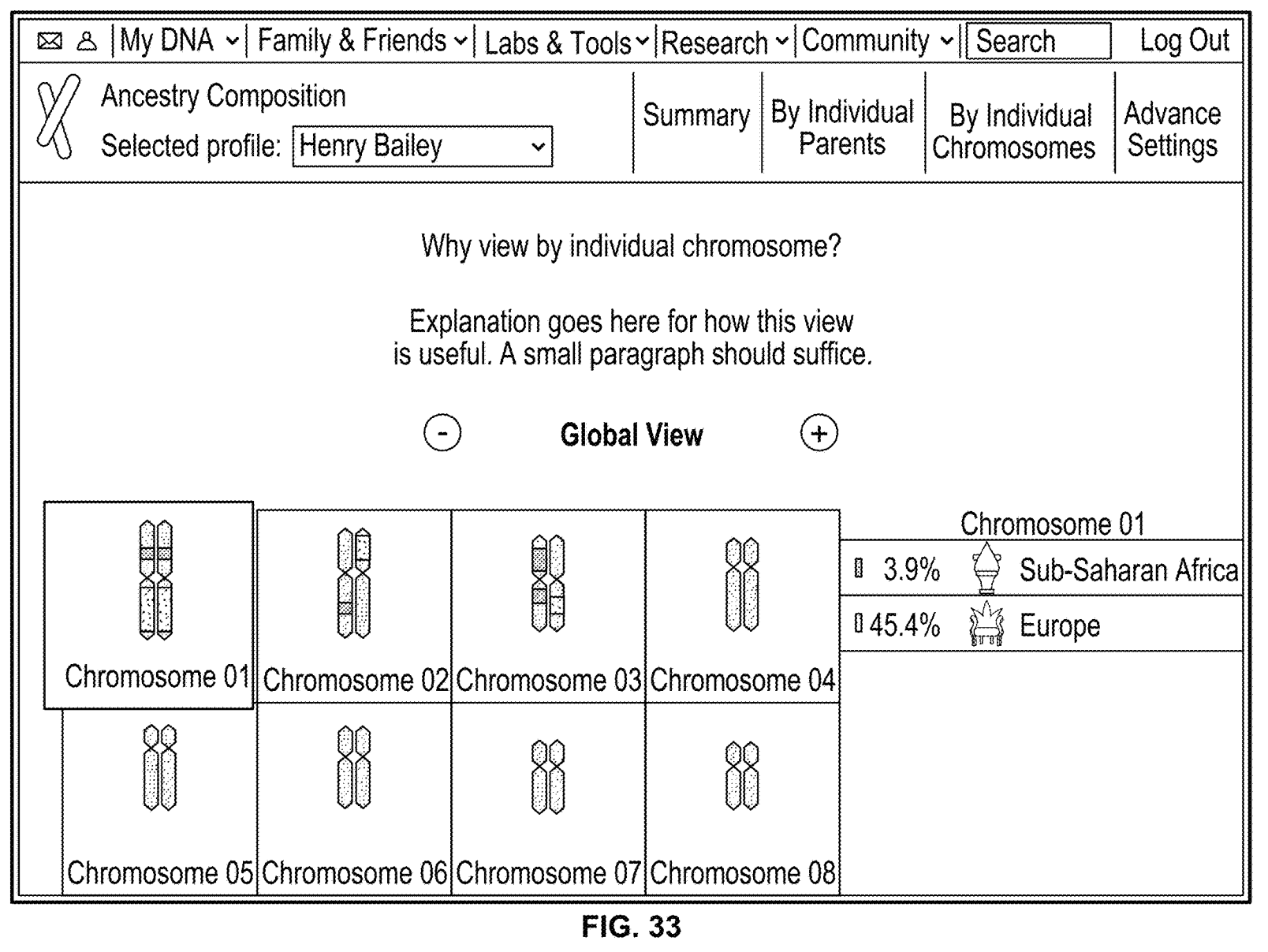

In some embodiments, since the ancestry deconvolution process is applied to individual chromosomes and the results are stored on the basis of individual chromosomes, the user has the option to select a specific autosomal chromosome or an X-chromosome to view its ancestral composition. FIGS. 32-33 are diagrams illustrating embodiments of a chromosome-specific view. In FIG. 32, a list of the autosomal chromosomes (and/or X-chromosome) that has undergone ancestry deconvolution is presented to the user. Only 8 chromosomes are displayed in the figure but more are available. The user has the option to select a specific one to view its ancestral composition. Upon receiving the user selection (e.g., chromosome 1), in FIG. 33, ancestry compositions associated with the selected chromosome are displayed in response. Although a list view is shown, other views such as the circle view shown in the preceding diagrams can also be presented. Subregions and inheritance of ancestries from a particular parent can be shown in similar manners as described in connection with FIGS. 28-31.

A pipelined ancestry deconvolution process and display of results have been described. The accuracy of ancestry predictions is greatly improved over existing techniques, and the results are presented in an informative and user-friendly fashion.

Although the foregoing embodiments have been described in some detail for purposes of clarity of understanding, the invention is not limited to the details provided. There are many alternative ways of implementing the invention. The disclosed embodiments are illustrative and not restrictive.

CONCLUSION

Unless the context of this disclosure clearly requires otherwise, throughout the description and the claims, the words using the singular or plural number also generally include the plural or singular number respectively. Additionally, the words "herein," "hereunder," "above," "below," and words of similar import refer to this disclosure as a whole and not to any particular portions of this application. When the word "or" is used in reference to a list of two or more items, that word covers all of the following interpretations of the word: any of the items in the list, all of the items in the list, and any combination of the items in the list. The term "implementation" refers to implementations of computational and physical methods described herein, as well as to computational routines that embody algorithms, models, and/or methods described herein. Numerical or mathematical values, including end points of numerical ranges, are not to be interpreted with more significant digits than presented.

Various computational elements including processors, memory, instructions, routines, models, or other components may be described or claimed as "configured to" perform a task or tasks. In such contexts, the phrase "configured to" is used to connote structure by indicating that the component includes structure (e.g., stored instructions, circuitry, etc.) that performs the task or tasks during operation. As such, the unit/circuit/component can be said to be configured to perform the task even when the specified component is not necessarily currently operational (e.g., is not on).

The components used with the "configured to" language may refer to hardware—for example, circuits, memory storing program instructions executable to implement the operation, etc. Additionally, "configured to" can refer to generic structure (e.g., generic circuitry) that is manipulated by software and/or firmware (e.g., an FPGA or a general-purpose processor executing software) to operate in manner that is capable of performing the recited task(s). Additionally, "configured to" can refer to one or more memories or memory elements storing computer executable instructions for performing the recited task(s). Such memory elements may include memory on a computer chip having processing logic, as well as main memory, system memory, and the like.

Although the foregoing embodiments and examples have been described in some detail for purposes of clarity of understanding, it will be apparent that certain changes and modifications may be practiced within the scope of the appended claims. Embodiments disclosed herein may be practiced without some or all these details. In other instances, well-known process operations have not been described in detail to not unnecessarily obscure the disclosed embodiments. Further, while the disclosed embodiments will be described in conjunction with specific embodiments, it will be understood that the embodiments are not intended to limit the disclosed embodiments. There are many alternative ways of implementing the processes, systems, and apparatus of the present embodiments. Accordingly, the present embodiments are to be considered as illustrative and not restrictive, and the embodiments are not to be limited to the details given herein.

What is claimed is:

1. A method comprising:
   obtaining, by way of one or more processors and from a classifier, initial ancestry classifications based on chromosome data of an individual;
   identifying, by way of the one or more processors, an initial Hidden Markov Model (HMM);
   refining, by way of the one or more processors, parameters of the initial HMM with the chromosome data of the individual;
   performing, by way of the one or more processors, error correction on the initial ancestry classifications, wherein the error correction involves applying an error correction model based on the initial HMM as refined to the initial ancestry classifications to form corrected ancestry classifications; and
   providing, by way of the one or more processors, the corrected ancestry classifications for storage or display.

2. The method of claim 1, wherein the chromosome data of the individual is from a plurality of chromosomes of the individual.

3. The method of claim 1, wherein obtaining the initial ancestry classifications based on the chromosome data of the individual comprises:
   obtaining unphased chromosome data of the individual; and
   determining, using dynamic programming and based on a predetermined reference haplotype graph, phased chromosome data of the individual from the unphased chromosome data of the individual, wherein the chromosome data of the individual is based on the phased chromosome data of the individual.

4. The method of claim 3, wherein obtaining the initial ancestry classifications based on the chromosome data of the individual further comprises:
   performing trio-based phasing of the phased chromosome data of the individual, wherein the trio-based phasing incorporates genotyping data of one or more biological parents of the individual.

5. The method of claim 3, wherein the predetermined reference haplotype graph is a probabilistic representation of two or more possible haplotype substrings as a directed acyclic graph.

6. The method of claim 5, wherein the directed acyclic graph is modified to include additional edges that account for recombination and genotyping errors.

7. The method of claim 5, wherein the directed acyclic graph is modified to exclude paths with an overall probability less than a given threshold.

8. The method of claim 1 wherein the error correction model is also based on a templated positional Burrows-Wheeler transform.

9. The method of claim 1, wherein obtaining the initial ancestry classifications based on the chromosome data of the individual comprises:
   obtaining a plurality of ancestries, wherein each of the ancestries is respectively associated with reference chromosome data of unadmixed individuals;
   training the classifier based on the reference chromosome data and the respectively associated ancestries;
   dividing the chromosome data of the individual into segments; and
   determining the initial ancestry classifications from applying the classifier to the segments.

10. The method of claim 9, wherein each of the unadmixed individuals has self-identified as being of a specific ancestry or has four grandparents of the specific ancestry.

11. The method of claim 9, wherein the classifier is configured to provide, for a given segment of the chromosome data, two or more probabilities associated with the given segment being of corresponding ancestries, and wherein determining the initial ancestry classifications from applying the classifier to the segments comprises selecting a corresponding ancestry with a highest probability for the given segment.

12. The method of claim 9, wherein training the classifier based on the reference chromosome data and the respectively associated ancestries comprises training the classifier based on the reference chromosome data from at least 14,400 unrelated individuals each with unadmixed ancestry.

13. The method of claim 9, wherein the segments are each of a size between 100 markers and 500 markers.

14. The method of claim 1, wherein the initial HMM is a Pair Hidden Markov Model (PHMM) in which an observed state corresponds to the initial ancestry classifications associated with a portion of one of two haplotypes of the individual, and a hidden state corresponds to ancestries associated with a corresponding portion of the two haplotypes of the individual.

15. The method of claim 1, wherein the initial HMM is an Autoregressive Pair Hidden Markov Model (PHMM) in which an observed state depends on its corresponding hidden state and its previous observed state.

16. The method of claim 1, wherein applying the error correction model based on the initial HMM as refined to the initial ancestry classifications to form the corrected ancestry classifications comprises:
   determining transition parameters of the error correction model; and
   based on error correction results of the error correction model, repeatedly updating the transition parameters until the error correction results converge.

17. The method of claim 1, wherein the initial HMM is selected from a pool of pre-trained HMMs, and wherein each of the pre-trained HMMs has respective transition parameters based on an unsupervised training procedure performed on samples of approximately 1000 individuals of respective regional ancestries.

18. The method of claim 1, wherein the corrected ancestry classifications are a most probable sequence of ancestry assignments for the chromosome data of the individual and posterior probabilities associated with each of the ancestry assignments, and wherein the posterior probabilities have been recalibrated based on reference chromosome data of unadmixed individuals or simulated admixed individuals until a given threshold confidence level of the posterior probabilities is reached.

19. A non-transitory computer-readable medium storing program instructions that, when executed by one or more processors of a computing system, cause the computing system to perform operations comprising:
   obtaining, from a classifier, initial ancestry classifications based on chromosome data of an individual;
   identifying an initial Hidden Markov Model (HMM);
   refining parameters of the initial HMM with the chromosome data of the individual;
   performing error correction on the initial ancestry classifications, wherein the error correction involves applying an error correction model based on the initial HMM as refined to the initial ancestry classifications to form corrected ancestry classifications; and
   providing the corrected ancestry classifications for storage or display.

20. A computing system comprising:
   one or more processors;
   memory; and
   program instructions, stored in the memory, that upon execution by the one or more processors cause the computing system to perform operations comprising:
      obtaining, from a classifier, initial ancestry classifications based on chromosome data of an individual;
      identifying an initial Hidden Markov Model (HMM);
      refining parameters of the initial HMM with the chromosome data of the individual;
      performing error correction on the initial ancestry classifications, wherein the error correction involves applying an error correction model based on the initial HMM as refined to the initial ancestry classifications to form corrected ancestry classifications; and
      providing the corrected ancestry classifications for storage or display.

* * * * *